United States Patent [19]

Danishefsky et al.

[11] Patent Number: 5,525,731
[45] Date of Patent: Jun. 11, 1996

[54] CAMPTOTHECIN ANALOGUES AND METHODS OF PREPARATION THEREOF

[75] Inventors: Samuel J. Danishefsky, New Haven, Conn.; Lawrence B. Snyder, New York, N.Y.

[73] Assignee: Sloan-Kettering Institute for Cancer Research, New York, N.Y.

[21] Appl. No.: 328,415

[22] Filed: Oct. 25, 1994

Related U.S. Application Data

[63] Continuation-in-part of Ser. No. 2,996, Jan. 11, 1993, Pat. No. 5,391,745, which is a continuation-in-part of Ser. No. 919,188, Jul. 23, 1992, Pat. No. 5,446,047.

[51] Int. Cl.[6] .................... C07D 491/22; A61K 31/435
[52] U.S. Cl. ............................... 546/48; 536/17.4
[58] Field of Search ............... 546/48; 536/17.4; 514/27, 283

[56] References Cited

U.S. PATENT DOCUMENTS

| | | | |
|---|---|---|---|
| 3,894,029 | 7/1975 | Winterfeldt et al. | 260/287 R |
| 4,031,098 | 6/1977 | Sugasawa | 260/287 C |
| 4,399,282 | 8/1983 | Miyasaka et al. | 546/48 |
| 4,473,692 | 9/1984 | Miyasaka et al. | 546/48 |
| 4,513,138 | 4/1985 | Miyasaka et al. | 546/48 |
| 4,545,880 | 10/1985 | Miyasaka et al. | 204/158 |
| 4,604,463 | 8/1986 | Miyasaka et al. | 544/125 |
| 4,894,456 | 1/1990 | Wall et al. | 546/41 |
| 4,914,205 | 4/1990 | Sawada et al. | 546/70 |
| 4,939,255 | 7/1990 | Tagawa et al. | 540/578 |
| 4,943,579 | 7/1990 | Vishnuvajjala et al. | 514/283 |
| 4,981,968 | 1/1991 | Wall et al. | 544/361 |
| 5,004,758 | 4/1991 | Boehm et al. | 514/283 |
| 5,049,668 | 9/1991 | Wall et al. | 540/481 |
| 5,061,795 | 10/1991 | Tagawa et al. | 540/578 |
| 5,061,800 | 10/1991 | Yaegashi et al. | 546/48 |
| 5,106,742 | 4/1992 | Wall et al. | 435/233 |
| 5,112,526 | 6/1992 | Wall et al. | 514/253 |

OTHER PUBLICATIONS

Danishefsky, S., and Etheredge, S. J., *J. Org. Chem.*, 39:3430–3432 (1974); U.S.A.

Giovanella, B. C., et al., *Science*, 246:1046–1048 (1989); U.S.A.

Hsiang, Y.-H., et al., *J. Biol. Chem.*, 260:14873–14878 (1985); U.S.A.

Hsiang, Y.-H., and Liu, L. F., *Cancer Research*, 48:1722–1726 (1988); U.S.A.

T. Kunimoto, et al., *Cancer Research*, 47:5944–5947 (1987); U.S.A.

*Primary Examiner*—Bernard Dentz
*Attorney, Agent, or Firm*—John P. White

[57] ABSTRACT

Substituted analogues of camptothecin possessing cytotoxic activity towards cancer cells, of the general structure:

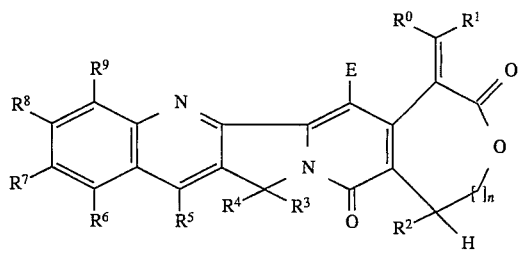

wherein E is H, $CO_2R$, $CONH_2$, $CONHR$, $CONR_2$, or CN; $R^0$ and $R^1$ are independently the same or different and are H, or a linear or branched alkyl, linear or branched alkylaryl, hydroxyalkyl or aryl group; $R^2$, $R^3$ and $R^4$ are independently the same or different and are H, or a linear or branched alkyl, linear or branched alkylaryl, hydroxyalkyl or aryl group; $R^5$, $R^6$, $R^7$, $R^8$ and $R^9$ are independently the same or different and are H, or a linear or branched alkyl, linear or branched alkylaryl or aryl group, or an alkoxy, aryloxy, hydroxyalkyl, C-glycal, nitro, cyano or aminoalkoxy group, or $CO_2R$, Cl, F, Br, I, $SR^{10}$, $NR^{11}R^{12}$ or $OR^{13}$; R is H, an alkyl, aryl, alkylaryl or hydroxyalkyl group; $R^{10}$, $R^{11}$ and $R^{12}$ are independently the same or different and are H, an alkyl, aryl, alkylaryl or acyl group; $R^{13}$ is glycosyl; and n is 0 or 1. Also provided are compositions comprising the analogues and methods of treating tumors as well as methods for preparing the analogues.

36 Claims, 15 Drawing Sheets

FIGURE 1B a. Dimethyl sulfate
b. Meldrum's acid, triethylamine, benzene
c. Sodium methoxide, methanol
d. Dimethyl allene-1,3-dicarboxylate 5, triethylamine
e. Potassium t-butoxide, THF, Ethyl iodide
f. Formaldehyde, acid
g. Hydrobromic acid, reflux
h. Selenium dioxide, 160°C, dioxane
i. Pyridinium dichromate, 0°C
j. o-Aminophenyl toluidine, toluene, tosic acid

FIGURE 2B k. Selenium dioxide, 160°C, dioxane
l. Pyridinium dichromate, 0°C
m. o-Aminophenyl toluidine, toluene, tosic acid

FIGURE 3B a. Davis' oxaziridine, KHMDS, THF
b. Pyridinium dichromate, 0°C
c. o-Aminophenyl toluidine, toluene, tosic acid
d. Hydrobromic acid, reflux
e. $CuCl_2$, oxygen, dimethylamine, DMF

FIGURE 4B a. Davis' oxaziridine, KHMDS, THF
b. Pyridinium dichromate, 0°C
c. o-Aminophenyl toluidine, toluene, tosic acid
d. $CuCl_2$, oxygen, dimethylamine, DMF X=R=H; Z=OH (camptothecin)
X=OH; R=Et; Z=OH (SN-38)

36 X=R=Z=H

37 X=OH; R=Et; Z=H

32 X=R=R'=H

33 X=OH; R=Et; R'=H

34 X=R=H; R'=Me

35 X=H; R=Et; R'=Me

38

42 R=R'=H

45 R=Br; R'=H

46 R= CH=CH2; R'=H

47 R= CH=CH2; R'=Me

48 X=H; OH

49 X=O

52  R = CO$_2$Me; R' = H

54  R = R' = H

55  R = H; R' = SePh ⟶ 32

53  R = Me; R' = CO$_2$Me; R'' = H

56  R = R' = R'' = H

57  R = R' = H; R'' = SePh ⟶ 33

CAMPTOTHECIN ANALOGUES AND METHODS OF PREPARATION THEREOF

This application is a continuation-in-part of U.S. Ser. No. 08/002,996, filed Jan. 11, 1993 now U.S. Pat. No. 5,391,745, which was a continuation-in-part of U.S. Ser. No. 07/919,188, filed Jul. 23, 1992 now U.S. Pat. No. 5,446,047, the contents of which are hereby incorporated by reference into this application.

BACKGROUND OF THE INVENTION

The invention described herein was made in the course of work under Grant Number AI16943 from the National Institutes of Health, U.S. Department of Health and Human Services. The U.S. Government may have certain rights in this invention.

This invention relates to new camptothecin analogues useful for the treatment of cancer, to intermediates useful for their synthesis, and to methods of preparing the analogues and intermediates.

Camptothecin (1) is a pentacyclic alkaloid possessing a fused quinoline in rings A and B, a pyrroline in ring C, an α-pyridone in ring D, and a six-membered lactone in ring E, and was first isolated from *Camptotheca acuminata* (Nyssaceae), a tree native to southern China (Wall, et al., *J. Amer. Chem. Soc.*, 88, 3888–3890 (1966)). Promising antitumor and antileukemic activity and extreme rarity of the compound in nature (present in stem bark at abundances of about 0.01% by weight) have motivated extensive studies directed toward the total synthesis of camptothecin as well as the design of analogues intended to exhibit greater activity and lower toxicity than camptothecin itself. The results of these efforts have been comprehensively reviewed (C. R. Hutchinson, *Tetrahedron*, 37, 1047–1065 (1981); A. G. Schultz, *Chemical Rev.*, 73, 385–405 (1973)).

Mechanistic studies of the biological action of camptothecin have pointed to the enzyme topoisomerase I as the main intracellular target of the compound. By binding to and stabilizing a covalent DNA-topoisomerase I complex in which a strand of DNA is broken (R. P. Hertzberg, et al., *J. Med. Chem.*, 32, 715 (1989); W. D. Kingsbury, et al., *J. Med. Chem.*, 34, 98 (1991)), it is believed, camptothecin damages DNA and strongly inhibits the synthesis of nucleic acids in cancer cells. A structure-activity correlation for camptothecin analogues has been established between the anti-cancer activity of an analogue and its ability to stabilize the DNA-topoisomerase I complex. Adding further weight to this belief, cell lines which are resistant to camptothecin have been determined to contain a mutated form of topoisomerase I (R. S. Gupta, et al., *Cancer Res.*, 48, 6404 (1988)).

High toxicity and low solubility have diminished the clinical utility of camptothecin, stimulating a search for derivatives which transcend these limitations. Numerous analogues have been prepared by methods described in previous disclosures. None of these methods, however, offer a general approach for preparing camptothecin analogues with highly variable ring substitution patterns. For example, Miyasaka, et al. (U.S. Pat. No. 4,399,282, issued Aug. 16, 1982), disclose camptothecin analogues substituted by an alkyl, aralkyl, alkoxycarbonyl, or alkoxyalkyl group exclusively in the 7-position, while. J. C. Boehm, et al. (U.S. Pat. No. 5,004,758, issued Apr. 2, 1991), disclose camptothecins substituted at positions 9 and 10, and Miyasaka, et al. (U.S. Pat. No. 4,473,692, issued Sep. 25, 1984) provide compounds with certain groups located at positions 5, 7, and 10, but not otherwise. Because of the sparing solubility of camptothecin in many organic solvents, and because of the special characteristic of camptothecin that the aromatic rings lack sufficient reactivity to afford ring-substituted analogues, the usual electrophilic ring substitution reactions cannot be performed productively on the parent structure. As a result, few direct methods exist for the preparation of potentially valuable substitution patterns. In one exceptional instance, nitration has been effected by Chinese workers (P. Peichuang, et al., *Hau Hsueh Hsueh Pao*, 33, 71 (1975); *Chem. Abstr.*, 84, 115629p (1975)) at the 12-position under severe conditions (nitric acid/sulfuric acid) at the 9-position of a 10,11-methylenedioxycamptothecin (M. E. Wall, et al., U.S. Pat. No. 5,049,668, issued Sep. 17, 1991), and at the 10-position by proceeding through a tetrahydrocamptothecin intermediate followed by subsequent re-oxidation (Miyasaka, et al., U.S. Pat. No. 4,473,692, issued Aug. 25, 1984), thereby allowing access to a range of substitution but at the cost of starting from the rare native camptothecin or its analogues.

Chemical modifications of the A, B, or C rings are of greatest therapeutic interest based on previous structure-function studies. However, while most alterations in the D and E rings have resulted in depressed biological activity, certain modifications of these rings have been achieved without losing activity, as disclosed in U.S. Pat. Nos. 3,894,029, issued Jul. 18, 1975, 4,031,098, issued Jun. 21, 1977, 4,914,205, issued Apr. 3, 199, and 4,943,579, issued Jul. 24, 1990. The present invention allows simultaneous substitution changes in all rings of camptothecin.

While several syntheses of camptothecin have been disclosed in prior art (for example, E. J. Corey, et al., *J. Amer. Chem. Soc.*, 40, 2140 (1975); J. C. Bradley, et al., *J. Org. Chem.*, 41, 699 (1976); G. Stork, et al., *J. Amer. Chem. Soc.*, 93, 4074 (1971); E. Winterfeld, et al., *Angew. Chem.*, 84, 265 (1972)), the present approach offers the combined advantages of good preparative yield, a minimum number of reaction steps, and synthetic flexibility in the design of derivative analogues of camptothecin. Certain embodiments of the present invention allow synthetic yields of camptothecin as high as 39% from abundantly available tricyclic pyridones. Because of the possibility of obtaining a large variety of analogues, and given the intense anti-cancer activity of the parent structure, the present invention makes feasible the large-scale synthesis of a many new anti-cancer pharmaceuticals with more desirable chemical and clinical properties. Valuable enhancements in properties include improved solubility, bioavailability, and anticancer activity. The present invention therefore provides methods which represent a potentially significant advance for cancer chemotherapy.

BRIEF DESCRIPTION OF THE FIGURES

A more complete understanding of the invention and many of its advantages will become apparent by reference to the detailed description which follows when considered in conjunction with the accompanying figures wherein:

FIGS. 1A and 1B illustrate the preparation of native camptothecin via decarboxylation and SeO$_2$-mediated oxygenation and of a de-AB-camptothecin intermediate according to the process of the subject invention.

FIGS. 2A and 2B provide the synthesis of 14-carbomethoxy-substituted dl-camptothecin via SeO$_2$-mediated oxygentation of a de-AB-camptothecin intermediate according to the process of the subject invention.

FIGS. 3A and 3B show the preparation of native camptothecin via decarboxylation and Davis' oxaziridine-mediated oxygenation and of a 14-carbomethoxy-substituted de-AB-camptothecin intermediate according to the process of the subject the invention.

FIGS. 4A and 4B exemplify the synthesis of 14-carbomethoxy-substituted camptothecin analogues via Davis' oxaziridine-mediated oxygenation of a de-AB-camptothecin intermediate according to the process of the subject invention.

SUMMARY OF THE INVENTION

Figure 1A:
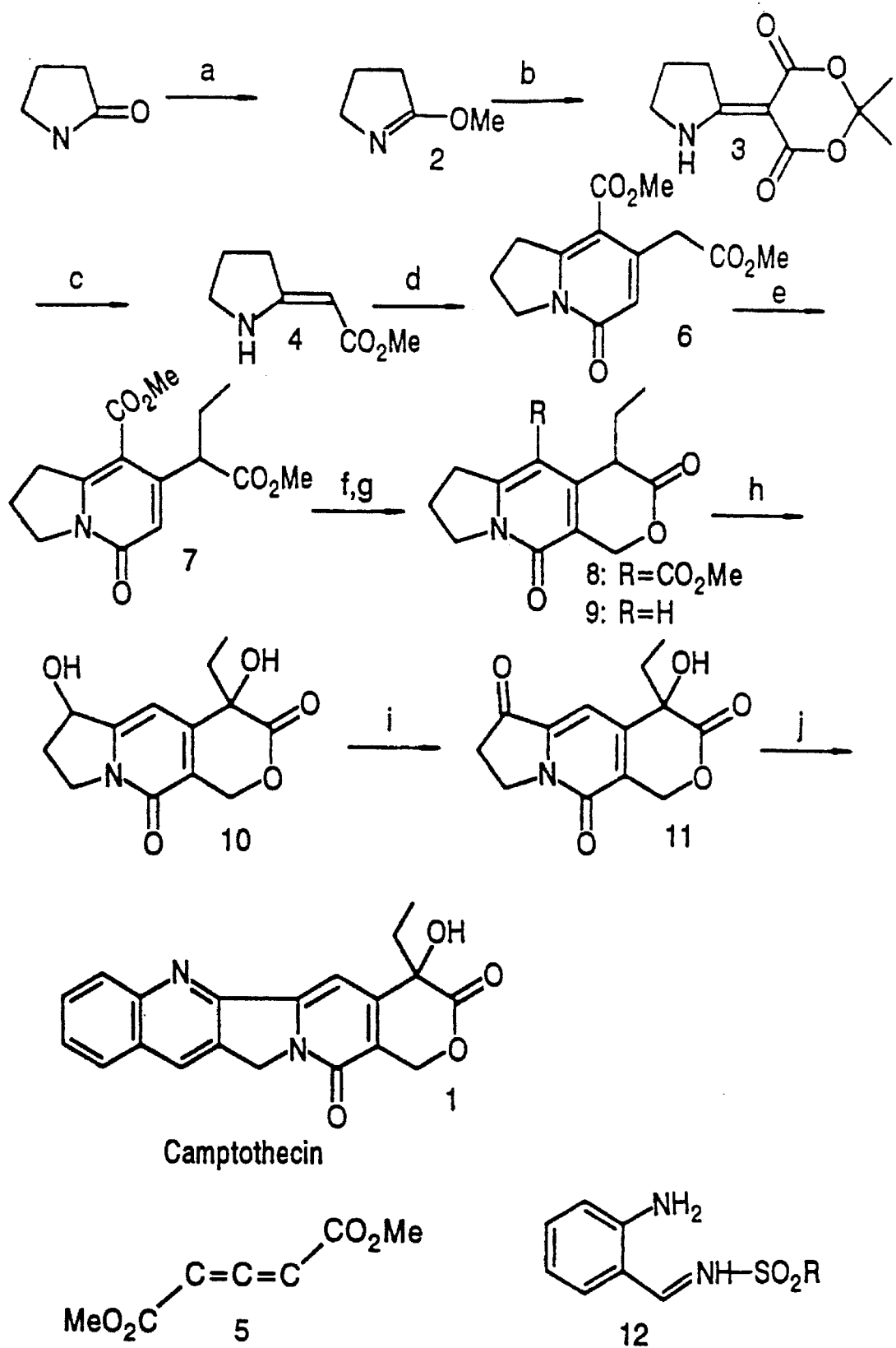
Figure 2A:
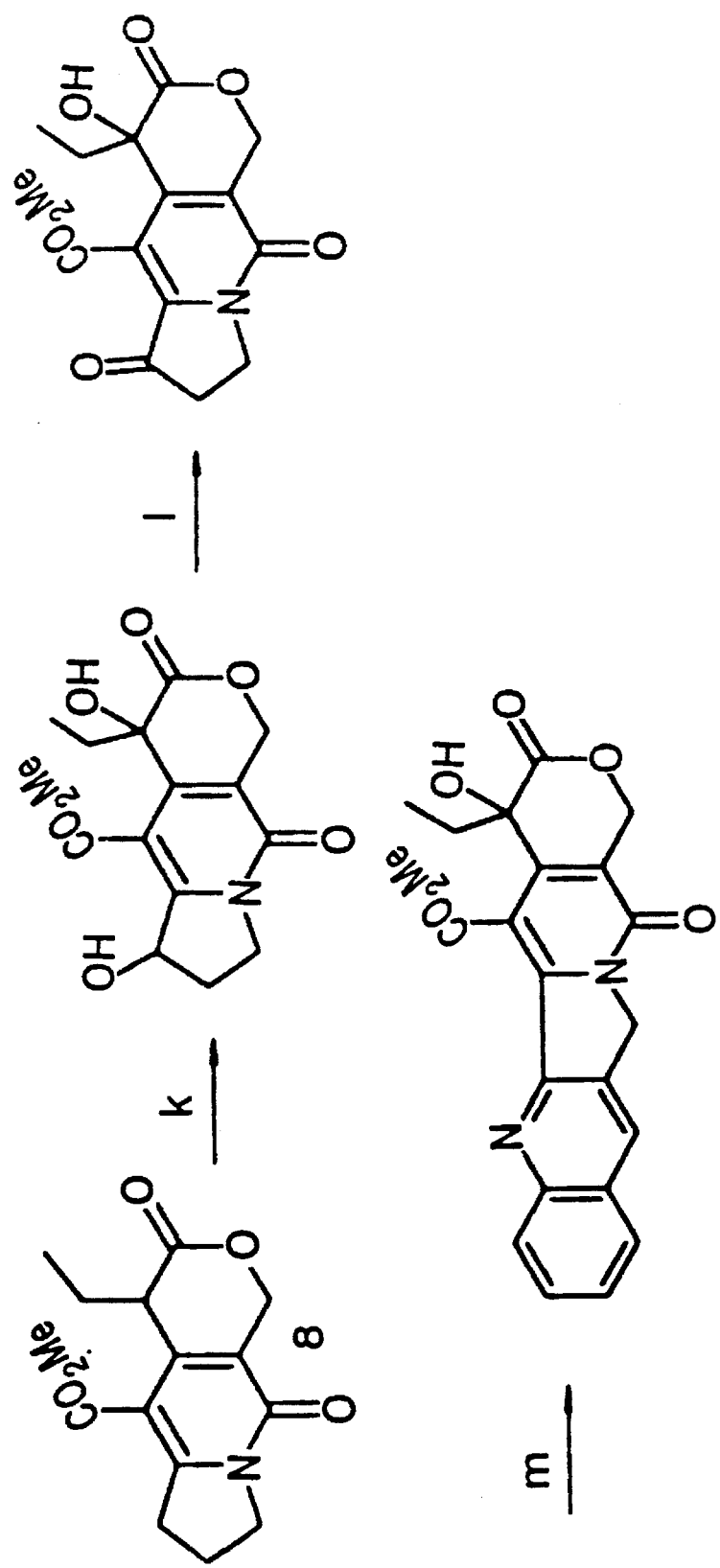
Figure 3A:
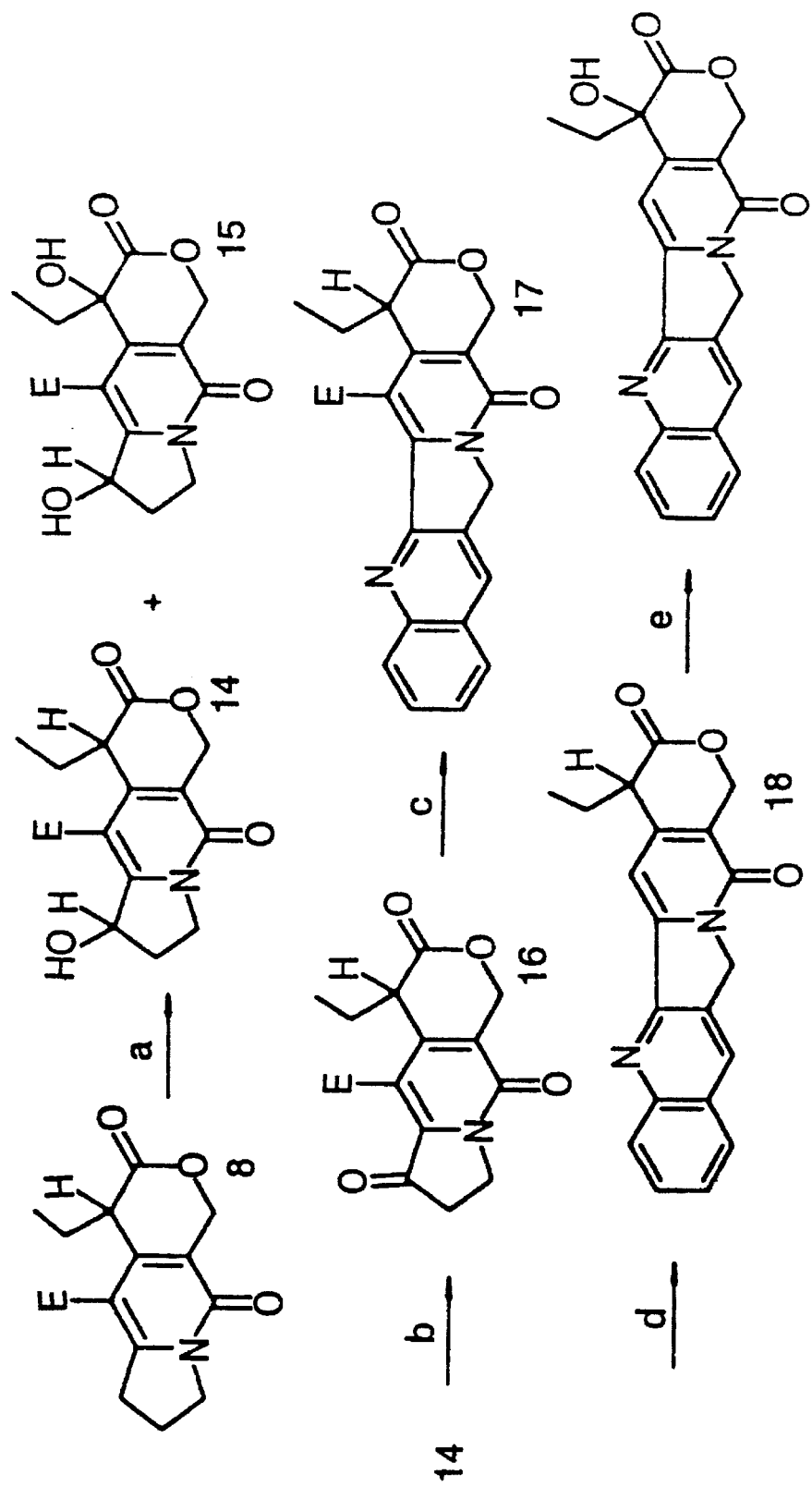
Figure 4A:
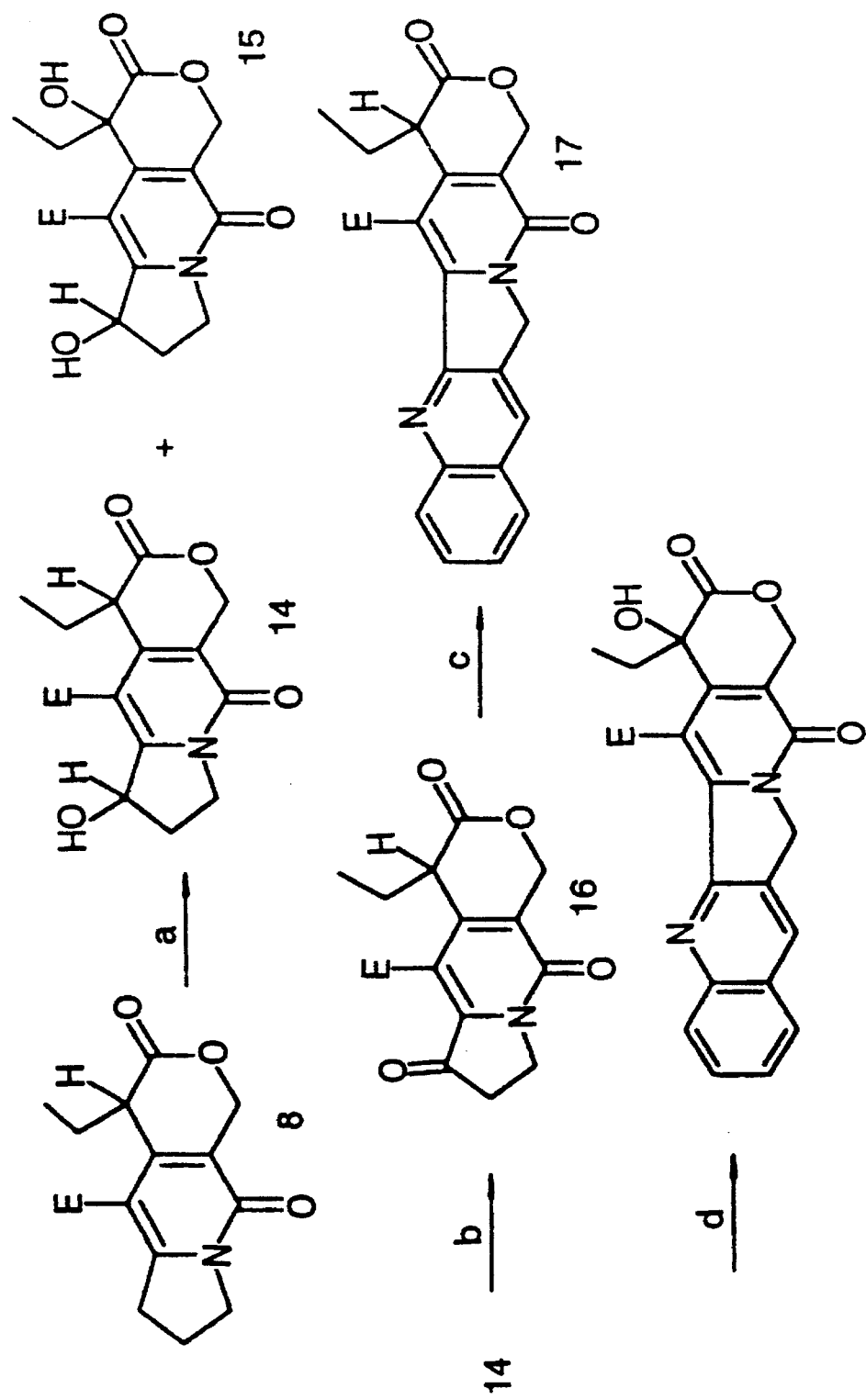
Figure 5:
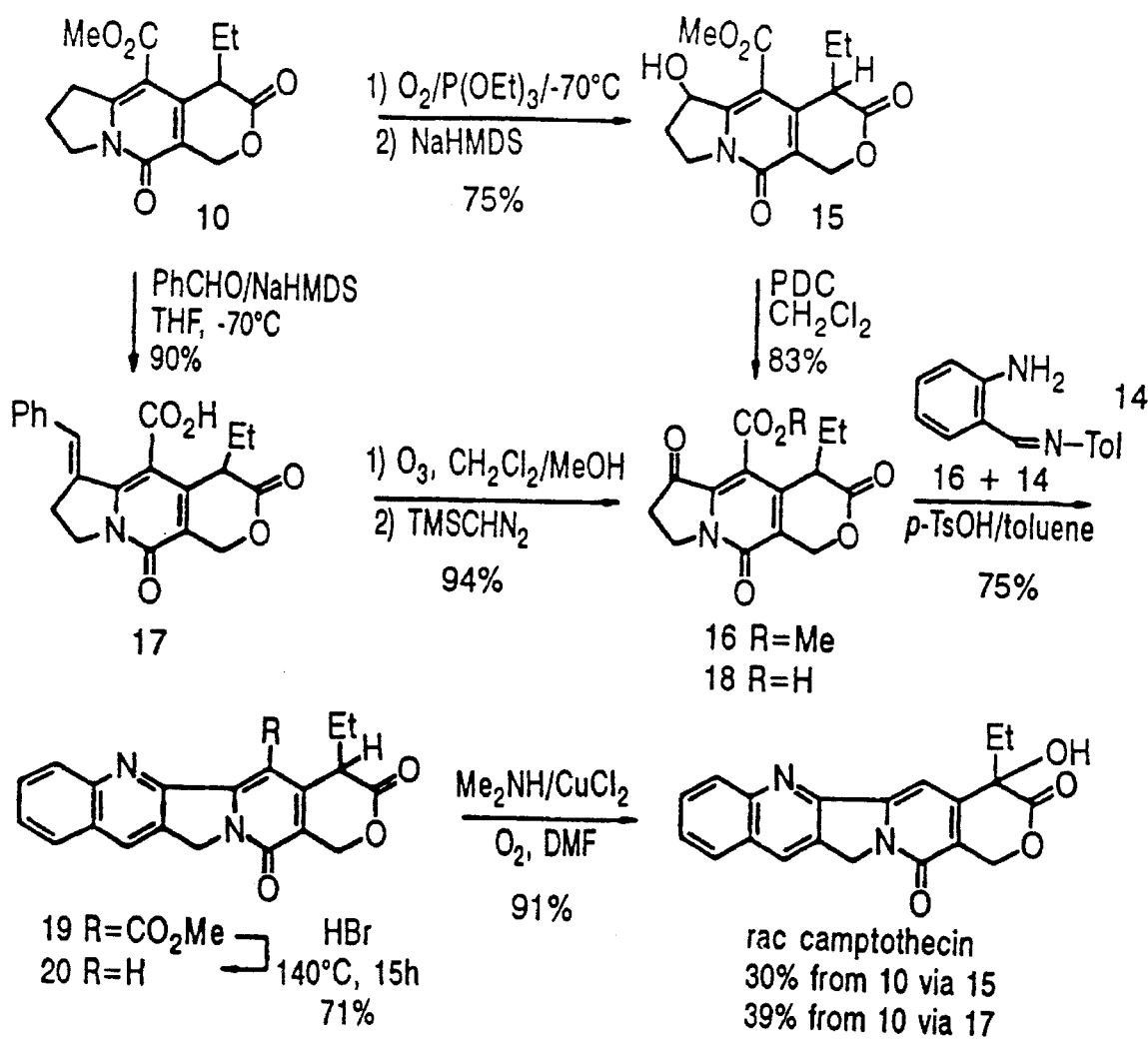
FIG. 5 illustrates the preparation of native camptothecin via a benzylidene or ketotricyclic intermediate according to the process of the subject invention.
Figure 6:
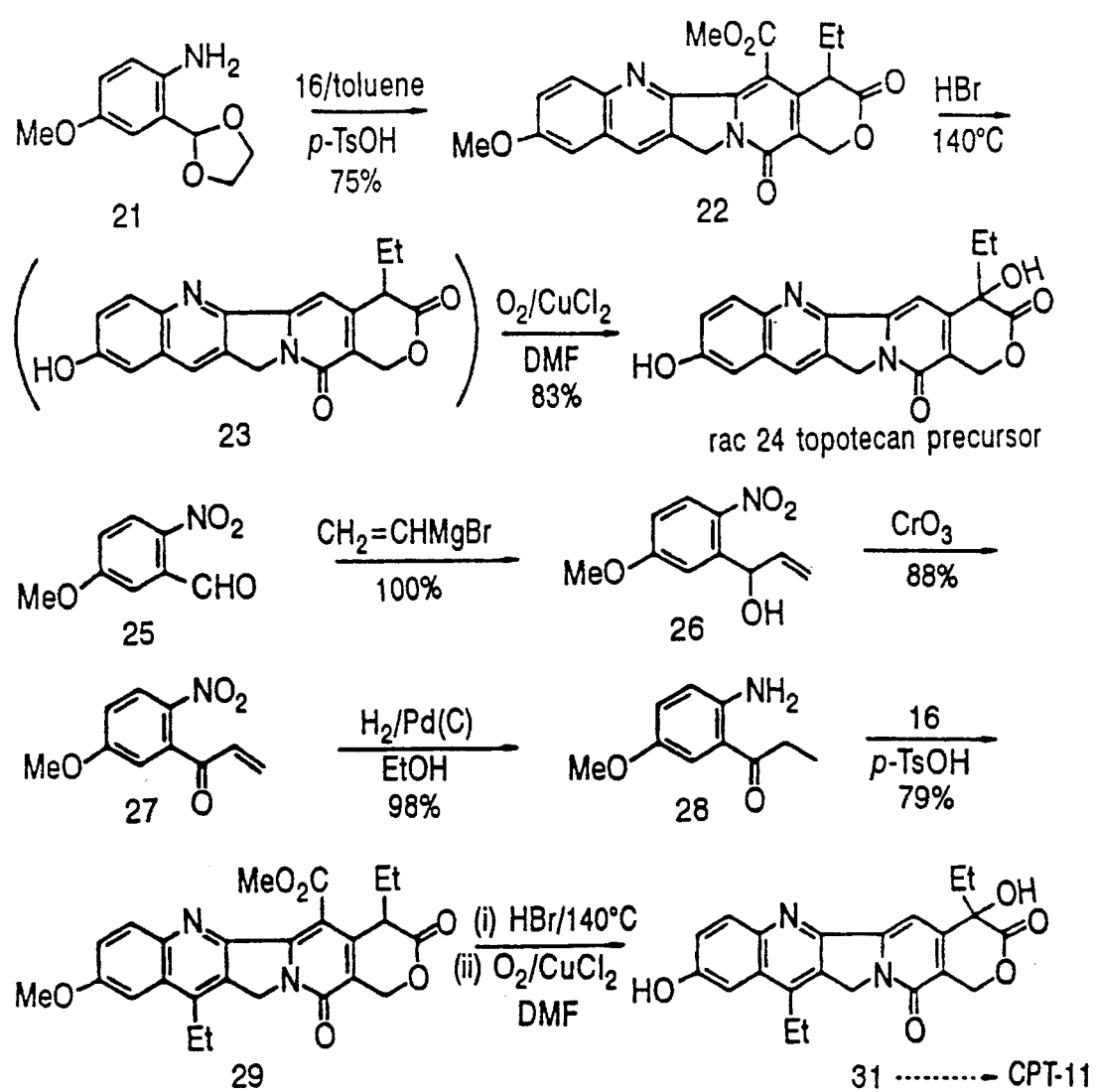
FIG. 6 illustrates the synthesis of a topotecan precursor and 10-hydroxycamptothecin derivatives via a vinyl Grignard aldol intermediate according to the process of the subject invention.

The present invention relates to new substituted analogues of camptothecin bearing one or more groups in the 5-, 7-, 10-, 11-, 12-, 14-, 17- and/or 20-position thereof, and to methods of preparation of camptothecin and new analogues thereof.

Thus, the present invention provides a compound having the structure:

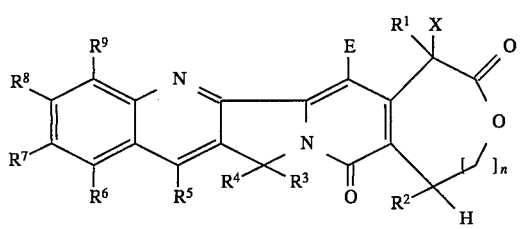

wherein E is H, $CO_2R$, $CONH_2$, CONHR, $CONR_2$, acyl, or CN; X, $R^1$ is O, or X is H or OH and $R^1$ is H, or a linear or branched chain alkyl, alkylaryl, or hydroxyalkyl group, or an aryl group; $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or a C-glycal, or $CO_2R$, nitro, cyano, Cl, F, Br, I, $SR^{10}$, or NR is H, or $NR^{11}R^{12}$, $OR^{13}$; R is H, or a linear or branched chain alkyl, alkylaryl, or hydroxyalkyl group, or an aryl group; $R^{10}$, $R^{11}$ and $R^{12}$ are independently the same or different and are H, alkyl, aryl, alkylaryl, or acyl; $R^{13}$ is glycosyl; n is 0 or 1; with the proviso that when $R^1$ is ethyl, and n is O, E, $R^2$, $R^3$, and $R^4$, are not all H. Another object of the invention is to provide key intermediates useful for the preparation of such new analogues of camptothecin. Thus, the invention also provides a compound having the structure:

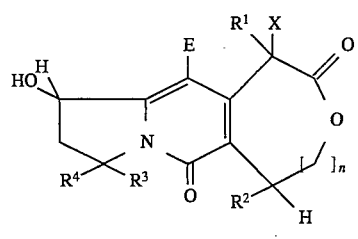

wherein E is H, $CO_2R$, $CONH_2$, CONHR, $CONR_2$, acyl, or CN; X is H, OH, or OR; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, with the proviso that when $R^1$ is ethyl, and n is O, E, $R^2$, $R^3$, and $R^4$ are not all H.

The invention further provides a compound having the structure:

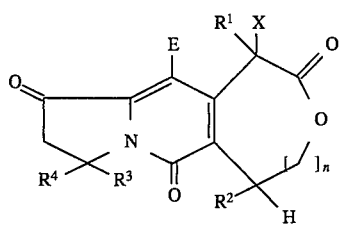

wherein E is H, $CO_2R$, $CONH_2$, CONHR, $CONR_2$, acyl, or CN; X is H, OH, or OR; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, with the proviso that when $R^1$ is ethyl, and n is O, E, $R^2$, $R^3$, and $R^4$ are not all H.

An object of the present invention is to provide a process of synthesizing a compound having the structure:

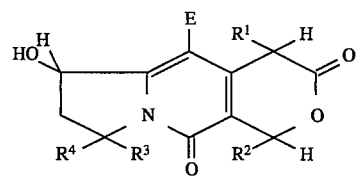

wherein E is H; X is OH; $R^1$, $R^2$, $R^3$, and $R^4$ are independently the same or different and are H, or a linear or branched chain alkyl, alkylaryl, or hydroxyalkyl group, or an aryl group; which comprises:

(a) treating the pyrrolidone having the structure:

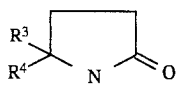

wherein $R^3$ and $R^4$ are independently the same or different and are H, or a linear or branched chain alkyl, or linear or branched alkylaryl, hydroxyalkyl, or aryl with an alkylating agent under suitable conditions to form a compound having the structure:

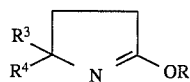

wherein $R^3$ and $R^4$ are independently the same or different and are H, or a linear or branched chain alkyl, or linear or branched alkylaryl, hydroxyalkyl, or aryl;

(b) condensing the compound formed by step (a) with Meldrum's acid in the presence of a base under conditions suitable to form a compound having the structure:

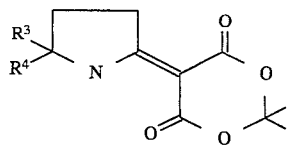

wherein $R^3$ and $R^4$ are independently the same or different and are H, or a linear or branched chain alkyl, or linear or branched alkylaryl, hydroxyalkyl, or aryl;

(c) treating the compound formed by step (b) with alkali alkoxide under conditions suitable to form a compound having the structure:

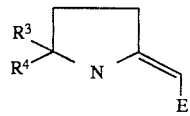

wherein $R^3$ and $R^4$ are independently the same or different and are H, or a linear or branched chain alkyl, or linear or branched alkylaryl, hydroxyalkyl, or aryl; and, E is $CO_2R$, $CONH_2$, CONHR, $CONR_2$, acyl, or CN; R is H, or a linear or branched chain alkyl, alkylaryl, or hydroxyalkyl group;

(d) reacting the compound formed by step (c) with a compound having the structure:

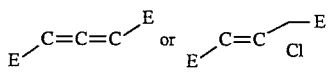

wherein E is $CO_2R$, $CONH_2$, CONHR, $CONR_2$, acyl, or CN; and, R is H, or a linear or branched chain alkyl, alkylaryl, or hydroxyalkyl group, under conditions suitable to form a compound having the structure:

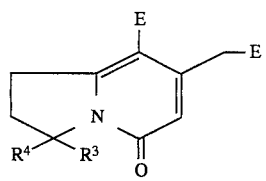

wherein $R^3$ and $R^4$ are independently the same or different and are H, or a linear or branched chain alkyl, or linear or branched alkylaryl, hydroxyalkyl, or aryl; E is $CO_2R$, $CONH_2$, CONHR, $CONR_2$, acyl, or CN; and, R is H, or a linear or branched chain alkyl, alkylaryl, or hydroxyalkyl group;

(e) deprotonating the compound formed by step (d) with a non-nucleophilic base to form an anion and alkylating the anion with an electrophilic reactant under conditions suitable to form a compound having the structure:

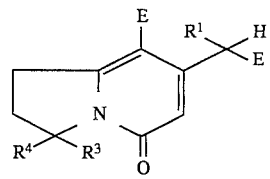

wherein E is $CO_2R$, $CONH_2$, CONHR, $CONR_2$, acyl, or CN; $R^1$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group;

(f) reacting the compound formed by step (e) with a carbonyl compound having the structure $R^2$—CHO, wherein $R^2$ is H, or a linear or branched chain alkyl, alkylaryl, or hydroxyalkyl group, or an aryl group, under suitable conditions to form a compound having the structure:

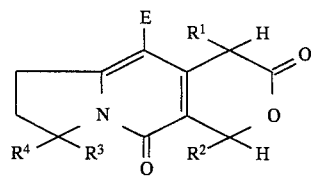

wherein E is $CO_2R$, $CONH_2$, CONHR, $CONR_2$, acyl or CN; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group;

(g) hydrolyzing and decarboxylating the compound formed by step (f) under suitable acidic conditions to form a compound having the structure:

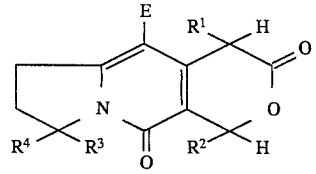

wherein E is H; $R^1$, $R^2$, $R^3$, and $R^4$ are independently the same or different and are H, or a linear or branched chain alkyl, alkylaryl, or hydroxyalkyl group, or an aryl group;

(h) treating the compound formed by step (g) with an hydroxylating reagent under conditions suitable to form the compound having the structure:

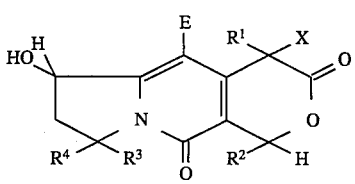

wherein E is H; X is OH; $R^1$, $R^2$, $R^3$, and $R^4$ are independently the same or different and are H, or a linear or branched chain alkyl, alkylaryl, or hydroxyalkyl group, or an aryl group.

The present invention provides a process of synthesizing a compound having the structure:

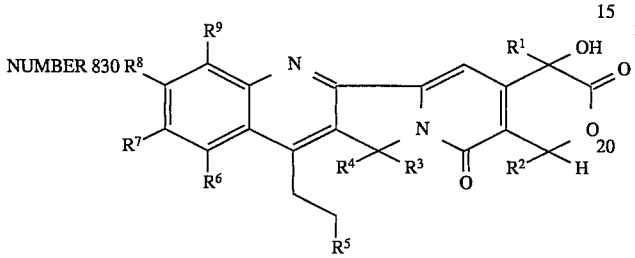

NUMBER 830 wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, which comprises:

(a) treating an arylaldehyde having the structure:

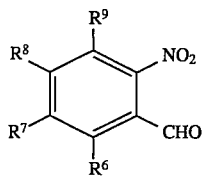

wherein $R^6$, $R^8$, and $R^9$ are independently the same or different and are H, or a linear or branched chain alkyl, alkylaryl, alkoxy, aminoalkoxy, or hydroxyalkyl group, or an aryl, aryloxy, or nitro group, or $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$, is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9, with a vinylic organometallic reagent having the structure:

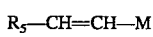

$R_5$—CH=CH—M wherein $R^5$ is a linear or branched chain alkyl, alkylaryl, alkoxyalkyl, aryloxyalkyl, or hydroxyalkyl group, or an aryl group or $(CH_2)_nNR^{11}R^{12}$ or $(CH_2)_nOR^{11}$, and M is Li, K, Na, MgCl, or MgBr; to form a compound having the structure:

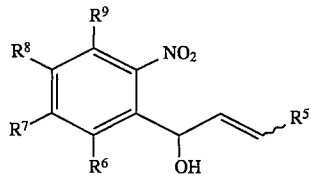

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$; and, n is an integer from 0 to 9;

(b) oxidizing the compound formed in step (a) with an oxidizing agent under suitable conditions to form a compound having the structure:

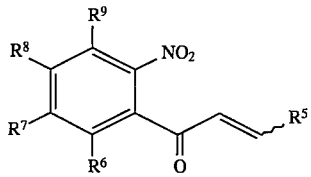

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$; $R^6$, $R^8$, and $R^9$ are independently the same or different and are H, or a linear or branched chain alkyl, alkylaryl, alkoxy, aminoalkoxy, or hydroxyalkyl group, or an aryl, aryloxy, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9;

(c) reducing the compound formed in step (b) under suitable conditions to form a compound having the structure:

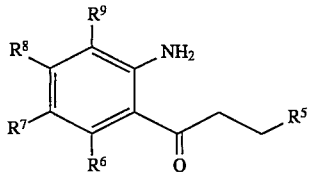

wherein $R^5$ is a linear or branched chain alkyl, alkylaryl, alkoxyalkyl, aryloxyalkyl, or hydroxyalkyl group, or an aryl group or $(CH_2)_nNR^{11}R^{12}$, or $(CH_2)_nOR^{11}$; $R^6$, $R^8$, and $R^9$ are independently the same or different and are H, or a linear or branched chain alkyl, alkylaryl, alkoxy, aminoalkoxy, or hydroxyalkyl group, or an aryl, or aryloxy, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$, is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9;

(d) condensing the compound formed in step (c) with a compound having the structure:

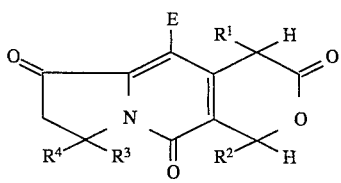

wherein S is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; in the presence of an acid catalyst under suitable conditions to form a compound having the structure:

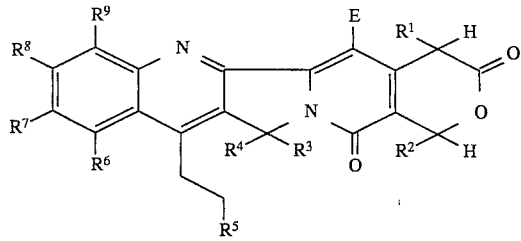

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9;

(e) hydrolyzing and decarboxylating the compound formed in step (d) using an acid under suitable conditions to form a compound having the structure:

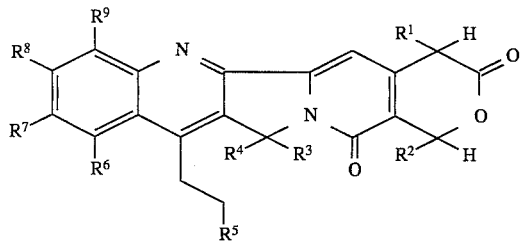

wherein $R^1$, $R^2$, $R^3$, and $R^4$ are independently the same or different and are H, or a linear or branched chain alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9; and (f) treating the compound formed in step (e) with a hydroxylating reagent under suitable conditions to form a compound having the structure:

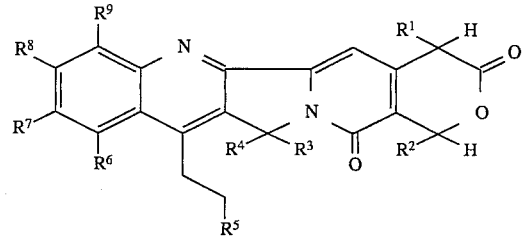

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and are independently $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and, n is an integer from 0 to 9.

The invention also provides a process of synthesizing a compound having the structure:

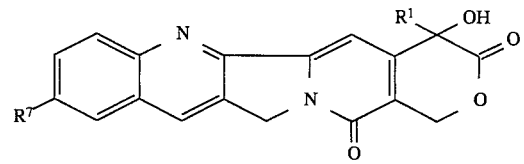

wherein $R^1$ is ethyl and $R^7$ is OH, which comprises:

(a) condensing a compound having the structure:

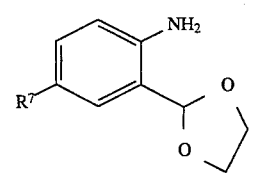

wherein $R^7$ is OH with a compound having the structure:

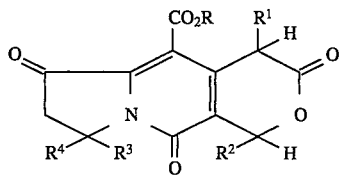

wherein R is H, or a linear or branched chain alkyl, alkylaryl, or hydroxyalkyl group, or an aryl group; $R^1$ is ethyl; $R^2$, $R^3$ and $R^4$ are H; and, is OR, $R^7$ with a suitable acidic catalyst comprising p-toluenesulfonic acid in toluene to form a compound having the structure:

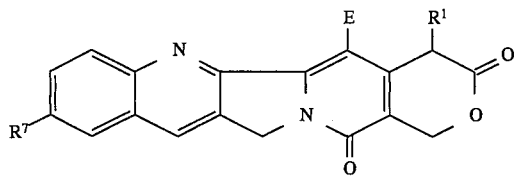

wherein R is H, or a linear or branched chain alkyl, alkylaryl, or hydroxyalkyl group, or an aryl group; $R^1$ is ethyl; and, $R^7$ is OR;

(b) hydrolyzing and decarboxylating the compound formed in step (a) with a suitable acid comprising hydrobromic acid to form a compound having the structure:

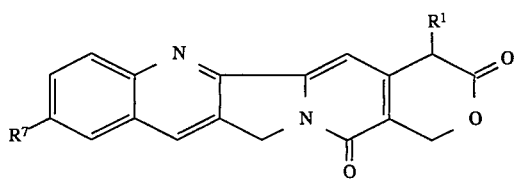

wherein $R^1$ is ethyl and $R^7$ is OR; and (c) treating the compound formed in step (b) with a hydroxylating reagent under suitable conditions to form a compound having the structure:

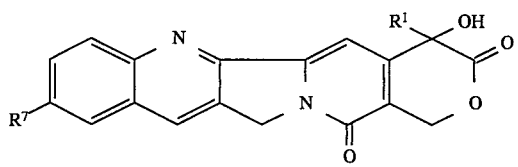

wherein $R^1$ is ethyl and $R^7$ is OH.

The invention further provides a process of synthesizing a compound having the structure:

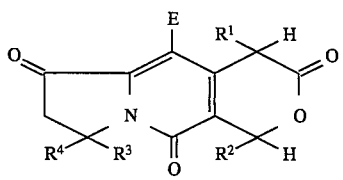

wherein E is H, $CO_2R$, $CONH_2$, CONHR $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) treating a compound having the structure:

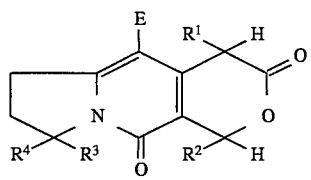

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; with a hydroxylating reagent under suitable conditions to form a compound having the structure:

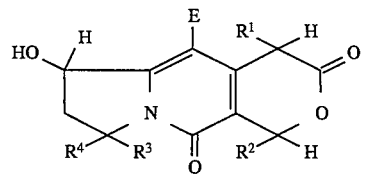

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) oxidizing the compound formed by step (a) with an oxidant under suitable conditions to form a compound having the structure:

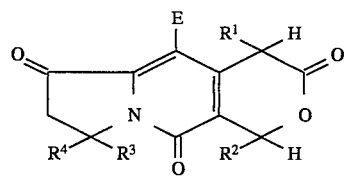

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group.

The invention additionally provides a process of synthesizing a compound having the structure:

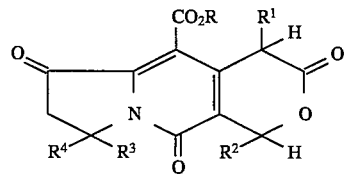

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) condensing an aryl aldehyde with a compound having the structure:

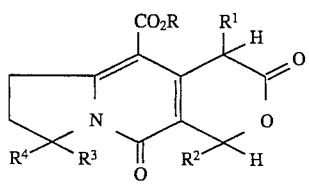

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, with a basic reagent under suitable conditions to form a compound having the structure:

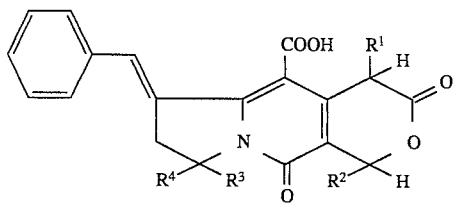

wherein $R^1$, $R^2$, $R^3$ and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) ozonolyzing the compound formed by step (a) under suitable conditions to form a compound having the structure:

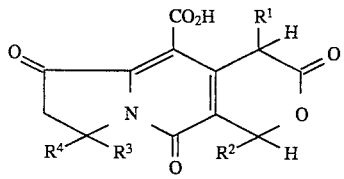

wherein $R^1$, $R^2$, $R^3$, and $R^4$ are independently the same or different and are H, or a linear or branched chain alkyl, alkylaryl, or hydroxyalkyl group, or an aryl group; and (c) re-esterifying the compound formed in step (b) with a suitable reagent under suitable conditions to form a compound having the structure:

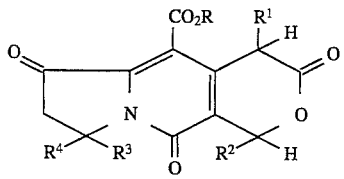

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group.

The invention also provides a process of synthesizing a compound having the structure:

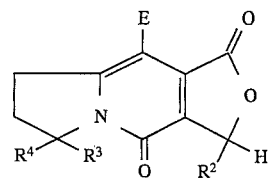

wherein E is H, $CO_2R$, $CONH_2$, CONHR, $CONR_2$, or CN; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9, which comprises:

(a) preparing a compound having the structure:

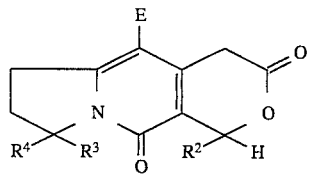

wherein E is H, $CO_2R$, $CONH_2$, CONHR, $CONR_2$, or CN; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9;

(b) treating the compound formed in step (a) with a hydroxylating reagent under suitable conditions to form compound having the structure:

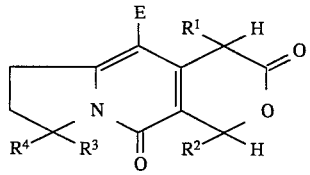

wherein E is H, $CO_2R$, $CONH_2$, CONHR, $CONR_2$, or CN; $R^1$ is OH; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and, n is an integer from 0 to 9; and (c) oxidizing the compound formed in step (b) with an oxidant under suitable conditions to form the compound having the structure:

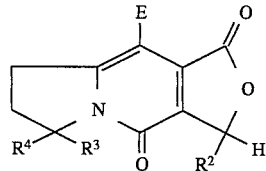

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group.

The invention further provides a process of synthesizing a compound having the structure:

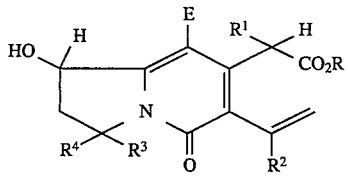

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group, which comprises:

(a) preparing a compound having the structure:

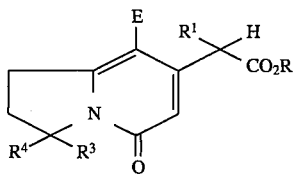

wherein E is H, CO₂R, CONH₂, CONHR, CONR₂, or CN; R¹, R³, and R⁴ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(b) reacting the compound formed in step (a) with a halogenating reagent to form a compound having the structure:

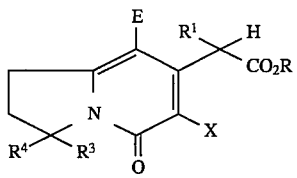

wherein X is Br, Cl, or I; E is H, CO₂R, CONH₂, CONHR, CONR₂, or CN; R¹, R³, and R⁴ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(c) cross-coupling the compound formed in step (b) with an organometallic reagent having the structure:

wherein M is a trialkylstannyl moiety and R² is H, or a linear or branched chain alkyl, alkylaryl, or hydroxyalkyl group, or an aryl group, under suitable conditions to form a compound having the structure:

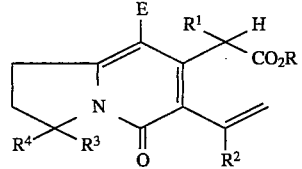

wherein E is H CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group; and (d) treating the compound formed in step (c) with a base and a hydroxylating reagent under suitable conditions to form a compound having the structure:

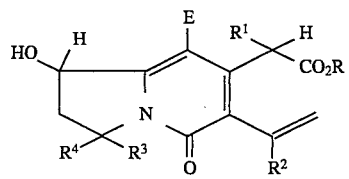

wherein E is H, CO₂R CONH₂, CONHR, CONR₂, or CN; R¹ R², R³, and R⁴ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group.

The invention further provides a process of synthesizing a compound having the structure:

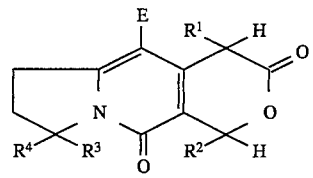

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group, which comprises:

(a) preparing a compound having the structure:

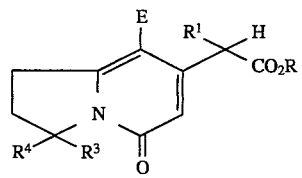

wherein E is H, CO₂R, CONH₂, CONHR, CONR₂, or CN; R¹, R³, and R⁴ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group;

(b) treating the compound formed in step (a) with a basic reagent under suitable conditions to form a compound having the structure:

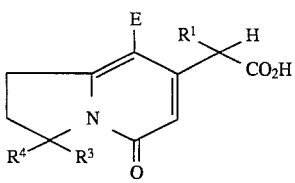

wherein E is H, CO₂R, CONH₂, CONHR, CONR₂, or CN; R is H, or a linear or branched chain alkyl, alkylaryl, or hydroxyalkyl group, or an aryl group; $R^1$, $R^3$, and $R^4$ are independently the same or different and are H, or a linear or branched chain alkyl, alkylaryl, or hydroxyalkyl group, or an aryl group; and (c) condensing the compound formed in step (b) with an aldehyde $R^2$—CHO under suitable conditions to form a compound having the structure:

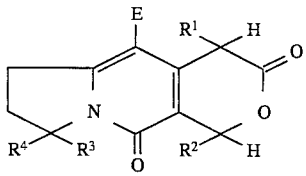

wherein E is H, CO₂R, CONH₂, CONHR, CONR₂, or CN; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group; and R is H, or a linear or branched chain alkyl, alkylaryl, or hydroxyalkyl group, or an aryl group.

The subject invention also provides a compound having the structure:

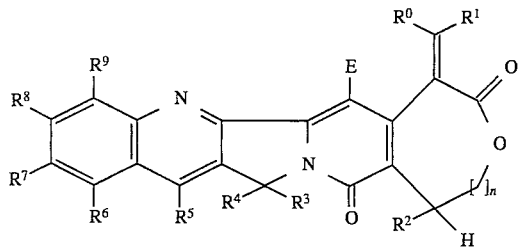

wherein E is H, CO₂R, CONH₂, CONHR, CONR₂, or CN; $R^0$ and $R^1$ are independently the same or different and are H, or a linear or branched alkyl, linear or branched alkylaryl, hydroxyalkyl or aryl group; $R^2$, $R^3$, and $R^4$ are independently the same or different and are H, or a linear or branched alkyl, linear or branched alkylaryl, hydroxyalkyl or aryl group; $R^5$, $R^6$, $R^7$, $R^8$ and $R^9$ are independently the same or different and are H, or a linear or branched alkyl, linear or branched alkylaryl or aryl group, or an alkoxy, aryloxy, hydroxyalkyl, C-glycal, nitro, cyano or aminoalkoxy group, or CO₂R, Cl, F, Br, I, $SR^{10}$, $NR^{11}R^{12}$ or $OR^{13}$; R is H, an alkyl, aryl, alkylaryl or hydroxyalkyl group; $R^{10}$, $R^{11}$ and $R^{12}$ are independently the same or different and are H, an alkyl, aryl, alkylaryl or acyl group; $R^{13}$ is glycosyl; and n is 0 or 1.

DETAILED DESCRIPTION OF THE INVENTION

The present invention provides new analogues of camptothecin, an anti-cancer compound having the structure:

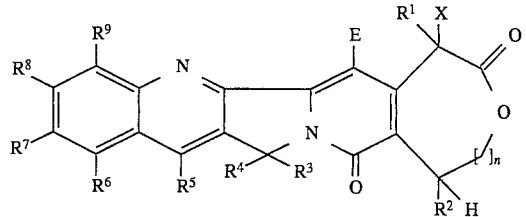

wherein E is H, CO₂R, CONH₂, CONHR, CONR₂, acyl, or CN; X, $R^1$ is O, or X is H or OH and $R^1$ is H, or a linear or branched chain alkyl, alkylaryl, or hydroxyalkyl group, or an aryl group; $R^2$, $R^3$, and $R^4$ are independently the same or different and are H, or a linear or branched chain alkyl, alkylaryl, or hydroxyalkyl group, or an aryl group; $R^5$, $R^6$, $R^7$ $R^8$ and $R^9$ are independently the same or different and are H, or a linear or branched chain alkyl, alkylaryl, alkoxy, hydroxyalkyl, or aminoalkoxy group, or an aryl or aryloxy group, or a C-glycal, or CO₂R, nitro, cyano, Cl, F, Br, I, $SR^{10}$ $NR^{11}R^{12}$, or $OR^{13}$; R is H, or a linear or branched chain alkyl, alkylaryl or hydroxyalkyl group, or an aryl group; $R^{10}$, $R^{11}$ and $R^{12}$ are independently the same or different and are H, or a linear or branched chain alkyl, alkylaryl, or acyl group, or an aryl group; $R^{13}$ is glycosyl; n is 0 or 1; with the proviso that when $R^1$ is ethyl and n is 0, E, $R^2$, $R^3$, and $R^4$ are not all H. In one embodiment of the invention, E is H; in another embodiment, E is CO₂R and R is preferably selected from the group consisting of methyl, ethyl, propyl, butyl, benzyl, and phenyl. In certain embodiments, $R^1$ is ethyl; while in certain other embodiments, $R^2$ is CH₃. In certain embodiments, X is preferably OH; while in still other embodiments, X is H.

The invention also provides a tricyclic intermediate useful for preparing camptothecin analogues, which has the structure:

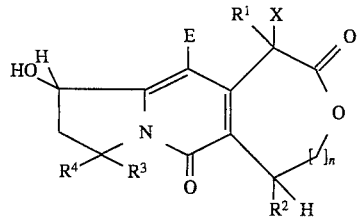

wherein g is H, CO₂R, CONH₂, CONHR, CONR₂, acyl, or CN; X is H, OH, or OR; $R^4$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, with the proviso that when $R^1$ is ethyl, and n is 0, E, $R^2$, $R^3$, and $R^4$ are not all H.

The invention further provides another intermediate useful for synthesizing camptothecin analogues having the structure:

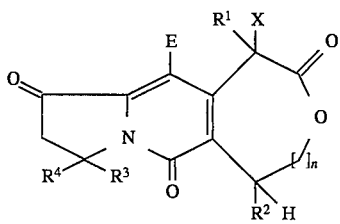

wherein E is H, $CO_2R$, $CONH_2$, CONHR, $CONR_2$, acyl, or CN; X is H OH, or OR; $R^1$, $R^2$, $R^3$ and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, with the proviso that when $R^1$ is ethyl, and n is O, E, $R^2$, $R^3$, and $R^4$ are not all H.

The invention provides a process of synthesizing the intermediate compound having the structure:

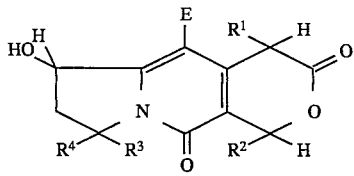

wherein E is H; X is OH; $R^1$, $R^2$, $R^3$, and $R^4$ are independently the same or different and are H, or a linear or branched chain alkyl, alkylaryl, or hydroxyalkyl group, or an aryl group; which comprises:

(a) treating the pyrrolidone having the structure:

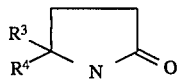

wherein $R^3$, and $R^4$ are independently the same or different and are H, or a linear or branched chain alkyl, alkylaryl, or hydroxyalkyl group, or an aryl group, with an alkylating agent under suitable conditions to form a compound having the structure:

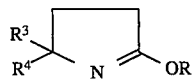

wherein $R^s$ and $R^4$ are independently the same or different and are H, or a linear or branched chain alkyl, alkylaryl, or hydroxyalkyl group, or an aryl group;

(b) condensing the compound formed by step (a) with Meldrum's acid in the presence of a base under conditions suitable to form a compound having the structure:

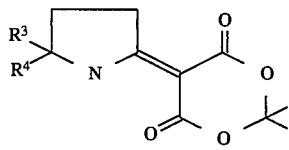

wherein $R^3$ and $R^4$ are independently the same or different and are H, or a linear or branched chain alkyl, alkylaryl, or hydroxyalkyl group, or an aryl group;

(c) treating the compound formed by step (b) with alkali alkoxide under conditions suitable to form a compound having the structure:

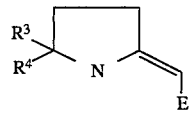

wherein $R^3$ and $R^4$ are independently the same or different and are H, or a linear or branched chain alkyl, or linear or branched alkylaryl, hydroxyalkyl, or aryl; and, E is $CO_2R$, $CONH_2$, CONHR, $CONR_2$, acyl, or CN; R is H, or a linear or branched chain alkyl, alkylaryl, or hydroxyalkyl group;

(d) reacting the compound formed by step (c) with a compound having the structure:

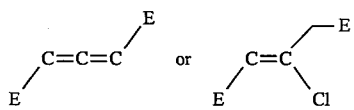

wherein E is $CO_2R$, $CONH_2$, CONHR, $CONR_2$, acyl, or CN; and, R is H, or a linear or branched chain alkyl, alkylaryl, or hydroxyalkyl group, under conditions suitable to form a compound having the structure:

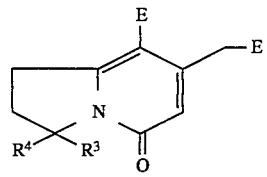

wherein $R^3$, and $R^4$ are independently the same or different and are H, or a linear or branched chain alkyl, alkylaryl, or hydroxyalkyl group, or an aryl group; E is $CO_2R$, $CONH_2$, CONHR, $CONR_2$, acyl, or CN; and, R is H, or a linear or branched chain alkyl, alkylaryl, or hydroxyalkyl group;

(e) deprotonating the compound formed by step (d) with a non-nucleophilic base to form an anion and alkylating the anion with an electrophilic reactant under conditions suitable to form a compound having the structure:

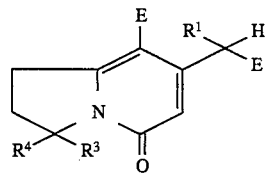

wherein E is $CO_2R$, $CONH_2$, CONHR, $CONR_2$, acyl or CN; $R^1$, $R^3$, and $R^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group;

(f) reacting the compound formed by step (e) with a carbonyl compound having the structure $R^2$—CHO, wherein $R^2$ is H, or a linear or branched chain alkyl, alkylaryl, or hydroxyalkyl group, or an aryl group, under suitable conditions to form a compound having the structure:

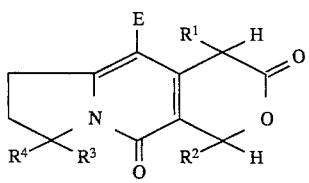

wherein E is $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group;

(g) hydrolyzing and decarboxylating the compound formed by step (f) under suitable acidic conditions to form a compound having the structure:

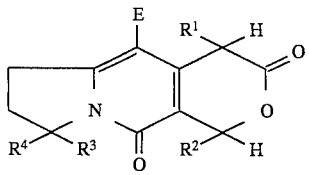

wherein E is H; $R^1$, $R^2$, $R^3$, and $R^4$ are independently the same or different and are H, or a linear or branched chain alkyl, alkylaryl, or hydroxyalkyl group, or an aryl group;

(h) treating the compound formed by step (g) with an hydroxylating reagent under conditions suitable to form the compound having the structure:

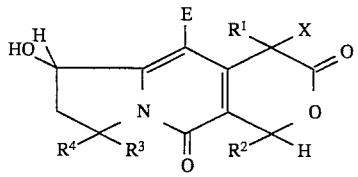

wherein E is H; X is OH; $R^1$, $R^2$, $R^3$, and $R^4$ are independently the same or different and are H, or a linear or branched chain alkyl, alkylaryl, or hydroxyalkyl group, or aryl. The process of step (a) above may be effected using a variety of alkylating reagents, known to those skilled in the art, but is preferably dimethyl sulfate. The process of step (b) results on heating the lactim ether with an active methylene condensing agent, preferably Meldrum's acid, in the presence of a tertiary amine base in an inert solvent such as benzene, at a temperature sufficient to cause reaction, preferably at the reflux temperature.

The condensation product is then converted in process step (c) to the unsaturated decarboxylated product by heating the product of step (b) with an alkali metal alkoxide or aryloxide in its corresponding alcohol as solvent or cosolvent at a temperature sufficient to cause reaction, preferably at the reflux temperature of the solvent. Process step (d) may be effected by treating the decarboxylated product with a disubstituted allene in the presence of a tertiary organic base, preferably triethylamine, in an alcoholic solvent, preferably absolute ethanol, at a temperature sufficient to cause reaction, preferably at room temperature. The reaction takes from 40 to 80 hours, and most usually about 65 hours.

The resulting pyridone is deprotonated in step (e) using a non-nucleophilic base, preferably potassium t-butoxide, in an anhydrous dipolar solvent, such as dimethoxyethane, at a temperature adequate to cause reaction, but low enough to prevent side-reactions, preferably at −78° C. The resulting deprotonated species is then alkylated or arylated with an electrophilic reagent, most commonly an alkyl halide, tosylate, or aryne intermediate, but preferably a primary or secondary alkyl bromide or iodide, and may be driven to completion by warming the reaction mixture to room temperature and stirring for a time depending on the specific alkylating agent, but usually between 2 and 50 hours.

Step (f) entails heating the alkylated heterocyclic compound with an alkyl or aryl aldehyde in the presence of an acid catalyst, preferably an organic sulfonic acid or a mineral acid, more preferably concentrated sulfuric acid, in a solvent inert to the reaction conditions, preferably aqueous dioxane. The reaction is preferably carried out in a thick wall tube or other high-pressure reaction vessel, at a temperature sufficient to cause reaction, generally between 90° C. and 160° C., and preferably at 107° C., for about 24 hours.

The process of step (g) may be effected by heating a mixture of the lactone formed in step (f) in a mineral acid, preferably concentrated aqueous hydrobromic acid, at a temperature sufficient to produce the desired product, generally between preferably between 90° C. and 140° C., and more preferably at 105° C., for about 18 hours.

The process of hydroxylating step (h) is accomplished by heating a mixture of the product of step (g) in a solvent inert to the reaction conditions, such as aqueous dioxane, with an hydroxylating reagent, preferably selenium dioxide, at a temperature sufficient to cause reaction, but not to degrade the starting material, preferably between 120° C. and 180° C., more preferably at 155° C.

The invention also provides a process of synthesizing the intermediate compound having the structure:

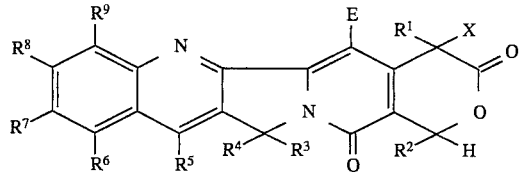

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl or hydroxyalkyl group, or an aryl group; $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

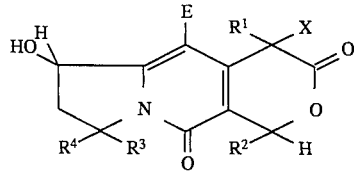

wherein E is H; X is OH; and, $R^4$, $R^2$, $R^3$, and $R^4$ are independently the same or different and are H, or a linear or branched chain alkyl, alkylaryl, or hydroxyalkyl group, or an aryl group, as described above;

(b) oxidizing the compound formed in step (a) with an oxidant under suitable conditions to form a compound having the structure:

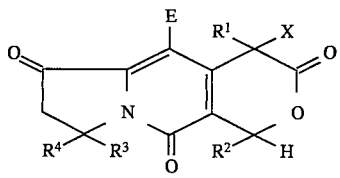

wherein E is H; X is OH; $R^1$, $R^2$, $R^3$, and $R^4$ are independently the same or different and are H, or a linear or branched chain alkyl, alkylaryl, or hydroxyalkyl group, or an aryl group;

(c) condensing the compound formed by step (b) with a compound having structure:

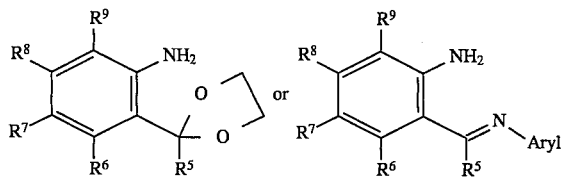

wherein $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, under suitable conditions to form the compound having the structure:

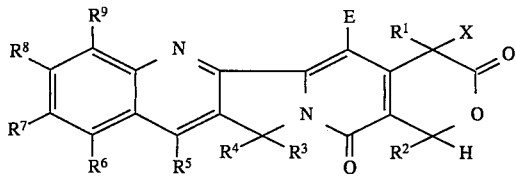

wherein E is H; X is OH; $R^1$, $R^2$, $R^3$, and $R^4$ are independently tile same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl or hydroxyalkyl group or an aryl group; $R^{10}$ $R^{11}$ and $R^{12}$ are independently the same or different and are H, or a linear or branched chain alkyl, alkylaryl, or acyl group, or an aryl group.

The invention provides a process of synthesizing substituted analogues of camptothecin, a compound having the structure:

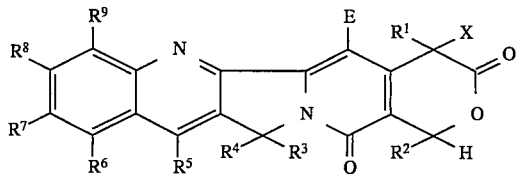

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, a linear or branched chain alkyl, alkylaryl, or acyl group, or an aryl group, which comprises:

(a) preparing a compound having the structure:

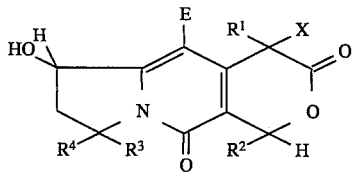

wherein E is H; X is OH; and, $R^1$, $R^2$, $R^3$, and $R^4$ are independently the same or different and are H, or a linear or branched chain alkyl, alkylaryl, or hydroxyalkyl group, or an aryl group, as described above;

(b) oxidizing the compound formed in step (a) with an oxidant under suitable conditions to form a compound having the structure:

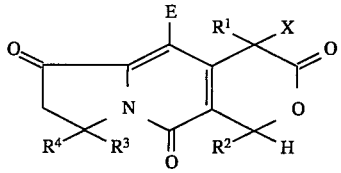

wherein E is H; X is OH; $R^1$, $R^2$, $R^3$, and $R^4$ are independently the same or different and are H, or a linear or branched chain alkyl, alkylaryl, or hydroxyalkyl group, or an aryl group;

(c) condensing the compound formed by step (b) with a compound having structure:

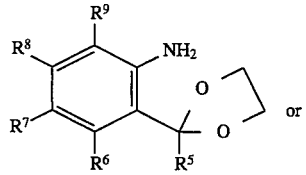

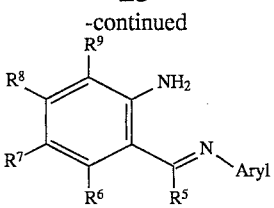

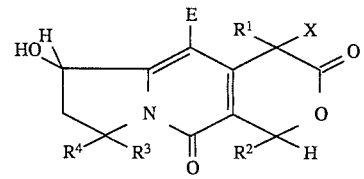

wherein $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$ or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, a linear or branched chain alkyl, alkylaryl, or acyl group, or an aryl group, under suitable conditions to form the compound having the structure:

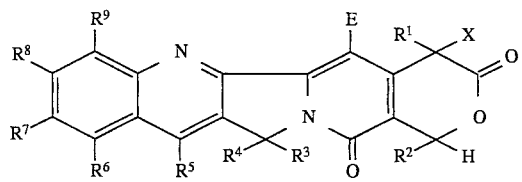

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkyl group, or an aryl aryloxy group or nitro, cyano, Cl, F, Br, I $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group. The process of step (b) is best performed using the oxidant pyridinium dichromate in the presence of activated powdered 4 Å molecular sieves in an inert solvent such as methylene dichloride at a temperature sufficient to result in the desired reaction, usually between −20° C. and 40° C., but preferably about 0° C. The condensation of step (c) is carried out by mixing the tricyclic ketone generated by step (a) with a protected ortho-amino aldehyde or ketone in an inert solvent, such as benzene or toluene, and heating to the reflux temperature of the solvent in the presence of an acid or basic catalyst. Acidic catalysts include mineral acids, such as sulfuric acid, nitric acid, phosphoric acid, and hydrochloric acid, organic alkanoic and sulfonic acids, such as acetic acid or propionic acid. The preferred catalyst is a mild acid, such as toluenesulfonic acid. A large variety of ortho-amino aldehydes and ketones are available from commercial sources, allowing the prepration of many substitution patterns, while other ortho-amino aldehydes and ketones can be prepared by methods well-known in the art. The reaction is carried out in a solvent inert to the reaction. Aromatic solvents are particularly well suited to the purpose, including benzene and toluene. When the solvent is not miscible with water, the reaction is best effected by azeotropic trapping of water generated in the process.

The invention also provides a process of synthesizing intermediates useful for preparing camptothecin analogues having the structure:

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, which comprises:

(a) preparing a compound having the structure:

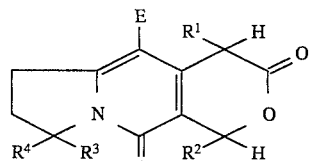

wherein E is $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above; and (b) treating the compound formed in step (a) with an hydroxylating reagent under suitable conditions to form the compound having the structure:

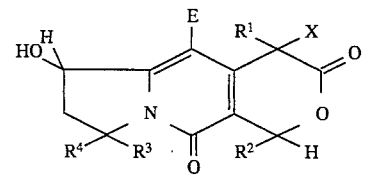

wherein E is $CO_2R$, $CONH_2$, CONHR, $CONR_2$, acyl, or CN; X is OH; $R^1$, $R^4$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group. The process of the preparing step (a) is carried out as described above. The process of the treating step (b) may be accomplished by heating a mixture of the product of preparing step (a) in a solvent inert to the reaction conditions, such as aqueous dioxane, with an hydroxylating reagent, preferably selenium dioxide, at a temperature sufficient to cause reaction, but not to degrade the starting material preferably between 120° C. and 180° C. more preferably at 155° C.

The invention also provides a process of synthesizing tricyclic intermediates useful for preparing camptothecin analogues. The intermediates have the structure:

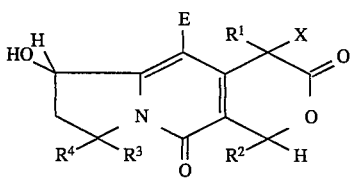

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, which comprises:

(a) preparing a compound having the structure:

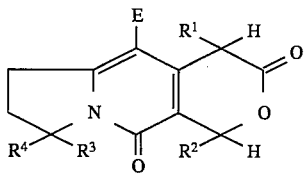

wherein E is $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, as described above; and, (b) treating the compound formed in step (a) with an hydroxylating reagent under suitable conditions to form the compound having the structure:

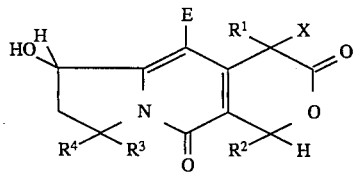

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; and, R is H, a linear or branched chain alkyl, alkylaryl, or hydroxyalkyl group, or an aryl group.

The invention provides another variant process of synthesizing camptothecin analgues having the structure:

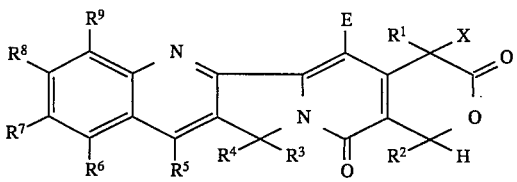

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, a linear or branched chain alkyl, alkylaryl, or acyl group, or an aryl group, which comprises:

(a) preparing a compound having the structure:

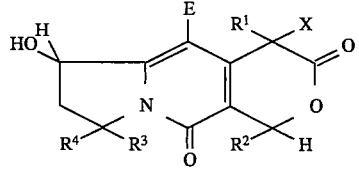

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above;

(b) oxidizing the compound formed in step (a) with an oxidant under suitable conditions to provide a compound having the structure:

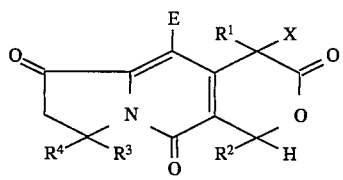

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group; and (c) condensing the compound formed by step (d) with a compound having structure:

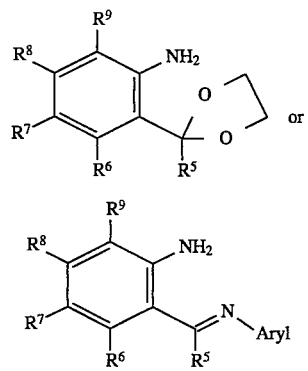

wherein $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, under suitable conditions to form the compound having the structure:

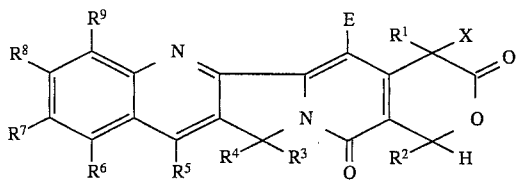

wherein E is $CO_2R$, $CONH_2$, CONHR, $CONR_2$, acyl, or CN; X is OH: $R^1$, $R^2$, $R^3$, and $R^4$ are independently the same or different and are H, or a linear or branched chain alkyl, alkylaryl, or hydroxyalkyl group or an aryl group $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano Cl, F, Br, I, $SR^{10}$, or $N^{11}R^{12}$; is H, or a linear or branched chain alkyl alkylaryl or hydroxyalkyl group; and $R^{10}$, $R^{11}$ and $R^{12}$ are independently the same or different and are H, a linear or branched chain alkyl, alkylaryl, or acyl group, or an aryl group. The process of the oxidizing step (b) is best effected using pyridinium dichromate in the presence of powdered 4 Å molecular sieves in an inert solvent such as methylene dichloride at 0°–5° C.

The invention further provides a process of synthesizing a compound having the structure:

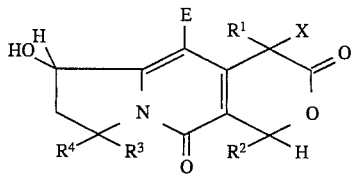

wherein E is H, $CO_2R$, $CONH_2$, CONHR, $CONR_2$, acyl, or CN; X is H or OH; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, which comprises:

(a) preparing a compound having the structure:

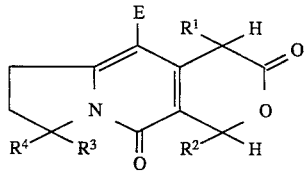

wherein E is H, $CO_2R$, $CONH_2$, CONHR, $CONR_2$ acyl, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described. above; and (b) treating the compound formed in step (a) with an hydroxylating agent comprising potassium hexamethyldisilamide and a reagent having the structure:

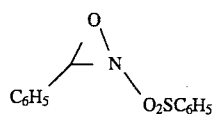

under suitable conditions to form the compound having the structure:

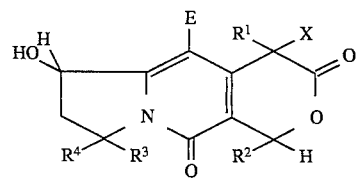

wherein E is H, $CO_2R$, $CONH_2$, CONHR, $CONR_2$, acyl, or CN; X is H or OH; $R^1$, $R^2$, $R^3$, and $R^4$ are independently the same or different and are H, or a linear or branched chain alkyl, alkylaryl, or hydroxyalkyl group, or an aryl group; R is H a linear or branched chain alkyl alkylaryl, or hydroxyalkyl group, or arm aryl group.

The invention also provides a process of synthesizing a compound having the structure:

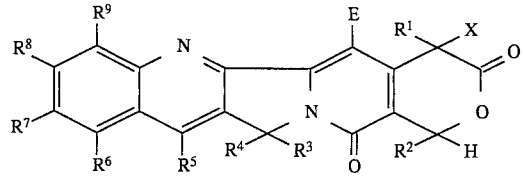

wherein E is H, $CO_2R$, CONHa, CONHR, $CONR_2$, acyl, or CN; X is H; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$ $R^8$ and $R^9$ are independently the same or different and are H, or a linear or branched chain alkyl, alkylaryl, alkoxy, hydroxyalkyl, or aminoalkoxy group, or an aryl or aryloxy, group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, a linear or branched chain alkyl, alkylaryl, or acyl group, or an aryl group, which comprises:

(a) preparing a compound having the structure:

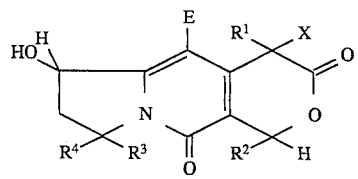

wherein E is H, $CO_2R$, $CONH_2$, CONHR, $CONR_2$, acyl, or CN; X is H; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above;

(b) oxidizing the compound formed in step (a) under suitable conditions with an oxidant to provide a compound having the structure:

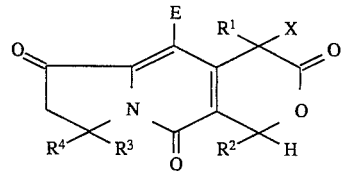

wherein E is H, $CO_2R$, $CONH_2$, CONHR, $CONR_2$, acyl, or CN; X is H; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group; and (c) condensing the compound formed by step (b) with a compound having structure:

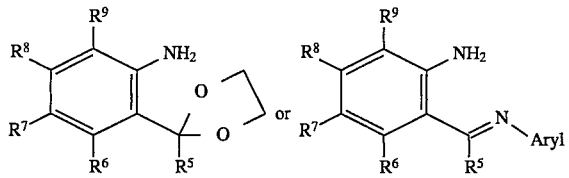

wherein $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, a linear or branched chain alkyl, alkylaryl, or acyl group, or an aryl group, under suitable conditions to form the compound having the structure:

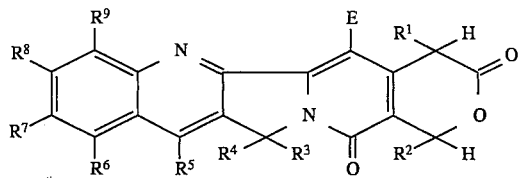

wherein E is H $CO_2R$, $CONH_2$, CONHR, $CONR_2$, acyl or CN; $R^1$, $R^2$, $R^3$, and $R^4$ are independently the same or different and are H, or a linear or branched chain alkyl, alkylaryl or hydroxyalkyl group or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$ cyano Cl, F, Br, I, $SR^{10}$ or $NR^{11}R^{12}$; R is H or a linear or branched chain alkyl, alkylaryl, or hydroxyalkyl group; and $R^{10}$, $R^{11}$ and $R^{12}$ are independently the same or different and are H, a linear or branched chain aryl, alkylaryl, or acyl group, or an aryl group.

The invention provides a process of synthesizing a compound having the structure:

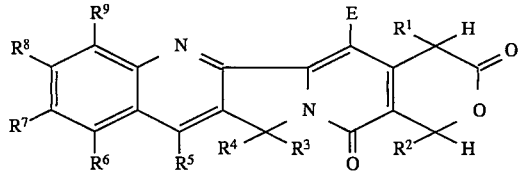

wherein E is H; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$ and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, a linear or branched chain alkyl, alkylaryl, or acyl group, or an aryl group, which comprises:

(a) preparing a compound having the structure:

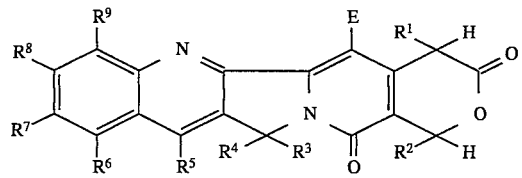

wherein E is H, $CO_2R$, CONHZ, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above;

(b) hydrolyzing and decarboxylating the compound formed in step (a) under suitable conditions with an acid to provide a compound having the structure:

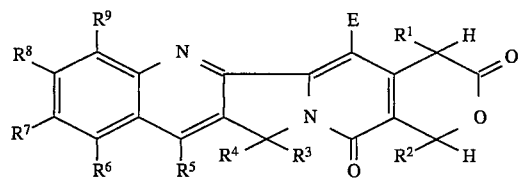

wherein E is H; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$ or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, linear or branched chain alkyl, alkylaryl, or acyl group, or an aryl group.

The process of the hydrolyzing and decarboxylating step (b) is accomplished by mixing the product of the preparing step (a) with an acid, preferably an aqueous mineral acid, especially hydrobromic acid, in a sealed tube or high-pressure reaction vessel, and heating at a temperature between 100° C. and 180° C., preferably at 140° C., for 10 to 24 hours, preferably for 15 hours.

The invention also provides a process of synthesizing a compound having the structure:

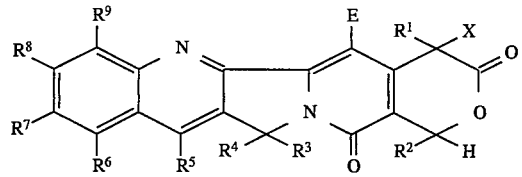

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or linear or branched chain alkyl, alkylaryl, or acyl group, or an aryl group, which comprises:

(a) preparing a compound having the structure:

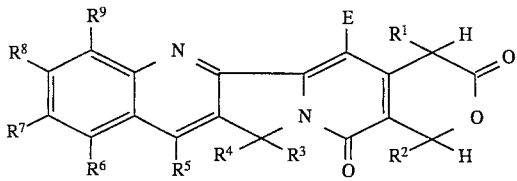

wherein E is H; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$ $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group, as described above;

(b) treating the compound formed in step (a) with a hydroxylating reagent under suitable conditions to form a compound having the structure:

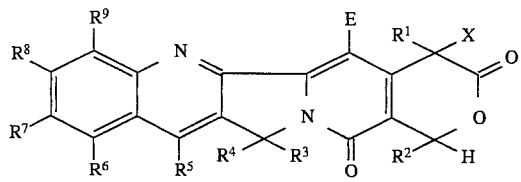

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group, The treating step (b) is effected by dissolving the product of the preparing step (a) in a dipolar solvent, preferably dimethylformamide, and then adding a hydroxylating reagent containing a divalent ionic metal halide, preferably cupric chloride, and a base, preferably an organic base, such as dimethylamine, and then bubbling in oxygen gas over a period of time sufficient to cause completion of the process, typically about seven hours.

The invention further encompasses a process of synthesizing a compound having the structure:

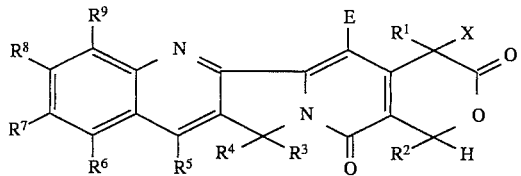

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$ or $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

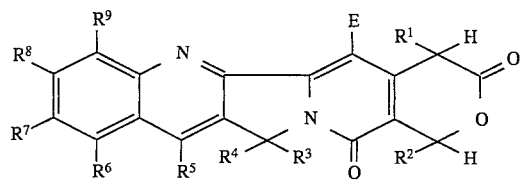

wherein E is $CO_2R$, $CONH_2$, CONHR, $CONR_2$, acyl, or CN; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, as described above;

(b) treating the compound formed in step (a) with a hydroxylating reagent under suitable conditions to form a compound having the structure:

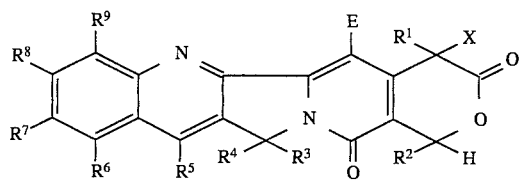

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group. The hydroxylating reagent of the treating step (b) preferably comprises oxygen, cupric halide, and a base.

The invention also includes a process of synthesizing a compound having the structure:

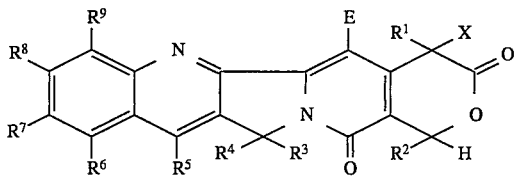

wherein E is H; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

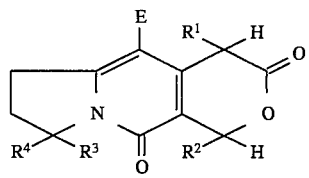

wherein E is H; $R^1$, $R^2$, $R^3$, and $R^4$ are independently the same or different and are H, or a linear or branched chain alkyl, alkylaryl, or hydroxyalkyl group, or an aryl group, as described above;

(b) treating the compound formed in step (a) with a hydroxylating reagent under conditions suitable to form the compound having the structure:

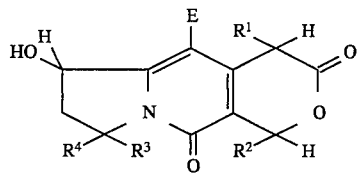

wherein E is H; $R^1$, $R^2$, $R^3$, and $R^4$ are independently the same or different and are H, or a linear or branched chain alkyl, alkylaryl, or hydroxyalkyl group, or an aryl group;

(c) oxidizing the compound formed in step (b) with an oxidant under suitable conditions to form the compound having structure:

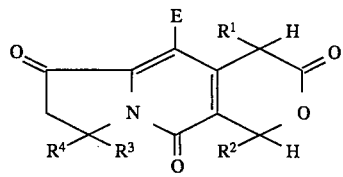

wherein E is H; $R^1$, $R^2$, $R^3$, and $R^4$ are independently the same or different and are H, or a linear or branched chain alkyl, alkylaryl, or hydroxyalkyl group, or an aryl group;

(d) condensing the compound formed in step (c) with a compound having structure:

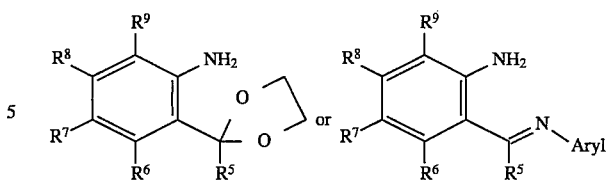

wherein $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group, under suitable conditions to form a compound having the structure:

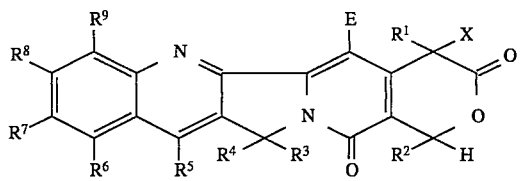

wherein E is H; X is H; $R^1$, $R^2$, $R^3$, and $R^4$ are independently the same or different and are H, or a linear or branched chain alkyl, alkylaryl, or hydroxyalkyl group or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group or nitro $CO_2R$, cyano Cl, F, Br, I, $SR^{10}$, $NR^{11}R^{12}$; R is H, or a linear or branched chain alkyl, alkylaryl, or hydroxyalkyl group or an aryl group; and $R^{10}$, $R^{11}$ and $R^{12}$ are independently the same or different and are H, or a linear or branched chain alkyl, alkylaryl, or acyl group, or an aryl group, under suitable conditions to form the compound having the structure:

(e) treating the compound formed in step (d) with a hydroxylating reagent under suitable conditions to form the compound having the structure:

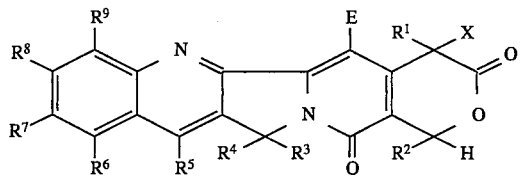

wherein E is H; X is OH; $R^1$, $R^2$, $R^3$, and $R^4$ are independently the same or different. and are H, or a linear or branched chain alkyl, alkylaryl, or hydroxyalkyl group or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano Cl, F, Br, I, $SR^{10}$, $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group. In one embodiment of the invention, the hydroxylating reagent of the treating step (b) comprises potassium hexamethyldisilamide and a reagent having the structure:

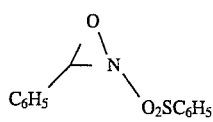

The invention also includes a process of synthesizing a compound having the structure:

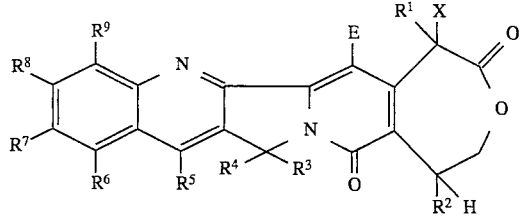

wherein E is $CO_2R$, $CONH_2$, CONHR, $CONR_2$, acyl, or CN; X is OH; $R^1$, $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

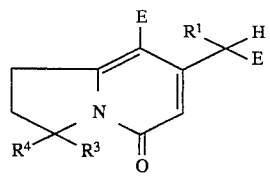

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, as described above;

(b) halogenating the compound formed in step (a) with a halogenating agent, selected from the group comprising bromine, chlorine, and iodine under suitable conditions to form a compound having the structure:

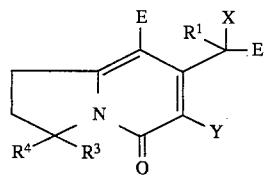

wherein E is $CO_2R$, $CONH_2$, CONHR, $CONR_2$, acyl, or CN; X is H; Y is Br, Cl, or I; $R^1$, $R^3$, and $R^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group;

(c) treating the compound formed in step (b) with alkyl- or arylallyltrialkylstannane and a catalyst comprising palladium(O) under suitable conditions to form a compound having the structure:

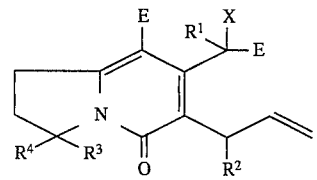

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group or an aryl group; R is H, or a linear or branched chain alkyl, alkylaryl, or hydroxyalkyl group;

(d) reacting the compound formed in step (c) with alkali metal periodate or ozone and a reducing agent comprising alkali metal borohydride, wherein the alkali metal is either lithium, sodium, or potassium, under suitable conditions to form a compound having the structure:

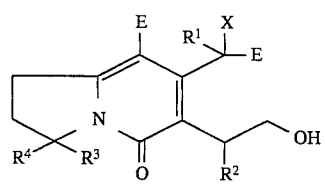

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; R is H, or a linear or branched chain alkyl, alkylaryl, or hydroxyalkyl group;

(e) lactonizing the compound formed in step (d) with a condensing reagent, comprising potassium trimethylsilyloxide followed by a dehydrating agent comprising N,N-dicyclohexylcarbodiimide and N,N-dimethylaminopyridine, under suitable conditions to form a compound having the structure:

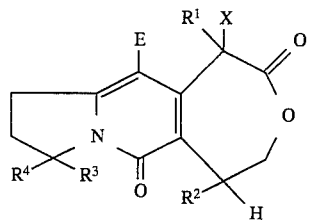

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; R is H, or a linear or branched chain alkyl, alkylaryl, or hydroxyalkyl group;

(f) hydroxylating the compound formed in step (e) with an hydroxylating reagent comprising the oxaziridine having the structure:

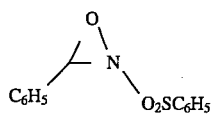

under suitable conditions to form a compound having the structure:

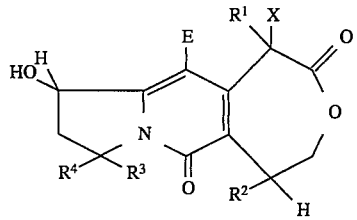

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; R is H, or a linear or branched chain alkyl, alkylaryl, or hydroxyalkyl group;

(g) oxidizing the compound formed in step (f) with an oxidant under suitable conditions to form a compound having the structure:

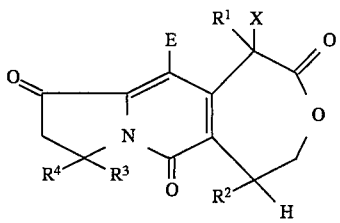

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; R is H, or a linear or branched chain alkyl, alkylaryl, or hydroxyalkyl group;

(h) condensing the compound formed in step (g) under suitable conditions to form a compound having the structure:

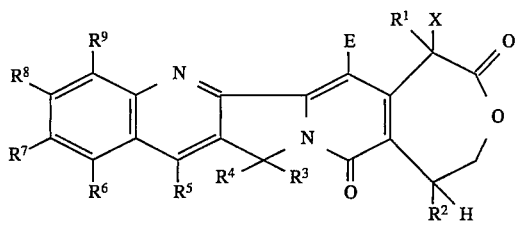

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxya.lkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group;

(i) hydroxylating the compound formed in step (h) with a hydroxylating reagent under suitable conditions to form a compound having the structure:

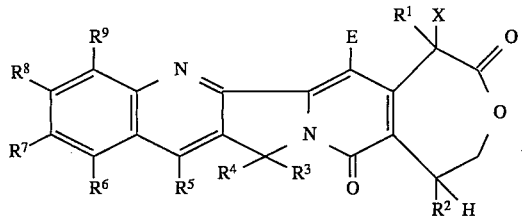

wherein E is $CO_2R$, $CONH_2$, CONHR, $CONR_2$, acyl, or CN; X is OH; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group. The oxidant of the oxidizing step (g) is favorably pyridinium dichromate. The hydroxylating reagent of step (j) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention further provides a process of synthesizing a compound, having the structure:

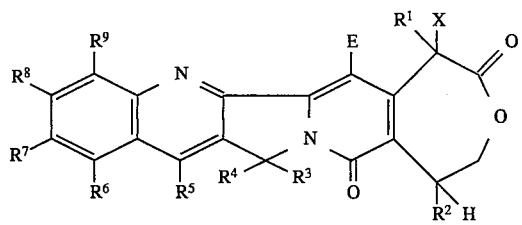

wherein E is H; X is OH; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group, which comprises:

(a) preparing a compound having the structure:

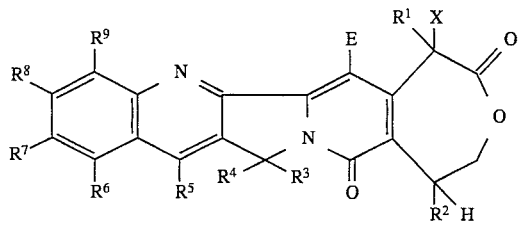

wherein E is $CO_2R$, $CONH_2$, CONHR, $CONR_2$, acyl, or CN; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$ $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group, as described above;

(b) hydrolyzing and decarboxylating the compound formed in step (a) with an acid comprising aqueous hydrobromic acid under suitable conditions to form a compound having the structure:

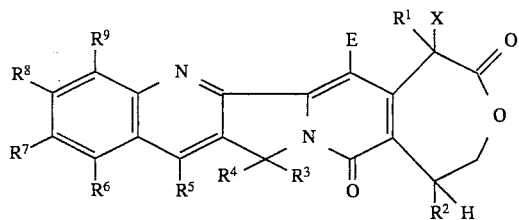

wherein E is H; X is H; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br I $SR^{10}$, $NR^{11}R^{12}$; R is H, or a linear or branched chain alkyl, alkylaryl, or hydroxyalkyl group, or an aryl group; and $R^{10}$, $R^{11}$ and $R^{12}$ are independently the same or different and are H, or a linear or branched chain alkyl, alkylaryl, or acyl group, or an aryl group; and (c) hydroxylating the compound formed in step (b) with a hydroxylating reagent under suitable conditions to form a compound having the structure:

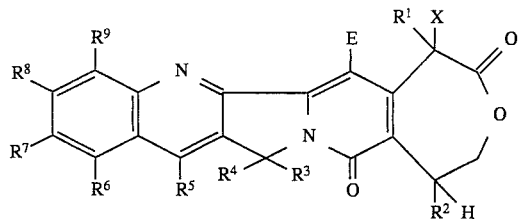

wherein E is H; X is OH; $R^1$, $R^3$, and $R^4$ are independently the same or different and are H, or a linear or branched chain alkyl, alkylaryl, or hydroxyalkyl group, or an aryl group; $R^2$ is a linear or branched chain alkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, $NR^{11}R^{12}$; R is H, or a linear or branched chain alkyl, alkylaryl, or hydroxyalkyl group or an aryl group; and $R^{10}$, $R^{11}$ and $R^{12}$ are independently the same or different and are H, or a linear or branched chain alkyl, alkylaryl, or acyl group, or an aryl group.

The hydroxylating reagent of step (c) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention provides a process of synthesizing a compound having the structure:

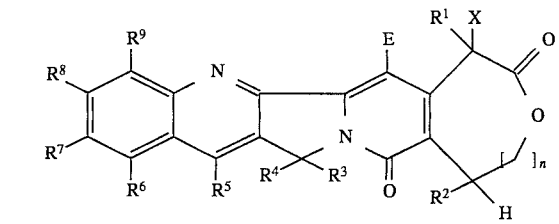

wherein E is H, $CO_2R$, $CONH_2$, CONHR, $CONR_2$, acyl, or CN; X, $R^1$ is O; $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; and n is 0 or 1, which comprises:

(a) preparing a compound having the structure:

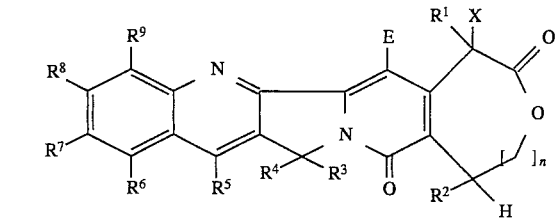

wherein $R^1$ is H; E is H, $CO_2R$, $CONH_2$, CONHR, $CONR_2$, acyl, or CN; X is H; $R^2$, $R^3$, and $R^4$ are independently the same or different and are H, or a linear or branched chain alkyl, alkylaryl, or hydroxyalkyl group, or an aryl group; $R^5$, $R^6$, $R^7$, $R^8$, and $R^9$ are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$ or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; and n is 0 or 1, as described above;

(b) hydroxylating the compound formed in step (a) with a hydroxylating reagent under suitable conditions to form a compound having the structure:

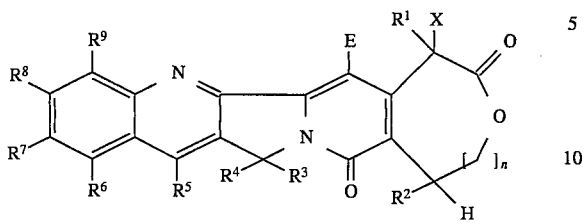

wherein E is H, CO$_2$R, CONH$_2$, CONHR, CONR$_2$, acyl, or CN; X is OH; R$^1$ is H; R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl. group, or an aryl group; and n is 0 or 1; and, (c) oxidizing the compound formed in step (b) with an oxidant under suitable conditions to form a compound having the structure:

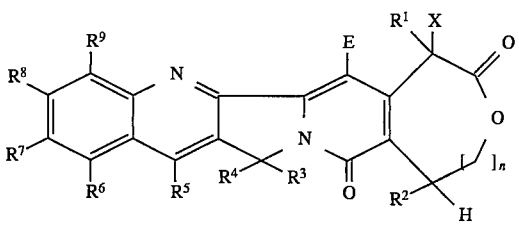

wherein E is H, CO$_2$R, CONH$_2$, CONHR, CONR$_2$, acyl, or CN; X, R$^1$ is O; R$^2$, R$^3$, and R$^4$ are independently the same or different and are H, or a linear or branched chain alkyl, alkylaryl, or hydroxyalkyl group, or an aryl group; R$^5$, R$^6$, R$^7$, R$^8$, and R$^9$ are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; and n is 0 or 1. The hydroxylating reagent of step (b) comprises oxygen and a divalent transition metal halide or carboxylate, wherein the divalent transition metal is copper(II), and the halide or carboxylate is selected from the group comprising fluoride, chloride, bromide, iodide, acetate, benzoate, or propionate.

The invention also encompasses a process of synthesizing enantiomerically pure compounds related to camptothecin and analogues thereof, wherein the configuration is exclusively R or S. The process comprises performing the hydroxylating step with the hydroxylating reagent having the structure:

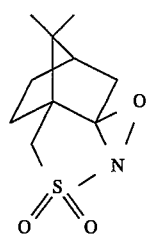

or the hydroxylating reagent of opposite configuration, respectively. While the value of the racemic mixture of camptothecins provided by non-enantiospecific routes is considerable, given the high native biological activity of camptothecin, the possibility of obtaining still higher activities in an optically pure analogue suggest the clinical importance of the present invention.

The invention also includes a process of synthesizing a compound having the structure:

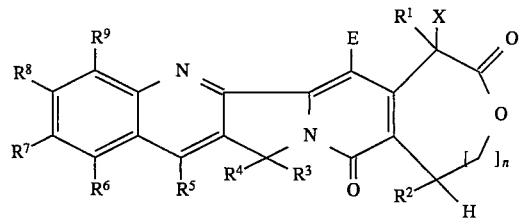

wherein E is H, CO$_2$R, CONH$_2$, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; one or more of the group R$^5$, R$^6$, R$^7$, R$^8$, and R$^9$ are C-glycal, and the others are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$ or NR$^{11}$R$^{12}$; R is H, or a linear or branched chain alkyl, alkylaryl, or hydroxyalkyl group, or an aryl group; R$^{10}$, R$^{11}$ and R$^{12}$ are independently the same or different and are H, or a linear or branched chain alkyl, alkylaryl, or acyl group, or an aryl group; and n is 0 or 1, which comprises:

(a) preparing a compound having the structure:

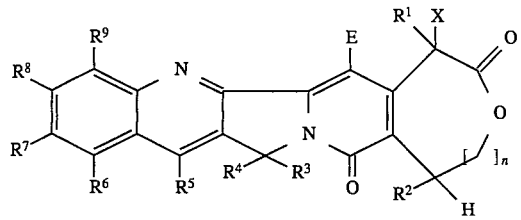

wherein E is H, CO$_2$R, CONH$_2$, CONHR, CONR$_2$, acyl, or CN; X, R$^1$ is O, or X is H or OH and R$^1$ is H, or a linear or branched chain alkyl, alkylaryl, or hydroxyalkyl group, or an aryl group; R$^2$, R$^3$, and R$^4$ are independently the same or different and are H, or a linear or branched chain alkyl, alkylaryl, or hydroxyalkyl group, or an aryl group; one or more of the group R$^5$, R$^6$, R$^7$, R$^8$, and R$^9$ are $^{OR}$13, and the others are independently the same or different and are H, or a linear or branched chain alkyl, alkylaryl, alkoxy, hydroxyalkyl, or aminoalkoxy group, or an aryl or aryloxy group, or nitro, CO$_2$R, cyano, Cl, F, Br, I, SR$^{10}$, or NR$^{11}$R$^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; $R^{13}$ is H; and n is 0 or 1, as described above;

(b) reacting the compound formed in step (a) with a reagent comprising $PhN(CF_3SO_2)_2$ under suitable conditions to form a triflate compound having the structure:

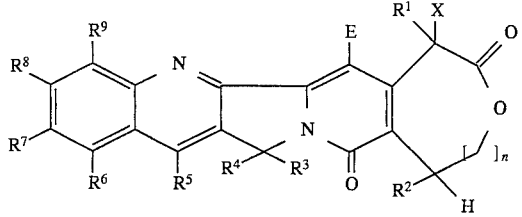

wherein E is H, $CO_2R$, $CONH_2$, CONHR, $CONR_2$, acyl, or CN; X, $R^1$ is O, or X is H or OH and $R^1$ is H, or a linear or branched chain alkyl, alkylaryl, or hydroxyalkyl group, or an aryl group; $R^2$, $R^3$, and $R^4$ are independently the same or different and are H, or a linear or branched chain alkyl, alkylaryl, or hydroxyalkyl group, or an aryl group; one or more of the group $R^5$, $R^6$, $R^7$, $R^8$ and $R^9$ are $OR^{13}$, and the others are independently the same or different and are H, or a linear or branched chain alkyl, alkylaryl, alkoxy, hydroxyalkyl, or aminoalkoxy group, or an aryl or aryloxy group, or nitro, cyano, $CO_2R$, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; $R^{13}$ is $SO_2CF_3$; and, n is 0 or 1; and (c) coupling the compound formed in reacting step (b) with a stannylated glycal under suitable conditions to form the compound having the structure:

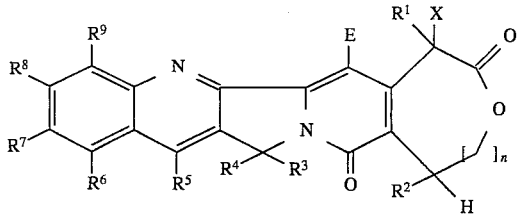

wherein E is H, $CO_2R$, $CONH_2$, CONHR, $CONR_2$, acyl, or CN; X, $R^1$ is O, or X is H or OH and $R^1$ is H, or a linear or branched chain alkyl, alkylaryl, or hydroxyalkyl group, or an aryl group; $R^2$, $R^3$, and $R^4$ are independently the same or different and are H, or a linear or branched chain alkyl, alkylaryl, or hydroxyalkyl group, or an aryl group; one or more of the group $R^5$, $R^6$, $R^7$, $R^8$, and $R^9$ are $OR^{13}$, and the others are independently the same or different and are H, or a linear or branched chain alkyl, alkylaryl, alkoxy, hydroxyalkyl, or aminoalkoxy group, or an aryl or aryloxy group, or nitro, cyano, $CO_2R$, Cl, F, Br, I, $SR^{10}$, or $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; $R^{13}$ is C-glycal; and n is 0 or 1.

The invention also provides a process of synthesizing a compound having the structure:

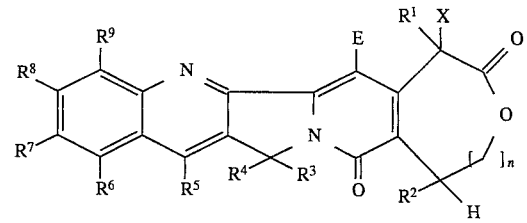

wherein E is H, $CO_2R$, $CONH_2$, CONHR, $CONR_2$, acyl, or CN; X, $R^1$ is O, or X is H or OH and $R^1$ is H, or a linear or branched chain alkyl, alkylaryl, or hydroxyalkyl group, or an aryl group; $R^2$, $R^3$, and $R^4$ are independently the same or different and are H, or a linear or branched chain alkyl, alkylaryl, or hydroxyalkyl group, or an aryl group; one or more of the group $R^5$, $R^6$, $R^7$, $R^8$, and $R^9$ are $OR^{13}$, and the others are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; $R^{13}$ is a O-glycosyl; and n is 0 or 1; which comprises:

(a) preparing a compound having the structure:

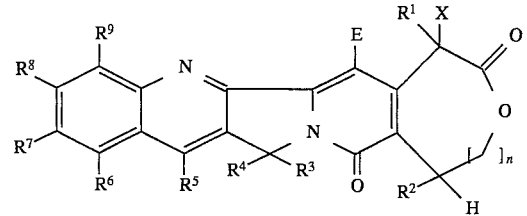

wherein E is H, $CO_2R$, $CONH_2$, CONHR, $CONR_2$, acyl, or CN; X, $R^1$ is O, or X is H or OH and $R^1$ is H, or a linear or branched chain alkyl, alkylaryl, or hydroxyalkyl group, or an aryl group; $R^2$, $R^3$, and $R^4$ are independently the same or different and are H, or a linear or branched chain alkyl, alkylaryl, or hydroxyalkyl group, or an aryl group; one or more of the group $R^5$, $R^6$, $R^7$, $R^8$, and $R^9$ are $OR^{13}$, and the others are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; $R^{13}$ is H; and, n is 0 or 1; as described above; and (b) reacting the compound formed in step (a) with a reagent comprising a glycosyl epoxide under suitable conditions to form a compound having the structure:

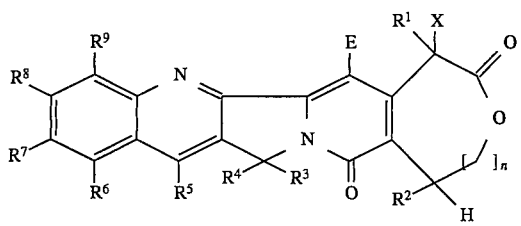

wherein E is H, $CO_2R$, $CONH_2$, CONHR, $CONR_2$, acyl, or CN; X, $R^1$ is O, or X is H or OH and $R^1$ is H, or a linear or branched chain alkyl, alkylaryl, or hydroxyalkyl group, or an aryl group; $R^2$, $R^3$, and $R^4$ are independently the same or different and are H, or a linear or branched chain alkyl, alkylaryl, or hydroxyalkyl group, or an aryl group; one or more of the group $R^5$, $R^6$, $R^7$, $R^8$, and $R^9$ are $OR^{13}$, and the others are independently the same or different and are H, or a linear or branched chain alkyl, alkylaryl, alkoxy, hydroxyalkyl, or aminoalkoxy group, or an aryl or aryloxy group, or nitro, $CO_2R$, cyano, Cl, F, Br, I, $SR^{10}$, $NR^{11}R^{12}$; R is H, or a linear or branched chain alkyl, alkylaryl, or hydroxyalkyl group, or an aryl group; $R^{10}$, $R^{11}$ and $R^{12}$ are independently the same or different and are H, or a linear or branched chain alkyl, alkylaryl, or acyl group, or an aryl group; $R^{13}$ is O-glycosyl; and n is 0 or 1.

The present invention provides synthetic processes for the preparation of camptothecin, an anti-cancer substance and analogues thereof. In one embodiment, the invention provides a process of synthesizing a compound having the structure:

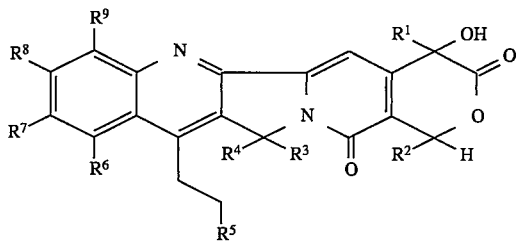

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9, which comprises:

(a) treating an arylaldehyde having the structure:

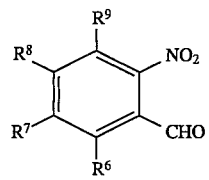

wherein $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$, is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9, with a vinylic organometallic reagent having the structure:

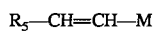

$R_5-CH=CH-M$ wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$, and M may be Li, K, Na, MgCl, and MgBr; to form a compound having the structure:

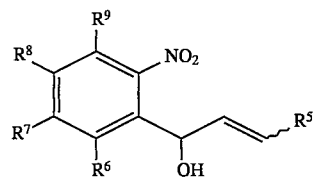

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOr^{11}$; and n is an integer from 0 to 9;

(b) oxidizing the compound formed in step (a) with an oxidizing agent selected from the group comprising $CrO_3$, $K_2CrO_4$, and pyridinium dichromate to form a compound having the structure:

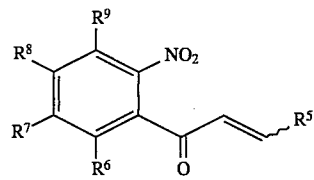

wherein $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^7$ is OH, or a linear or branched chain alkyl, alkoxy, alkylaryl, or alkylaryloxy group, or an aryl group; $R^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9;

(c) reducing the compound formed in step (b) with a hydrogenating reagent comprising H$_2$/PdC, diimide, Wilkinson's reagent, and boron hydrides to form a compound having the structure:

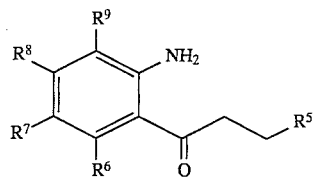

wherein R$^5$ is a linear or branched chain alkyl, alkylaryl, alkoxyalkyl, aryloxyalkyl, or hydroxyalkyl group, or an aryl group, or (CH$_2$)$_n$NR$^{11}$R$^{12}$, or (CH$_2$)$_n$OR$^{11}$; R$^6$, R$^8$, and R$^9$ are independently the same or different and are H, or a linear or branched chain alkyl, alkylaryl, alkoxy, aminoalkoxy, or hydroxyalkyl group, or an aryl or aryloxy group, or nitro, CO$_2$R, Cl, F, Br, I, or SR$^{10}$; R$^7$ is OH, or a linear or branched chain alkyl, alkoxy, alkylaryl, or alkylaryloxy group, or an aryl group; R$^{10}$ is H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9;

(d) condensing the compound formed in step (c) with a compound having the structure:

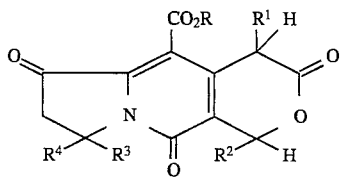

wherein E is H CO$_2$R, CONH$_2$, CONHR CONR$_2$, or CN; R$^1$, R$^2$, R$^3$, and R$^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group; in the presence of an acid catalyst selected from the group comprising p-toluenesulfonic acid, benzenesulfonic acid, sulfuric acid, and hydrochloric acid to form a compound having the structure:

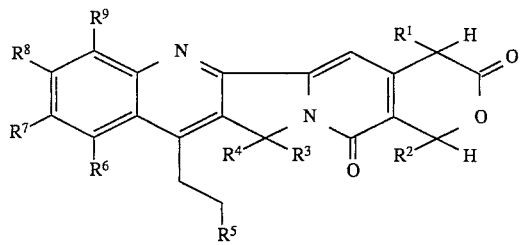

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; R$^5$ is a linear or branched chain alkyl, alkylaryl, alkoxyalkyl, aryloxyalkyl, or hydroxyalkyl group, or an aryl group, or (CH$_2$)$_n$NR$^{11}$R$^{12}$, or (CH$_2$)$_n$OR$^{11}$; R$^7$ is OH, or a linear or branched chain alkyl, alkoxy, alkylaryl, or alkylaryloxy group, or an aryl group; R$^6$, R$^8$ and R$^9$ are independently the same or different and are H, or a linear or branched chain alkyl, alkylaryl, alkoxy, aminoalkoxy, or hydroxyalkyl group, or an aryloxy group, or nitro, CO$_2$R, Cl, F, Br, I, or SR$^{10}$; R$^{10}$, R$^{11}$ and R$^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9;

(e) hydrolyzing and decarboxylating the compound formed in step (d) using an acid selected from the group comprising hydrobromic acid, hydrochloric acid, and p-tolulenesulfonic acid to form a compound having the structure:

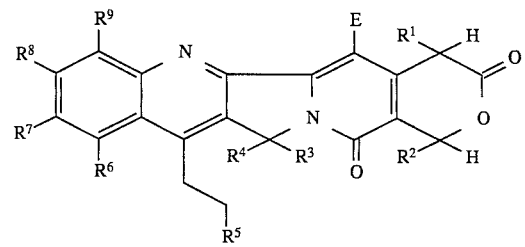

wherein R$^1$, R$^2$, R$^3$, and R$^4$ are independently the same or different and are H, or a linear or branched chain alkyl, alkylaryl, or hydroxyalkyl group, or an aryl group; R$^5$ is a linear or branched chain alkyl, alkylaryl, alkoxyalkyl, aryloxyalkyl, or hydroxyalkyl group, or an aryl group, or (CH$_2$)$_n$NR$^{11}$R$^{12}$, or (CH$_2$)$_n$OR$^{11}$; R$^7$ is OH or a linear or branched chain alkyl, alkoxy, alkylaryl, or alkylaryloxy group or an aryl group; R$^6$, R$^8$, and R$^9$ are independently the same or different and are H, or a linear or branched chain alkyl, alkylaryl, alkoxy, aminoalkoxy, or hydroxyalkyl group, or an aryl or aryloxy group, or nitro, CO$_2$R, Cl, F, Br, I, or SR$^{10}$; R$^{10}$, R$^{11}$ and R$^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9; and (f) treating the compound formed in step (e) with a hydroxylating reagent under suitable conditions to form a compound having the structure:

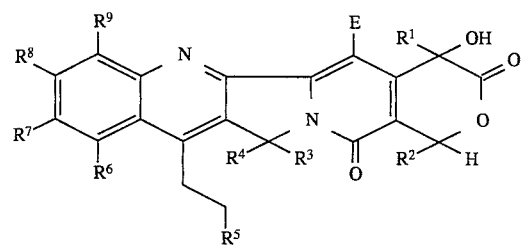

wherein R$^1$, R$^2$, R$^3$, and R$^4$ are independently the same or different and are H, or a linear or branched chain alkyl, alkylaryl, or hydroxyalkyl group, or an aryl group; R$^5$ is a linear or branched chain alkyl, alkylaryl, alkoxyalkyl, aryloxyalkyl, or hydroxyalkyl group, or an aryl group, or (CH$_2$)$_n$NR$^{11}$R$^{12}$, or (CH$_2$)$_n$OR$^{11}$; R$^7$ is OH, or a linear or branched chain alkyl, alkoxy, alkylaryl, or alkylaryloxy group or an aryl group; R$^6$, R$^8$, and R$^9$ are independently the same or different and are H, or a linear or branched chain alkyl, alkylaryl, alkoxy, aminoalkoxy, or hydroxyalkyl group, or an aryl or aryloxy group, or nitro, CO$_2$R, Cl, F, Br, I, or SR$^{10}$; R$^{10}$, R$^{11}$ and R$^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9. The hydroxylating reagent of the treating step (f), above, favorably comprises gaseous oxygen, cupric halide, and a base.

In one embodiment, the invention provides a process of synthesizing a compound having the structure:

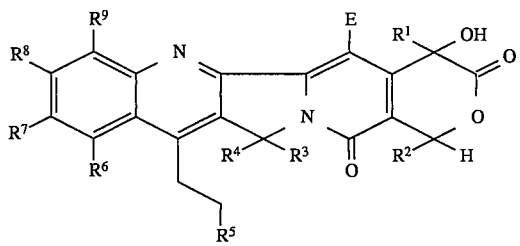

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOr^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9, which comprises:

(a) preparing a compound having the structure:

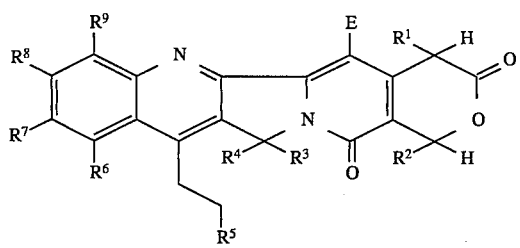

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOr^{11}$; $R^7$ is OH or a linear or branched chain alkyl, alkoxy, alkylaryl, or alkylaryloxy group or an aryl group; $R^6$, $R^8$ and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9, as described above, and, (b) treating the compound prepared in step (a) with a hydroxylating reagent under suitable conditions to form a compound having the structure:

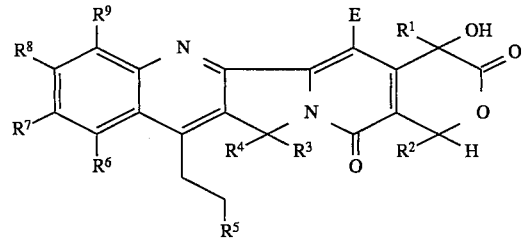

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$, and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9. The hydroxylating reagent of the treating step (b), above, favorably comprises gaseous oxygen, cupric halide, and a base.

In another embodiment, the invention provides a process of synthesizing a compound having the structure:

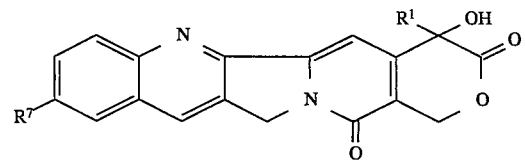

wherein $R^1$ is ethyl and $R^7$ is OH, which comprises:

(a) condensing a compound having the structure:

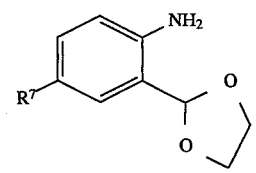

wherein $R^7$ is OH with a compound having the structure:

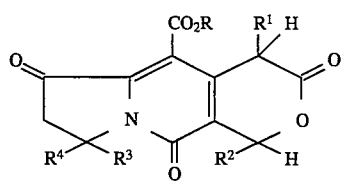

wherein R is H, or a linear or branched chain alkyl, alkylaryl, or hydroxyalkyl group, or an aryl group; $R^1$ is ethyl; $R^2$, $R^3$, and $R^4$ are H; and $R^7$ is OR, with a suitable acidic catalyst comprising p-toluenesulfonic acid in toluene to form a compound having the structure:

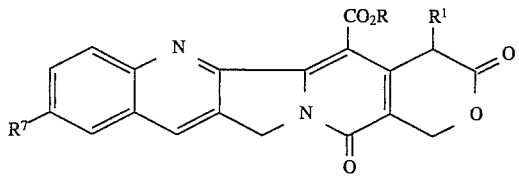

wherein R is H, or a linear or branched chain alkyl, alkylaryl, or hydroxyalkyl group, or an aryl group; $R^1$ is ethyl; and $R^7$ is OR;

(b) hydrolyzing and decarboxylating the compound formed in step (a) with a suitable acid comprising hydrobromic acid to form a compound having the structure:

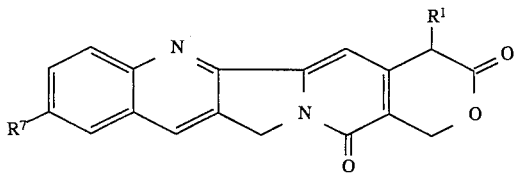

wherein $R^1$ is ethyl and $R^7$ is OR; and (c) treating the compound formed in step (b) with a hydroxylating reagent under suitable conditions to form a compound having the structure:

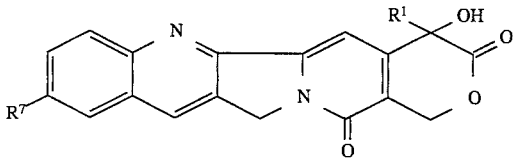

wherein $R^1$ is ethyl and $R^7$ is OH. The hydroxylating reagent of the treating step (c) favorably comprises gaseous oxygen, cupric halide, and a base.

In yet another embodiment, the invention provides a process of synthesizing a compound having the structure:

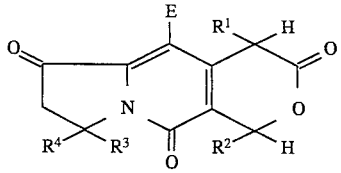

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, which comprises:

(a) treating a compound having the structure:

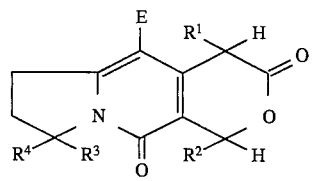

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; with a hydroxylating reagent under suitable conditions to form a compound having the structure:

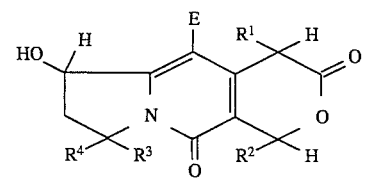

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group;

(b) oxidizing the compound formed by step (a) with an oxidant under suitable conditions to form a compound having the structure:

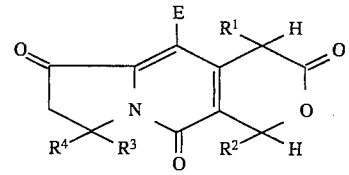

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group. The hydroxylating reagent of the treating step (a) favorably comprises gaseous oxygen, trialkyl phosphite, and sodium hexamethyldisilazide. The oxidant is favorably pyridinium dichromate.

The invention additionally provides a process of synthesizing a compound having the structure:

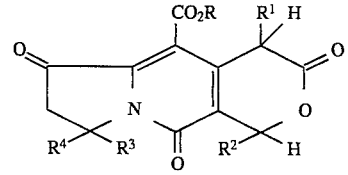

wherein $R^1$, $R^2$, $R^3$, and $R^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group, which comprises:

(a) condensing an aryl aldehyde with a compound having the structure:

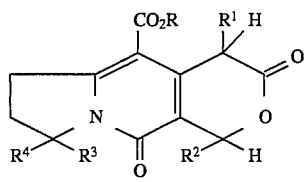

wherein $R^1$, $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group, with a basic reagent under suitable conditions to form a compound having the structure:

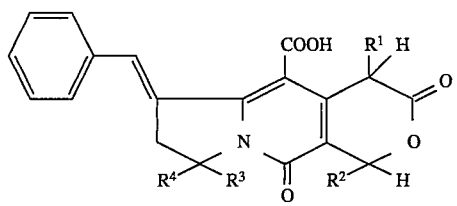

wherein $R^1$, $R^2$, $R^3$, and $R^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group;

(b) ozonolyzing the compound formed by step (a) under suitable conditions to form a compound having the structure:

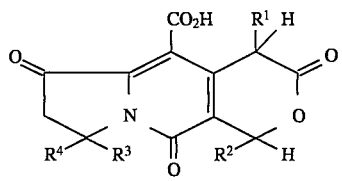

wherein $R^1$, $R^2$, $R^3$, and $R^4$ are independently the same or different and are H, or a linear or branched chain alkyl, alkylaryl, or hydroxyalkyl group, or an aryl group; and (c) re-esterifying the compound formed in step (b) with a suitable reagent under suitable conditions to form a compound having the structure:

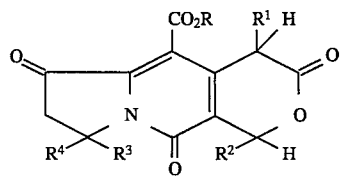

wherein $R^1$ $R^2$, $R^3$, and $R^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group. The basic reagent of the condensing step (a) favorably comprises sodium hexamethyldisilazide. The reagent of reesterifying step (c) is favorably trimethylsilyldiazomethane.

The invention also provides a process of synthesizing a compound having the structure:

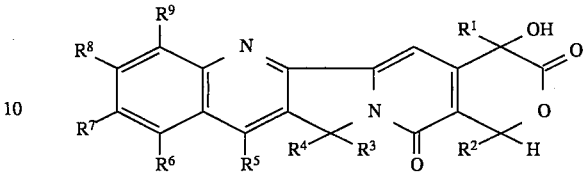

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOr^{11}$; $R^7$ is OH or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9, which comprises:

(a) preparing a compound as described hereinabove having the structure:

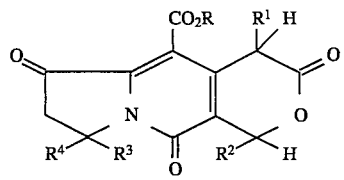

wherein R is H, or a linear or branched chain alkyl, alkylaryl, or hydroxyalkyl group, or an aryl group; and $R^1$, $R^2$, $R^3$, and $R^4$ are independently the same or different and are H, or a linear or branched chain alkyl, alkylaryl, or hydroxyalkyl group, or an aryl group;

(b) condensing the compound formed in step (a) with a compound having the structure:

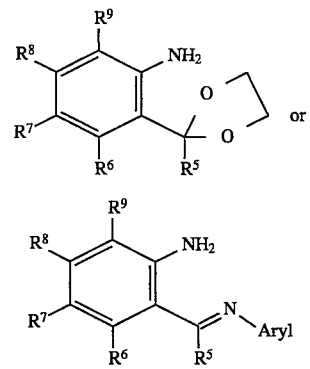

wherein $R^5$ is a linear or branched chain alkyl, alkylaryl, alkoxyalkyl, aryloxyalkyl, or hydroxyalkyl group, or an aryl group or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9, under suitable conditions to form the compound having the structure:

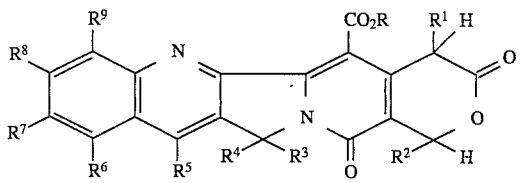

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$ or $(CH_2)_nOR^{11}$; $R^7$ is OH or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9;

(c) hydrolyzing and decarboxylating the compound formed in step (b) under suitable conditions to form a compound having the structure:

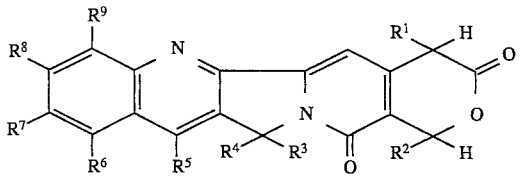

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH or a linear or branched chain alkyl, alkoxy, alkylaryl, or alkylaryloxy group, or an aryl group; $R^6$, $R^8$, and $R^9$ are independently the same or different and are H, or a. linear or branched chain alkyl, alkylaryl, alkoxy, aminoalkoxy, or hydroxyalkyl group, or an aryl or aryloxy group, or nitro, $CO_2R$, Cl, F Br, I or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9; and, (d) treating the compound formed in step (c) with a hydroxylating reagent under suitable conditions to form a compound having the structure:

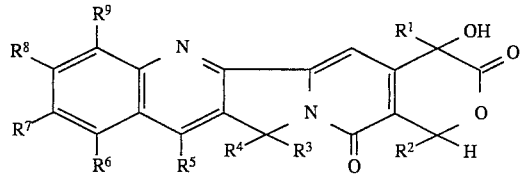

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9. The hydroxylating reagent in step (d), above, favorably comprises gaseous oxygen, cupric halide, and a base.

The invention also provides a process of synthesizing a compound having the structure:

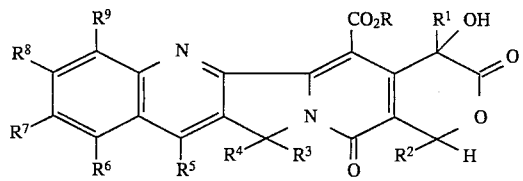

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group, or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9, which comprises:

(a) preparing a compound as described hereinabove having the structure:

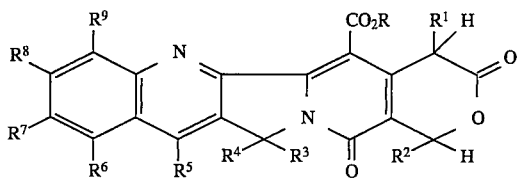

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH or a linear or branched chain alkyl, alkoxy, alkylaryl, or alkylaryloxy group, or an aryl group; $R^6$, $R^8$, and are independently $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9; and (b) treating the compound formed in step (a) with a hydroxylating reagent under suitable conditions to form a compound having the structure:

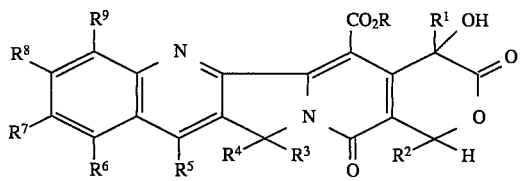

wherein $R^1$, $R^2$, $R^3$, and $R^4$ are independently the same or different and are H, or a linear or branched chain alkyl, alkylaryl, or hydroxyalkyl group, or an aryl group; $R^5$ is a linear or branched chain alkyl, alkylaryl, alkoxyalkyl, aryloxyalkyl, or hydroxyalkyl group, or an aryl group, or $(CH_2)_nNR^{11}R^{12}$, or $(CH_2)_nOR^{11}$; $R^7$ is OH, or a linear or branched chain alkyl, alkoxy, alkylaryl, or alkylaryloxy group or an aryl group; $R^6$, $R^8$, and $R^9$ are independently the same or different and are H, or a linear or branched chain alkyl, alkylaryl, alkoxy, aminoalkoxy, or hydroxyalkyl group, or an aryl or aryloxy group, or nitro, $CO_2R$, Cl, F, Br, I, or $SR^{10}$; $R^{10}$, $R^{11}$ and $R^{12}$ are independently the same or different and are H, or a linear or branched chain alkyl, alkylaryl, hydroxyalkyl, or acyl group, or an aryl or glycosyl group; R is H, or a linear or branched chain alkyl, alkylaryl, or hydroxyalkyl group, or an aryl group; and n is an integer from 0 to 9. The hydroxylating reagent in step (b), above, favorably comprises gaseous oxygen, cupric halide, and a base.

The invention also encompasses a process of synthesizing a compound having the structure:

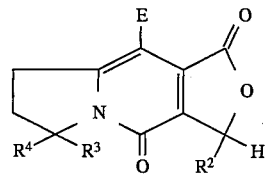

wherein E is H, $CO_2R$, $CONH_2$, CONHR, $CONR_2$, or CN; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and n is an integer from 0 to 9, which comprises:

(a) preparing a compound having the structure:

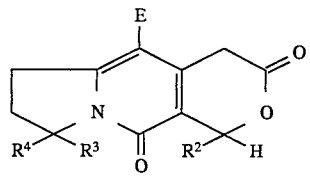

wherein E is H, $CO_2R$, $CONH_2$, CONHR, $CONR_2$, or CN; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and n is an integer from 0 to 9;

(b) treating the compound formed in step (a) with a hydroxylating reagent under suitable conditions to form a compound having the structure:

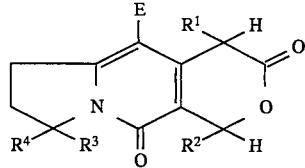

wherein E is H, $CO_2R$, $CONH_2$, CONHR, $CONR_2$, or CN; $R^1$ is OH; $R^2$, $R^3$, and $R^4$ are independently the same or different and are H, or a linear or branched chain alkyl, alkylaryl, or hydroxyalkyl group, or an aryl group; R is H, or a linear or branched chain alkyl, alkylaryl, or hydroxyalkyl group, or an aryl group; and n is an integer from 0 to 9; and (c) oxidizing the compound formed in step (b) with an oxidant under suitable conditions to form the compound having the structure:

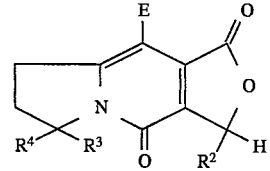

wherein E is H, $CO_2R$, $CONH_2$, CONHR, $CONR_2$, or CN; $R^1$, $R^2$, $R^3$, and $R^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group. The hydroxylating reagent in step (b) is favorably selenium dioxide. The oxidant in step (c) is favorably pyridinium dichromate.

In addition, the invention provides a process of synthesizing a compound having the structure:

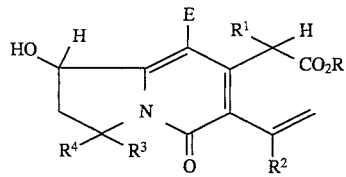

wherein E is H CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group, which comprises:

(a) preparing a compound having the structure:

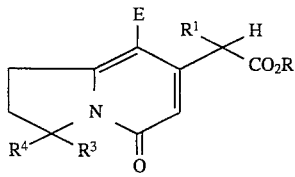

wherein E is H, CO$_2$R, CONH$_2$, CONHR, CONR$_2$, or CN; R$^1$, R$^3$, and R$^4$ are independently the same or different. and are H, or a linear or branched chain alkyl, alkylaryl, or hydroxyalkyl group, or an aryl group; and R is H, or a linear or branched chain alkyl, alkylaryl, or hydroxyalkyl group, or an aryl group;

(b) reacting the compound formed in step (a) with a halogenating reagent to form a compound having the structure:

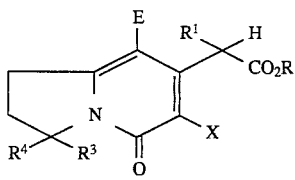

wherein X is Br, Cl, or I; E is H, CO$_2$R, CONH$_2$, CONHR, CONR$_2$, or CN; R$^1$, R$^3$, and R$^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group;

(c) cross-coupling the compound formed in step (b) with an organometallic reagent having the structure:

wherein M is a trialkylstannyl moiety and R$^2$ is H, or a linear or branched chain alkyl, alkylaryl, or hydroxyalkyl group, or an aryl group, under suitable conditions to form a compound having the structure:

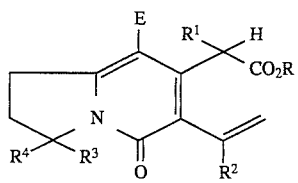

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group; and (d) treating the compound formed in step (c) with a base and a hydroxylating reagent under suitable conditions to form a compound having the structure:

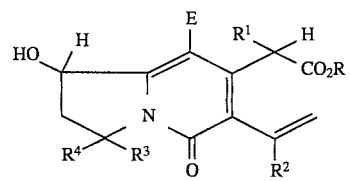

wherein E is H CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group. The halogenating reagent in the reacting step (b) favorably comprises Br$_2$, Cl$_2$, or I$_2$. The organometallic reagent in the cross-coupling step (c) is favorably a vinyl tri-n-butyl-stannane. In a preferred embodiment, the base in the treating step (d) is potassium hexamethyldisilazide, and the hydroxylating reagent has the structure:

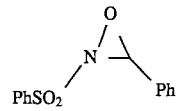

The invention provides a process of synthesizing a compound having the structure:

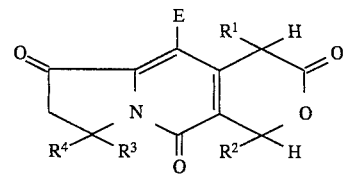

wherein E is H, CO$_2$R, CONH$_2$, CONHR, CONR$_2$, or CN; R$^1$, R$^2$, R$^3$, and R$^4$ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group, which comprises: (a) preparing as described hereinabove a compound having the structure:

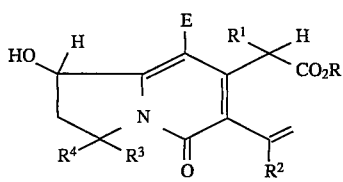

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; and, R is H, or a linear or branched chain alkyl, alkylaryl, or hydroxyalkyl group, or an aryl group;

(b) treating the compound formed in step (a) with an oxidative cleaving reagent under suitable conditions and with a hydride transfer reagent under suitable conditions to form a compound having the structure:

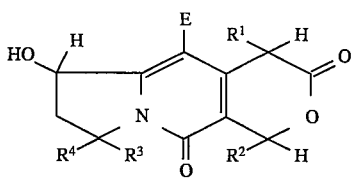

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group; and (c) oxidizing the compound formed in step (b) with an oxidant under suitable conditions to form a compound having the structure:

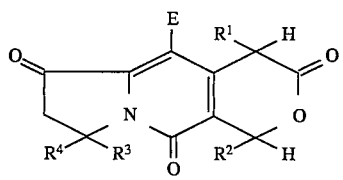

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group. The oxidative cleaving reagent in the treating step (b) is favorably ozone, and the hydride transfer agent therein is, in a preferred embodiment, lithium tri(t-butyloxy)boron hydride. The oxidant in the oxidizing step (c) is favorably pyridinium dichromate.

The invention further provides a process of synthesizing a compound having the structure:

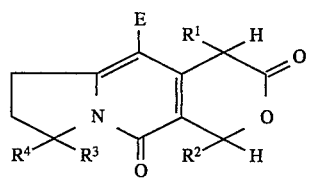

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group, which comprises:

(a) preparing a compound having the structure:

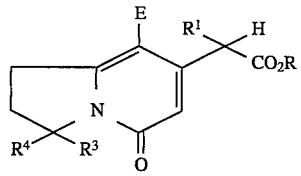

wherein E is H, CO₂R, CONH₂, CONHR, CONR₂, or CN; R¹, R³, and R⁴ are independently the same or different and are H, or a linear or branched chain alkyl, alkylaryl, or hydroxyalkyl group, or an aryl group; and R is H, or a linear or branched chain alkyl; alkylaryl, or hydroxyalkyl group, or an aryl group;

(b) treating the compound formed in step (a) with a basic reagent under suitable conditions to form a compound having the structure:

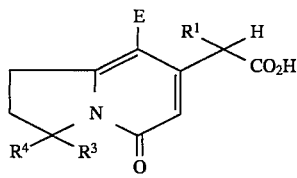

wherein E is H, CO₂R, CONH₂, CONHR, CONR₂, or CN; R is H, or a linear or branched chain alkyl, alkylaryl, or hydroxyalkyl group, or an aryl group; R¹, R³, and R⁴ are independently the same or different and are H, or a linear or branched chain alkyl, alkylaryl, or hydroxyalkyl group, or an aryl group; and (c) condensing the compound formed in step (b) with an aldehyde R²—CHO under suitable conditions to form a compound having the structure:

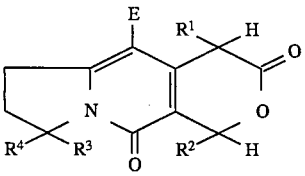

wherein E is H, CO₂R, CONH₂, CONHR, CONR₂, or CN; R¹, R², R³, and R⁴ are independently the same or different and are H, or a linear or branched chain alkyl, alkylaryl, or hydroxyalkyl group, or an aryl group; and R is H, or a linear or branched chain alkyl, alkylaryl, or hydroxyalkyl group, or an aryl group. The basic reagent is preferably potassium hydroxide. The aldehyde R²—CHO is favorably formaldehyde.

The subject invention provides a compound having the structure:

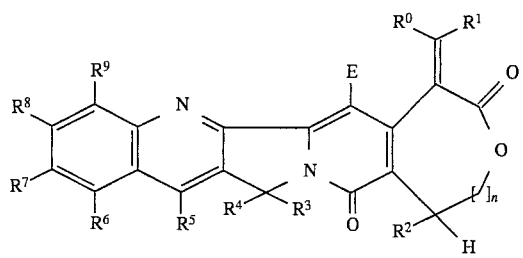

wherein E is H, $CO_2R$, $CONH_2$, CONHR, $CONR_2$, or CN; $R^0$ and $R^1$ are independently the same or different and are H, or a linear or branched alkyl, linear or branched alkylaryl, hydroxyalkyl or aryl group; $R^2$, $R^3$, and $R^4$ are independently the same or different and are H, or a linear or branched alkyl, linear or branched alkylaryl, hydroxyalkyl or aryl group; $R^5$, $R^6$, $R^7$, $R^8$, and $R^9$ are independently the same or different and are H, or a linear or branched alkyl, linear or branched alkylaryl or aryl group, or an alkoxy, aryloxy, hydroxyalkyl, C-glycal, nitro, cyano or aminoalkoxy group, or $CO_2R$, Cl, F, Br, I, $SR^{10}$, $NR^{11}R^{12}$ or $OR^{13}$; R is H, an alkyl, aryl, alkylaryl or hydroxyalkyl group; $R^{10}$, $R^{11}$ and $R^{12}$ are independently the same or different and are H, an alkyl, aryl, alkylaryl or acyl group; $R^{13}$ is glycosyl; and n is 0 or 1. In one embodiment, the subject invention provides the compound wherein n is 0. In another embodiment, the invention provides the compound wherein $R^7$ is OH. In another embodiment, the invention provides the compound wherein $R^6$ is C-glycal and the compound has the structure:

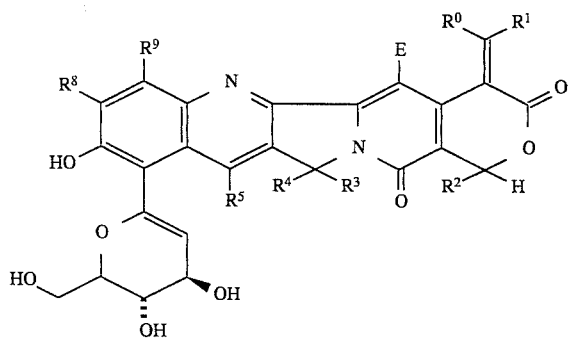

wherein E is H, $CO_2R$, $CONH_2$, CONHR, $CONR_2$, or CN; $R^0$ and $R^1$ are independently the same or different and are H, or a linear or branched alkyl, linear or branched alkylaryl, hydroxyalkyl or aryl group; $R^2$, $R^3$ and $R^4$ are independently the same or different and are H, or a linear or branched alkyl, linear or branched alkylaryl, hydroxyalkyl or aryl group; $R^5$ $R^8$, and $R^9$ are independently the same or different and are H, or a linear or branched alkyl, linear or branched alkylaryl, aryl, alkoxy, aryloxy, hydroxyalkyl, C-glycal, nitro, cyano or aminoalkoxy group, or $CO_2R$, Cl, F, Br, I, $SR^{10}$, $NR^{11}R^{12}$ or $OR^{13}$; R is H, an alkyl, aryl, alkylaryl or hydroxyalkyl group; $R^{10}$, $R^{11}$ and $R^{12}$ are independently the same or different and are H, an alkyl, aryl, alkylaryl or acyl group; and $R^{13}$ is glycosyl.

In another embodiment, the invention provides the compound wherein $R^5$ is ethyl. In another embodiment, the invention provides the compound wherein $R^1$, $R^2$, $R^3$, $R^4$ and E are H. In another embodiment, the invention provides the compound wherein $R^8$, and $R^9$ are H. In another embodiment, the invention provides the compound wherein $R^7$ is glycosyl and the compound has the structure:

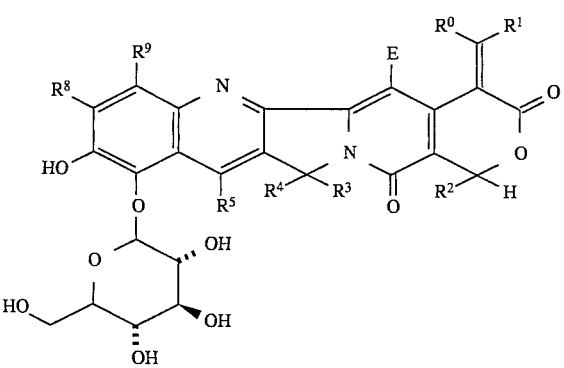

In another embodiment, the invention provides a compound wherein $R^5$ is ethyl. In another embodiment, the invention provides the compound wherein $R^1$, $R^2$, $R^3$, $R^4$ and E are H. In another embodiment, the invention provides the compound wherein $R^8$ and $R^9$ are H.

The invention also provides a process of synthesizing a compound having the structure:

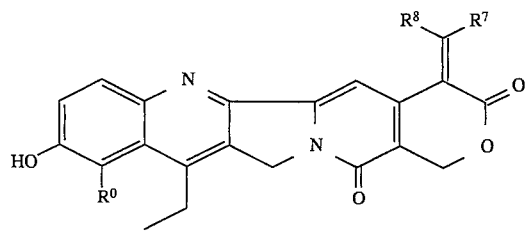

wherein $R^0$, is H, or a linear or branched alkyl, linear or branched arylalkyl, linear or branched alkylaryl or aryl group, or a C-glycal or O-glycosyl group; wherein $R^7$ and $R^8$ are independently the same or different and are H, or a linear or branched alkyl, linear or branched arylalkyl, linear or branched alkylaryl or aryl group, which comprises:

(a) preparing a compound having the structure:

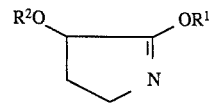

wherein $R^1$ and $R^2$ are independently the same or different and are a linear or branched alkyl, linear or branched arylalkyl, linear or branched alkylaryl, or aryl group;

(b) treating the compound formed in step (a) with Meldrum's acid under suitable conditions to form a compound having the structure:

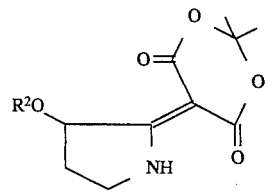

wherein $R^2$ is a linear or branched alkyl, linear or branched arylalkyl, linear or branched alkylaryl or aryl group;

(c) treating the compound formed in step (b) with base under suitable conditions to form a compound having the structure:

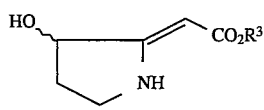

wherein $R^3$ is a linear or branched alkyl, linear or branched arylalkyl, linear or branched alkylaryl or aryl group;

(d) reacting the compound formed in step (c) with a suitable unsaturated carboxylic ester under suitable conditions to form a compound having the structure:

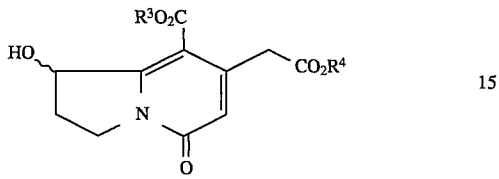

wherein $R^3$, and $R^4$ are independently the same or different and are a linear or branched alkyl, linear or branched arylalkyl, linear or branched-alkylaryl or aryl group;

(e) halogenating the compound formed in step (d) under suitable conditions to form a compound having the structure:

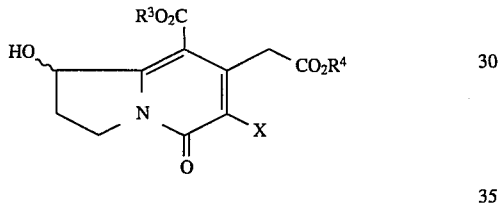

wherein $R^3$ and $R^4$ are independently the same or different and are a linear or branched alkyl, linear or branched arylalkyl, linear or branched alkylaryl or aryl group; and X is F, Cl, Br or I;

(f) treating the compound formed in step (e) under suitable conditions to form a compound having the structure:

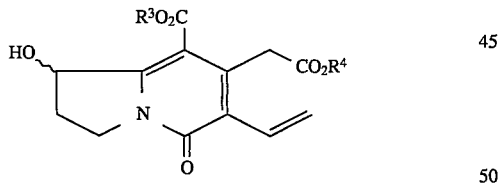

wherein $R^3$, and $R^4$ are independently the same or different and are a linear or branched alkyl, linear or branched arylalkyl, linear or branched alkylaryl or aryl group;

(g) alkylating the compound formed in step (f) with an alkylating agent under suitable conditions to form a compound having the structure:

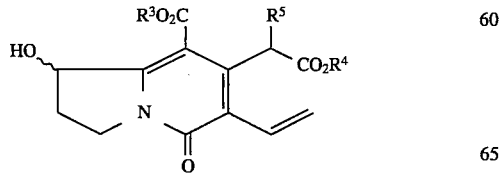

wherein $R^3$, $R^4$ and $R^5$ are independently the same or different and are a linear or branched alkyl, linear or branched arylalkyl, linear or branched alkylaryl or aryl group;

(h) cleaving oxidatively the compound formed in step (g) under suitable conditions and subsequently reducing under suitable conditions to form a compound having the structure:

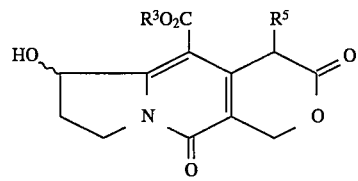

wherein $R^3$, and $R^5$ are independently the same or different and are linear or branched alkyl, linear or branched arylalkyl, linear or branched alkylaryl, or aryl;

(i) oxidizing the compound formed in step (h) under suitable conditions to form a compound having the structure:

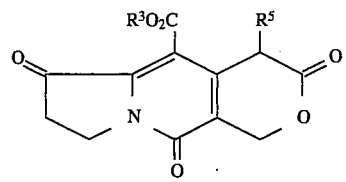

wherein $R^3$, and $R^5$ are independently the same or different and are a linear or branched alkyl, linear or branched arylalkyl, linear or branched alkylaryl or aryl group;

(j) condensing the compound formed in step (i) with a compound having the structure:

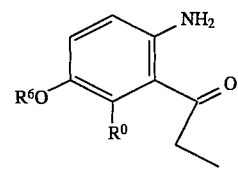

wherein $R^0$ is H, or a linear or branched alkyl, linear or branched aralkyl, linear or branched alkylaryl or aryl, or a C-glycal or O-glycosyl group; wherein $R^6$ is H, or a linear or branched allyl, linear or branched alkylaryl or aryl, or glycosyl group, under suitable conditions to form a compound having the structure:

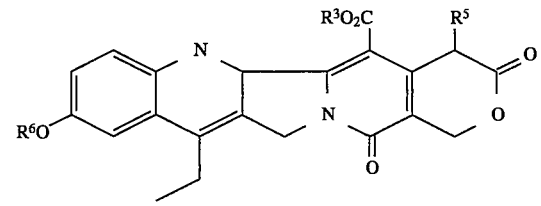

wherein $R^3$, and $R^5$ are independently the same or different and are a linear or branched alkyl, linear or branched arylalkyl, linear or branched alkylaryl or aryl group; and $R^6$ is H, or a linear or branched alkyl, linear or branched alkylaryl, or aryl, or O-glycosyl group;

(k) hydrolyzing and decarboxylating the compound formed in step (j) under suitable conditions to form a compound having the structure:

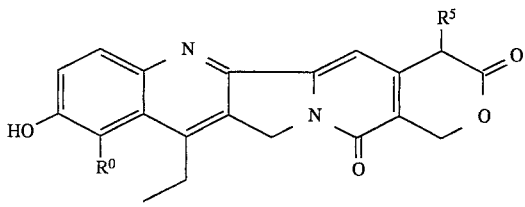

wherein R⁰ is H, or a linear or branched alkyl, linear or branched aralkyl, linear or branched alkylaryl or aryl, or a C-glycal or O-glycosyl group; wherein R³ is a linear or branched alkyl, linear or branched arylalkyl, linear or branched alkylaryl, or aryl group;

(l) selenylating the compound formed in step (k) under suitable conditions to form a compound having the structure:

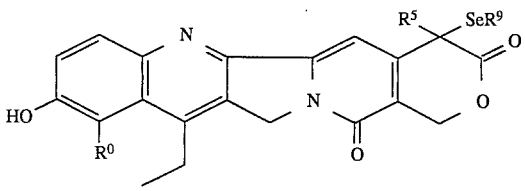

wherein R⁰ is H, or a linear or branched alkyl, linear or branched aralkyl, linear or branched alkylaryl or aryl, or a C-glycal or O-glycosyl group; wherein R⁵, and R⁹ are independently the same or different and are a linear or branched alkyl, linear or branched arylalkyl, linear or branched alkylaryl, or aryl group; and (m) dehydroselenylating the compound formed in step (l) under suitable conditions to form a compound having the structure:

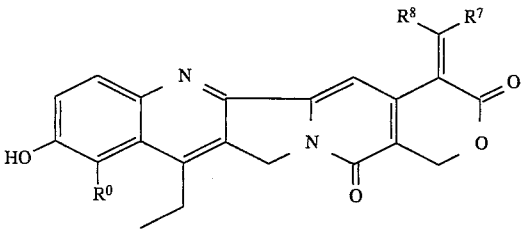

wherein R⁰ is H, or a linear or branched alkyl,linear or branched aralkyl, linear or branched alkylaryl or aryl, or-a C-glycal or O-glycosyl group; wherein R⁷ and R⁸ are independently the same or different and are H, or a linear or branched alkyl, linear or branched arylalkyl, linear or branched alkylaryl or aryl group. In one embodiment, the invention provides the process wherein R¹ is CH₃ and R₂ is Ac. In another embodiment, the invention provides the process wherein R¹ and R³, are both CH₃, and R₂ is Ac. In another embodiment, the invention provides the process wherein R¹, R³, and R⁴ are all CH3, and R₂ is Ac. In another embodiment, the invention provides the process wherein R¹, R³, and R⁴ are all CH₃, R₂ is Ac, and X is Br. In another embodiment, the invention provides the process wherein R¹, R³,R⁴ and R⁵ are all CH₃, R₂ is Ac, and X is Br. In another embodiment, the invention provides the process wherein R¹, R³, R⁴, R⁵ and R⁶ are all CH₃, R₂ is Ac, and X is Br. In another embodiment, the invention provides the process where R¹, R³, R⁴, R⁵ and R⁶ are all CH₃, R₂ is Ac, X is Br, and R⁷ and R⁸ are both H.

Step (b) hereinabove is preferably carried out at elevated temperatures, preferably at reflux, in an organic solvent such as benzene, in the presence of an organic base such as triethylamine. Step (c) is performed at elevated temperatures, preferably at reflux, in an organic solvent such as methanol in the presence of a base such as sodium methoxide.

Step (d) is carried out in an organic solvent such as absolute ethanol, in the presence of an organic base such as triethylamine; the unsaturated carboxylic ester may be dimethyl 3-chloroglutaconate. Step (e) is performed in a dipolar aprotic solvent such as dimethyl formamide (DMF) using a halogenating agent such as N-bromosuccinimide (NBS), preferably at ambient temperatures.

Step (f) is carried out under so-called Heck conditions using Pd(II) acetate and a phosphine such as tri-o-tolylphosphine, in the presence of an organic base such as triethylamine in a dipolar aprotic solvent such as acetonitrile, at moderate pressures (preferably at 75 psi) and elevated temperatures (preferably at 125° C.) in a sealed tube.

Step (g) may be performed using any alkylating agent such as a halide, sulfate, tosylate or acetate, in the presence of an organic base such as LiHMDS, preferably at low temperatures (e.g. –78° C.) in an organic solvent, preferably tetrahydrofuran (THF). Step (h) is performed using ozone or another oxidative cleaving agent, and proceeds effectively at low temperatures, preferably –78° C., in an inert organic solvent such as dichloromethane. Step (i) is carried out using a variety of oxidants, preferably the Dess-Martin periodinane in an organic solvent such as dichloromethane.

Step (j) is performed in an inert organic solvent such as toluene using an acid catalyst, preferably a mild acid such as p-tosic acid, at elevated temperatures, such as at the reflux temperture of the solvent.

Step (k) is performed using a strong acid such as HBr at elevated temperatures, preferably at 130° C. in a sealed tube. Step (l) is carried out using phenylselenyl bromide in a basic organic solvent such as pyridine. Step (m) is performed in an organic solvent such as dichloromethane, using hydrogen peroxide dissolved in a protic organic solvent such as methanol at low temperatures such as 0° C.

The invention also provides a process for preparing a compound having the structure:

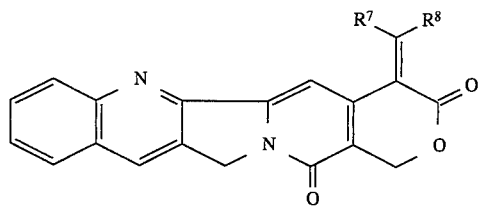

wherein R⁷ and R⁸ are independently the same or different and are H, or a linear or branched alkyl, linear or branched arylalkyl, linear or branched alkylaryl or aryl group, which comprises:

(a) preparing as described hereinabove the compound having the structure:

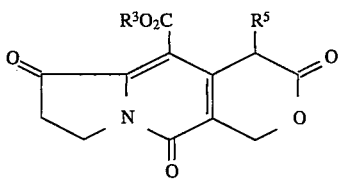

wherein $R^3$ and $R^5$ are independently the same or different and are a linear or branched alkyl, linear or branched arylalkyl, linear or branched alkylaryl, or aryl group;

(b) condensing the compound formed in step (a) with a compound having the structure:

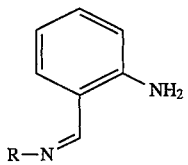

wherein R is a linear or branched alkyl, linear or branched arylalkyl, linear or branched alkylaryl or aryl group, under suitable conditions to form a compound having the structure:

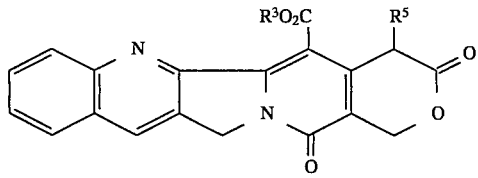

wherein $R^3$, and $R^5$ are independently the same or different and are a linear or branched alkyl, linear or branched arylalkyl, linear or branched alkylaryl, or aryl group;

(c) hydrolyzing and decarboxylating the compound formed in step (b) under suitable conditions to form a compound having the structure:

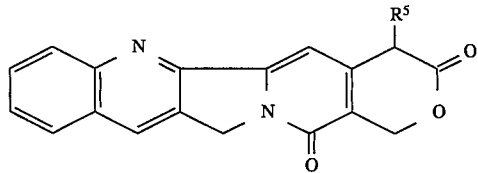

wherein $R^5$ is a linear or branched alkyl, linear or branched arylalkyl, linear or branched alkylaryl or aryl group;

(d) selenylating the compound formed in step (c) under suitable conditions to form a compound having the structure:

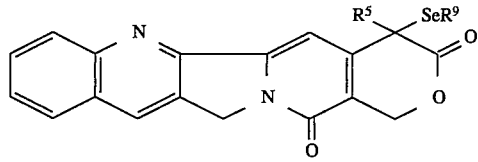

wherein $R^5$ is a linear or branched alkyl, linear or branched arylalkyl, linear or branched alkylaryl or aryl group; and wherein $R^9$ is H, or a linear or branched alkyl, linear or branched arylalkyl, linear or branched alkylaryl or aryl group; and (e) dehydroselenylating the compound formed in step (d) under suitable conditions to form a compound having the structure:

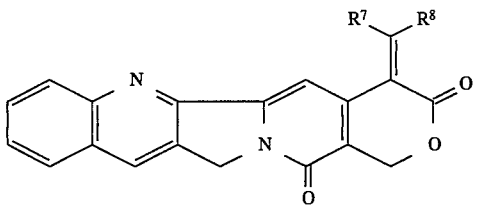

wherein $R^7$ and $R^8$ are independently the same or different and are H, or a linear or branched alkyl, linear or branched arylalkyl, linear or branched alkylaryl or aryl group. In another embodiment, the invention provides the process wherein $R^1$ and $R^3$ are both $CH_3$, and $R_2$ is Ac. In another embodiment, the invention provides the process wherein $R^1$, $R^3$, and $R^4$ are all $CH_3$ and $R_2$ is Ac In another embodiment, the invention provides the process wherein $R^1$, $R^3$ and $R^4$ are all $CH_3$, $R_2$ is Ac, and X is Br. In another embodiment, the invention provides the process wherein $R^1$, $R^3$, $R^4$, are all $CH_3$, $R_2$ is Ac, and X is Br. In another embodiment, the invention provides the process wherein $R^1$, $R^3$, $R^4$, $R^5$ and $R^6$ are all $CH_3$, $R_2$ is Ac, and X is Br. In another embodiment, the invention provides the process wherein $R^1$, $R^3$, $R^4$, $R^5$ and $R^6$ are all $CH_3$, $R_2$ is Ac, X is Br, and $R^7$ and $R^8$ are both H.

Step (b) is performed in an inert organic solvent such as toluene using an acid catalyst, preferably a mild acid such as p-tosic acid, at elevated temperatures, such as at the reflux temperture of the solvent. Step (c) is performed using a strong acid such as HBr at elevated temperatures, preferably at 130° C. in a sealed tube. Step (d) is carried out using phenylselenyl bromide in a basic organic solvent such as pyridine. Step (e) is performed in an organic solvent such as dichloromethane, using hydrogen peroxide dissolved in a protic organic solvent such as methanol at low temperatures such as 0° C.

The subject invention further provides a pharmaceutical composition which comprises the compound having the structure:

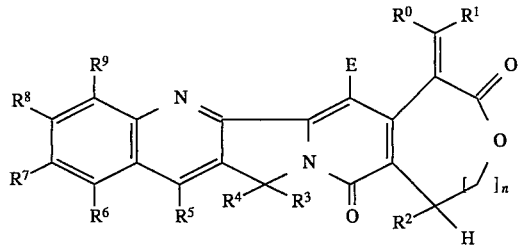

wherein E is H, $CO_2R$, $CONH_2$, CONHR, $CONR_2$, or CN; $R^0$ and $R^1$ are independently the same or different and are H, or a linear or branched alkyl, linear or branched alkylaryl, hydroxyalkyl or aryl group; $R^2$, $R^3$ and $R^4$ are independently the same or different and are H, or a linear or branched alkyl, linear or branched alkylaryl, hydroxyalkyl or aryl group; $R^5$, $R^6$, $R^7$, $R^8$ and $R^9$ are independently the same or different and are H, or a linear or branched alkyl, linear or branched alkylaryl or aryl group, or an alkoxy, aryloxy, hydroxyalkyl, C-glycal, nitro, cyano or aminoalkoxy group, or $CO_2R$, Cl, F, Br, I, $SR^{10}$, $NR^{11}R^{12}$ or $OR^{13}$; R is H, an alkyl, aryl, alkylaryl or hydroxyalkyl group; $R^{10}$, $R^{11}$ and $R^{12}$ are independently the same or different and are H, an alkyl, aryl, alkylaryl or acyl group; $R^{13}$ is glycosyl; and n is 0 or 1; in a therapeutically effective amount and a pharmaceutically acceptable carrier. In one embodiment, the invention provides the pharmaceutical composition wherein the carrier is a solid and the composition is a tablet. In another embodiment, the invention provides the pharmaceutical composition wherein the therapeutically effective amount is an amount from about 1 to about 500 mg. In another embodiment, the invention provides the pharmaceutical composition wherein the carrier is a liquid and the composition is a solution. In another embodiment, the invention provides the pharmaceutical composition wherein the therapeutically effective amount is an amount from about 0.1 to about 500 mg per mL of solution.

The subject invention also provides a method of treating solid tumors in a subject which comprises administering to the subject a therapeutically effective amount of any one of the compounds disclosed hereinabove. In one embodiment, the invention provides a method wherein the therapeutically effective amount is an amount from about 0.1 to about 10 mg/kg of body weight.

The subject invention also provides a method of inhibiting growth of tumor cells in a host in need of treatment therefor which comprises administering to the host a therapeutically effective amount of any one of the compounds disclosed hereinabove. In one embodiment, the invention provides a method wherein the therapeutically effective amount is an amount from about 0.1 to about 10 mg/kg of body weight.

Biological Properties

Cytotoxicity Assay.

The synthesized compounds were evaluated for their cytotoxic effects on HL-60 (human promyelocytic leukemia) and 833K cells. The assay was conducted in 96-well microplates. The compounds were serially diluted in 4 to 6 steps with dimethylsulfoxide and added to cell incubation medium (RPMI 1640 containing 10% fetal. cell serum) at the final concentration of 1.0% dimethylsulfoxide in the medium. The cytotoxicity of the compounds were determined by the XTT-microculture tetrazolium assay: 2',3'-bis(2-methoxy-4-nitro-5-sulfophenyl)-3-[(phenylamino)carbonyl]-2H-tetrazolium hydroxide (XTT) was prepared at 1 mg/mL in prewarmed (37° C.) medium without serum. Phenazine methosulfate (PMS) and fresh XTT were mixed together to obtain 0.075 mM PMS-XTT solution (25 mL of the stock with 5 mg PMS added per 5 mL of 1 mg/mL XTT). Fifty microliters of this mixture were added to each well of the cell culture after 72 hours exposure to the testing compound. After incubation at 37° C. for 6 hours, the absorbance was determined at 450 nm and 630 nm with a microplate reader (EL 340, Bio-Tek Instruments, Inc., Winooski, Vt.). THe median-effect inhibitory concentration ($IC_{50}$) was determined from a medium-effect plot using computer software for the purpose.

The results of the assay of cytotoxicity towards HL-60 and 833K cells of several analogues of camptothecin prepared in accord with the invention are illustrated in the accompanying Tables I and II, along with comparison data for native camptothecin. The data shown indicate that the camptothecin analogues prepared by the new methods provided by the invention have significant cytotoxic activity against cancer cells. The data shown indicate that the new camptothecin analogues have significant cytotoxic activity against cancer cells.

The present invention therefore provides a method of treating cancer, which comprises administering an anti-cancer-effective quantity of any of the analogues of camptothecin disclosed herein. The drug may be administered to a patient afflicted with cancer by any conventional route of administration, including, but not limited to, intravenous, intramuscular, oral, subcutaneous, intratumoral, intradermal, and parenteral. The anticancer-effective quantity is between 0.01 mg and 10.0 mg per kg of subject body weight.

The present invention also provides a pharmaceutical composition comprising any of the analogues of camptothecin disclosed herein and a pharmaceutically acceptable carrier. The composition may contain between 1 mg and 500 mg of a camptothecin analogue, and may be constituted into any form suitable for the mode of administration selected. Compositions suitable for oral administration include solid forms, such as pills, capsules, granules, tablets, and powders, and liquid forms, such as solutions, syrups, elixers, and suspensions. Forms useful for parenteral administration include sterile solutions, emulsions, and suspensions.

The drug may otherwise be prepared as a sterile solid composition which may be dissolved or suspended at the time of administration using sterile water, saline, or other appropriate sterile injectible medium. Carriers are intended to include necessary and inert binders, suspending agents, lubricants, flavorants, sweeteners, preservatives, dyes, and coatings.

Optimal dosages to be administered may be determined by those skilled in the art, and will vary with the particular camptothecin analogue in use, the strength of the preparation, the mode of administration, and the advancement of the disease condition. Additional factors depending on the particular patient being treated will result in a need to adjust dosages, including patient age, weight, gender, diet, and time of administration.

TABLE I

CYTOTOXICITY OF CAMPTOTHECIN AND DERIVATIVES ON HL60 CELL AND 833K CELL GROWTH DURING 72 HR EXPOSURE, USING XTT ASSAYS

| Compound[a] | TopoI Relaxation | TopoI DNA Cleavage | Inhibitory Concentrations | | | | | |
|---|---|---|---|---|---|---|---|---|
| | | | HL-6 | | | 833K | | |
| | | | $IC_{50}$ | $IC_{70}$ | $IC_{95}$ | $IC_{50}$ | $IC_{70}$ | $IC_{95}$ |
| WS-1 (CPT) | ++++ | +++ | 0.0094 | 0.012 | 0.025 | +0.004 | +0.004 | 0.649 |
| Camptothecin | | | 0.0035 | 0.006 | 0.022 | 0.0153 | 0.043 | ±0.160 |
| WS-2 (20-deoxy-CPT) | +++ | ++ | 0.039 | 0.052 | 0.109 | 0.0096 | ±0.023 | 3.17 + 1.01 |
| 20-Deoxycamptothecin | | | | | | 0.310+ | 0.143 | |
| WS-3 (14-carbomethoxy-20-deoxy CPT) | +++ | + | 0.914 | 0.318 | 1.082 | >50 | | |

TABLE I-continued

CYTOTOXICITY OF CAMPTOTHECIN AND DERIVATIVES ON HL60 CELL AND 833K CELL GROWTH DURING 72 HR EXPOSURE, USING XTT ASSAYS

| Compound[a] | TopoI Relaxation | TopoI DNA Cleavage | Inhibitory Concentrations | | | | | |
|---|---|---|---|---|---|---|---|---|
| | | | HL-6 | | | 833K | | |
| | | | $IC_{50}$ | $IC_{70}$ | $IC_{95}$ | $IC_{50}$ | $IC_{70}$ | $IC_{95}$ |
| 14-Carbomethoxy-20-deoxycamptothecin WS-4 (14-carbomethoxy-20-deoxy CPT) | ++ | — | 2.44 | 12.0 | 618.7 | +0.287 2.263 | +0.820 5.80 | 59.8 ±11.7 |
| 14-Carbomethoxy-20-deoxycamptothecin WS-5 (14-carbomethoxy-CPT) 14-Carbomethoxy-Camptothecin | + | ± | >5 | — | — 63.5+ | 28.3 | 83.7 | 898 ± 750 |
| WS-6 (17-methyl-CPT) 17-Methylcamptothecin | ++ | | 0.266 | 0.432 | 1.432 | 0.254 3.71+ | +0.34 7.34 | 40.1± 0.689 |
| WS-7 (20-methyl-CPT) 20-Methylcamptothecin | ++++ | | 0.062 | 0.090 | 0.229 | +0.034 0.082 | 0.290 ±0.05 | 7.16± 2.84 |
| WS-8 20-dehydrated-CPT | + | | 3.44 | 5.47 | 17.14 | +0.250 1.70 | 4.75 ±0.092 | 50.4 ± 13.8 |
| 11-Isotopotecan | +++ | | >5 | — | — | >500 | | |

[a]All Compounds were dissolved in DMSO and heated to 56° C. prior to serial dilution with DMSO.

TABLE II

CYTOTOXICTY OF CAMPTOTHECIN AND DERIVATIVES ON HL-60 CELL GROWTH DURING 72 HR EXPOSURE, USING XTT ASSAYS

| Compound[b] | Topo I Relaxation | Topo I DNA Cleavage | Inhibitory $IC_{50}$ | Concentrations $IC_{70}$ | (μM) $IC_{95}$ |
|---|---|---|---|---|---|
| WS-1 (CPT) | ++++ | +++ | 0.0094 | 0.012 | 0.025 |
| Camptothecin | | | 0.0035 | 0.006 | 0.022 |
| WS-2 (20-deoxy-CPT) 20-Deoxycamptothecin | +++ | ++ | 0.039 | 0.052 | 0.109 |
| WS-3 (14-carbomethoxy-20-deoxy CPT) 14-Carbomethoxy-20-deoxycamptothecin | +++ | + | 0.194 | 0.318 | 1.082 |
| WS-4 (14-carbomethoxy-20-deoxy CPT) 14-Carbomethoxy-20-deoxycamptothecin | ++ | — | 2.44 | 12.0 | 618.7 |
| WS-5 (14-carbomethoxy-CPT) 14-Carbomethoxy-Camptothecin | + | ± | >5 | — | — |
| WS-6 (17-methyl-CPT) 17-Methylcamptothecin | ++ | | 0.266 | 0.432 | 1.432 |
| WS-7 (20-methyl-CPT) 20-Methylcamptothecin | ++++ | | 0.062 | 0.090 | 0.229 |
| WS-8 20-dehydrated-CPT | + | | 3.44 | 5.47 | 17.14 |
| 11-Isotopotecan | +++ | | >5 | — | — |
| Topotecan (844K cells) | | | 0.046 | — | — |

[b]All compounds were dissolved in DMSO and heated to 56° C. prior to several dilution with DMSO.

The following Experimental Details are set forth to aid in an understanding of the invention, and are not intended, and should not be construed, to limit in any way the invention set forth in the claims which follow thereafter.

Experimental Details

General

All air and moisture sensitive reactions were performed in a flame-dried apparatus under a nitrogen atmosphere unless otherwise noted. Air-sensitive liquids and solutions were transferred via syringe or cannula. Unless otherwise noted, all solvents and reagents were commercial grade and were used as sold. The following are exceptions, and are all distilled under nitrogen using the drying methods listed in parentheses: dichloromethane (calcium hydride), benzene (calcium hydride), tetrahydrofuran (sodium/benzophenone ketyl), diethyl ether (sodium/benzophenone ketyl), diisopropylamine (calcium hydride).

Melting points (mp) were uncorrected and performed in soft glass capillary tubes using an Electrothermal series IA9100 digital melting point apparatus. Infrared (IR) spectra were obtained with a Perkin-Elmer 1600 Series Fourier Transform Spectrometer. Samples were prepared as neat films on NaCl plates unless otherwise noted. Proton nuclear magnetic resonance (1H NMR) spectra were determined using a Bruker AMX-400 spectrometer operating at 400 MHz. Carbon nuclear magnetic resonance (13C NMR) spectra were obtained on a Bruker AMX-400 spectrometer operating at 100 MHz with composite pulse decoupling. High resolution mass spectra (HRMS) were determined by electron impact ionization (EI) on a JEOL JMS-DX 303HF mass spectrometer with perfluorokerosene (PFK) as an internal standard.

Flash chromatography was carried out on silica gel according to the protocol of Still (W. C. Still, et al., *J. Org. Chem.*, 43, 2923 (1978)).

EXAMPLE 1

2-Methoxypyrroline.

To the stirring neat dimethyl sulfate (265.0 g, 2.1 mol) was added dropwise 2-pyrrolidinone (170 g, 2.00 mol) over 2 h. The reaction was then heated at 60 C. for 16 h. After cooling the reaction to room temperature, it was poured onto ice (500 g) mixed with potassium carbonate (300 g). The organic layer was separated and the aqueous layer was extracted with ether (3×100 mL). The combined organic layer and extracts were dried over anhydrous magnesium sulfate, filtered, and concentrated under vacuum (the bath temperature was kept under 20° C.). The resulting solution was distilled under vacuum to give 156.4 g (37°–40° C., 74 torr), which was redistilled at 115°–120° C. under atmosphere to give of the desired product (129 g, 65%). $^1$H NMR (400 MHz, CDCl3) 3.80 (s, 3 H), 3.65(tt, J=1.2, 7.1 Hz, 2H), 2.43 (tt, J=1.2, 7.4 Hz, 2H), 2.02 (m, 2H). $^{13}$C NMR (100 MHz, CDCl3) 10.10 (brs, 1H), 3.73 (t, J=7.6 Hz, 2H),3.39 (t, J=8.0 Hz, 2H), 2.16 (quintet, J=7.7 Hz, 2H), 1.68 (s,6H).

EXAMPLE 2

Isopropylidene α-(Tetrahydro-2-pyrrolidene)malonate (3).

A solution of 2 (55.8 g, 0.563 mol), Meldrum's acid (81.1 g, 0.563 mol) and triethylamine (10 mL) in benzene (300 mL) was refluxed 10 h. The solid residue after evaporation of the reaction mixture was recrystallized from absolute ethanol to give the desired product 3 as white crystals (110.0 g, 92.5%). $^1$H NMR (400 MHz, CDCl$_3$) δ10.10 (brs, 1H), 3.73 (t, J=7.6 Hz, 2H), 3.39 (t, J=8.0 Hz, 2H), 2.16 (quintet, J=7.7 Hz, 2H) , 1.68 (s, 6H).

EXAMPLE 3

2-Carbomethoxymethylenepyrroline (4).

To the solution of 3 (42.2 g, 200 mmol) in anhydrous methanol (200 mL) was added a solution of sodium methoxide in methanol (25% w/w, 47.5 g, 220 mmol), and the resulting solution was refluxed 2 h. The reaction mixture was concentrated under vacuum to a semi solid before iced water (200 mL) was added to it. The resulting solution was adjusted to pH 5–6 by 2N HCl, and extracted with methylene chloride (5×100 mL). The combined extracts was dried over anhydrous magnesium sulfate, filtered, and concentrated to give yellow solid. Recrystallization of the residue solid from hexane afforded the desired product as pale yellow solid (27.6 g, 97.7%). $^1$H NMR (400 MHz, CDCl$_3$) 7.88 (brs, 1H) ,4.53 (s, 1H) , 3.62 (s,3H0, 3.51 (t,J=6.9 Hz, 2H), 2.57 (t,J=7.7 Hz, 2H), 1.96 (quintet, J=Hz, 2H). $^{13}$C NMR (100 MHz, CDCl$_3$) 171.0, 166.6, 76.2, 50.0, 47.0, 32.2, 22.0 ppm. IR (neat) 3365, 2948, 2881, 1652, 1603, 1501, 1237, 1146, 1064, 777 cm$^{-1}$.

EXAMPLE 4

3-Carbomethoxmethyl-4-carbomethoxy-1,6-cyclopentano-2 -pyridone (6).

To the solution of 4 (27.6 g, 195 mmol) in absolute ethanol (200 mL) was added dimethyl 1,3-allenyldicarboxylate 514 (33.6 g, 215 mmol) and triethylamine (2 mL). The reaction was stirred at room temperature for 65 h. The reaction mixture was concentrated to near dryness. Trituration of the residue with dry ether (50 mL) afforded 6 as a white solid (47.8 g, 92.3%). $^1$H NMR (400 MHz, CDCl$_3$) δ6.21 (s, 1H), 4.11 (t, J=7.4 Hz, 2H), 3.74 (s, 3H), 3.73 (s, 2H), 3.66 (s, 3H), 3.44 (t, J=7.9 Hz, 2H), 2.16 (quintet, J=7.6 Hz, 2H) $^{13}$C NMR (100 MHz, CDCl$_3$) δ170.9, 165.8, 161.0, 157.4, 147.1, 120.1, 106.5, 52.1, 51.6, 49.1, 41.1, 34.7, 20.6 ppm. IR (neat) 2953, 1734, 1716, 1656,1520, 1436, 1294, 1203 cm$^{-1}$.

EXAMPLE 5

3-(1-Carbomethoxypropyl)-4-carbomethoxy-1,6-cyclopentano-2-pyrridone (7).

To a solution of pyridone 6 (47.0 g, 177 mmol) in anhydrous dimethoxyethane (700 mL) at –78° C. was added potassium t-butoxide (20.8 g, 186 mmol). After 20 min ethyl iodide (50.3 g, 354 mmol) was added and the solution was allowed to warm to room temperature and stirred for 30 h. The reaction mixture was then poured to brine (300 mL) and the aqueous layer extracted with methylene chloride (4×200 mL). The combined organic phase and the extracts was dried over anhydrous magnesium sulfate, filtered, and concentrated. The semisolid residue was then recrystallized from ethyl acetate to give 7 as a pale yellowish green solid (36.54 g, 2 crops). The mother liquid was subjected to flash chromatography with ethyl acetate to afford more product (11.2 g, total yield 91.0%). $^1$H NMR (400 MHz, CDCl$_3$ δ6.35 (s, 1H), 4.13 (dt, J=1.2, 7.5 Hz, 2H), 3.99 (t, J=7.2 Hz, 1H), 3.80 (s, 3H), 3.64 (s, 3H), 3.39 (dt, J=2.6, 8.0 Hz, 2H), 2.17 (quintet, J=7.6 Hz, 2H), 2.05 (m, 1H), 0.91 (t, J=7.4 Hz, 3H). $^{13}$C NMR (100 MHz, CDCl$_3$) δ173.0, 166.1, 161.1, 156.3, 151.6, 117.2, 107.0, 53.1, 51.7, 49.8, 49.2, 34.5, 25.4, 20.7, 12.4 ppm. IR (neat) 2959, 2919, 1714, 1710, 1668, 1585, 1516, 1437, 1352, 1273, 1193, 1094, 1032, 976.3 cm$^{-1}$.

EXAMPLE 6

4-Carbomethoxy-de-AB-deoxycamptothecin (8).

A mixture of 7 (5.01 g, 17.1 mmol), formaldehyde (3.08 g), concentrated sulfuric acid (1 mL) and water (1 mL) in dioxane (25 mL) and extracted with methylene chloride (4×50 mL). The combined extracts was dried over anhydrous magnesium sulfate, filtered, and concentrated to a pale yellow sticky oil 8 which was already pure as shown by $^1$H NMR. Thr product was used directly for the next step. 1H NMR (400 MHz, CDCl$_3$) δ5.48 (d, J=5.8 Hz, 1H), 5.13 (d, J=5.8 Hz, 1H), 4.34 (dd, J=5.1, 9.1 Hz, 1H), 4.19, (dt, J=2.9, 7.6 Hz, 2H), 3.85, (s, 3H), 3.48 (dt, J=3.6, 7.9 Hz, 2H), 2.22 (quintet, J=7.6 Hz, 2H), 1.65–2.01 (m, 2H), 1.08 (t, J=7.6 Hz, 3H). $^{13}$C NMR (100 MHz, CDCl$_3$) δ171.3, 165.2, 157.9, 167.0, 147.3, 118.5, 104.9, 65.0, 52.0, 49.5, 44.3, 34.8, 25.3, 20.7, 11.9 ppm. IR (neat) 2925, 1734, 1713, 1650, 1548, 1440, 1309, 1170, 1097, 1047 cm$^{-1}$.

EXAMPLE 7

De-AB-deoxycamptothecin (9).

A mixture of 8 in aqueous hydrobromic acid (48%, 50 mL) was heated at 105° C. for 18 h. It was then poured into brine (60 mL) and extracted with methylene chloride (4×50 mL). The combined extracts was dried over anhydrous magnesium sulfate, filtered, and concentrated. The residue was then subjected to flash chromatography with 50:50:1 chloroform/ethyl acetate/methanol to afford 9 as an off-white solid (2.11 g, 52.9%). $^1$H NMR (400 MHz, CDCl$_3$) δ5.98 (s, 1H), 5.38 (d, J=5.7 Hz, 1H), 5.20 (d, J=5.7 Hz, 1H), 4.12 (t, J=7.3 Hz, 2H), 3.35 (t, J=6.6 Hz, 1H), 3.08 (t, J=7.7 Hz, 2H), 2.21 (quintet, J=7.74 Hz, 2H), 1.80–1.98 (m, 2H), 0.99 (t, J=7.4 Hz, 3H). $^{13}$C NMR (100 MHz, CDCl$_3$) δ171.4, 158.5, 150.5, 146.6, 117.2, 100.2, 66.1, 48.6, 45.8, 31.8, 25.1, 21.5, 11.3 ppm.

EXAMPLE 8

7-Hydroxy-AB-campothecin (10).

A mixture of 9 (778 mg, 3.33 mmol), selenium dioxide (1.85 g, 16.7 mmol) in wet dioxane (95%, 20 mL) in a sealed tube was heated at 155° C. for 4 h. It was then poured into water and extracted with methylene chloride (4×30 mL). The combined extracts was dried over anhydrous magnesium sulfate, filtered, and concentrated. The dark solid residue was then chromatographed with 25% acetone in chloroform (300 mL) and 30:20:1 chloroform/acetone/methanol (500 mL) to afford 10 as a yellowish solid (377.4 mg, 42.7%). The diastereomeric ratio is about 1:1. $^1$H NMR (400 MHz, DMSO-d$_6$ with 1 small drop of D$_2$O) δ6.51 (s, 1H), 5.25 (dd, J=15.4, 19.0 Hz, 2H), 5.13 (t, J=7.0 Hz, 1H), 4.08 9, 1H), 2.42 (m, 1H), 1.93 (m, 1H), 1.76 (m, 2H), 0.82 (t, J=7.1 Hz, 3H). $^{13}$C NMR (100 MHz, DMSO-d$_6$) δ172.59, 172.54, 156.87, 152.94, 152.90, 149.83, 149.78, 116.33, 97.37, 72.09, 72.04, 71.94, 65.16, 59.68, 45.62, 31.25, 31.19, 30.30, 30.26, 7.66 ppm (21 peaks observed). HRMS calculated for C$_{13}$H$_{15}$NO$_5$ (M$^+$) 265.0950, observed 265.0952.

EXAMPLE 9

2-Oxo-de-AB-camptothecin (11).

To the suspension of 10 (356.1 mg, 1.34 mmol) and 4 Å molecular sieves (activated powder, 1.50 g) in methylene chloride (15 mL) at 0° C. was added pyridinium dichoromate (1.01 g. 2.68 mmol). After 3.5 h, 30 mL ethyl acetate was added to the mixture, and it was filtered through a plug of silica gel and celite. The residue after evaporation of the filtrate was flash chromatographed with 1:1 chloroform/ethyl acetate to give 11 (159.6 mg, 45.2%). $^1$H NMR (400 MHz, CDCl$_3$) δ7.23, (s, 1H), 5.68, (d, J=7.1 Hz, 1H), 5.25, (d, J=7.1 Hz, 1H), 4.35 (t, J=6.8 Hz, 2H), 3.65 (s, 1H, from the OH), 2.97 (t, J=6.8 Hz, 2H), 1.82 (m, 2H), 0.99 (t, J=7.4 Hz, 3H). $^{13}$C NMR (100 MHz, CDCl$_3$) δ196.0, 173.3, 157.7, 149.3, 139.9, 124.5, 100.8, 72.3, 66.3, 42.2, 33.7, 31.8, 7.7 ppm. HRMS calculated for C$_{13}$H$_{13}$O$_5$ (M$^+$) 263.0794, observed 263.0809.

EXAMPLE 10 dl-Camptothecin (1).

A suspension of 11 (185.2 mg, 0.704 mmol) and 12 (178 mg, 0.844 mmol; W. Borsche, et al., *Chem. Ber.*, 76, 1099 (1943)) in toluene (20 mL) was refluxed for 0.5 h. Then, toluenesulfonic acid monohydride (10 mg) was added, and the reaction was refluxed with a Dean-Starr trap for 3.5 h. The raction was cooled to room temperature and most solvent was evaporated in vacuum. The residue was flash chromotographed with 100:10:1 chloroform/acetonitrile/methanol to give 196.5 mg (80.3%) brown-yellow solid. Recrystallization with 10% methanol in chloroform giave 173.1 mg off-white solid, m.p. 264°–265° C. (dec). $^1$H NMR (400 MHz, DMSO0d$_6$) δ8.70 (s, 1H), 8.16 (m, 2H), 7.88 (t, J=7.5 Hz, 1H), 7.72 (t, J=Hz, 1H), 7.36 (s, 1H), 6.54 (s, 1H), 5.43 (s, 2H), 5.30, (s, 1H), 1.87 (m, 2H), 0.88 (t, J=7.0 Hz). $^{13}$C NMR (100 MHz, CDCl$_3$) δ172.4, 156.8, 149.9, 147.9, 145.4, 131.6, 130.3, 129.8, 129.0, 128.4, 127.9, 127.6, 119.0, 96.6, 72.3, 65.2, 50.2, 30.2, 7.7 ppm (19 peaks observed). HRMS (FAB) calculated for C$_{20}$H$_{16}$N$_2$O$_4$ (M+1)$^+$ 349.1188, observed 349.1184.

EXAMPLE 11

4-Carbomethoxy-2-hydroxy-de-AB-deoxycamptothecin (14).

To a solution of 8 (1.20 g, 4.12 mmol) in THF (20 mL) at −78° C. was added KHMDS (1.9 g, 9.06 mmol) in THF (10 mL) and Davis' oxazirdine (1.05 g, 4.04 mmol) in THF (10 mL) simultaneously over 20 min. A solution of saturated ammonium chloride (10 mL) was added to the reaction mixture in 10 min, and the reaction was left to warm up to room temperature. The reaction mixture was poured into a brine solution, and the aqueous phase was extracted with chloroform (30 mL×3). The combined organic phase and the extracts were dried over anhydrous magnesium sulfate, filtered, and concentrated. The residue was then loaded onto a flash column, eluted with 30% ethyl acetate in chloroform (500 mL) and 15% acetone in chloroform (1500 mL) to give 15 (246 mg, 19%) and the desired secondary alcohol 14 (707 mg, 56%) as a mixture of diastereomers (1.3:1 ratio from integration of $^1$HNMR.) $^1$H NMR (400 MHz, CDCl$_3$) δ5.40–5.52 (m, 3H), 5.10 (m, 2H), 4.42 & 4.05 (1H), 4.24 (m, 2H), 3.90 (s, 3H), 2.31 (m, 2H) 1.70–1.91 (m, 2H) 1.09 & 0.98 (2t's, J=7.3 Hz, 3H) IR (neat) 3390, 2958, 1732, 1651, 1556, 1435, 1306, 1157, 1090, 748 cm$^{-1}$.

EXAMPLE 12

4-Carbomethoxy-2-oxo-de-AB-deoxycampothecin (16).

A mixture of 14 (595 mg, 1.94 mmol), PDC (2.18 g, 5.80 mmol) and activated 4 Å molecular sieve powder (2.20 g) in methylene chloride (20 mL) was stirred at 0°–5° C. for 4 h. It was then diluted with ethyl acetate (30 mL) and filtered through celite. The flask and the residue was rinsed and washed with 50% ethyl acetate in chloroform (20 mL×5) and the filtrate was concentrated in vacuum to give pure 16 (490.2 mg, 83%). $^1$H NMR (400 MHz, CDCl$_3$) δ5.55 (d, J=17.2 Hz, 1H), 5.24 (d, J=17.2 Hz, 1H), 4.32 (t, J=6.8 Hz, 2H), 3.93 (s, 3H), 3.68 (dd, J=5.2, 8.6 Hz, 1H), 2.97 (t, J=6.8 Hz, 2H), 2.01 (m, 1H), 1.80 (m,1H), 1.04 (t, J=7.4 Hz, 3H). $^{13}$C NMR (100 MHz, CDCl$_3$) δ194.3, 169.5, 164.0, 157.2, 144.6, 137.7, 126.4, 110.2, 65.7, 53.4, 43.6, 42.2, 33.7, 26.1, 11.5 ppm. IR (neat) 2952, 1742, 1658, 1614, 1440, 1300, 1159, 1057 cm$^{-1}$.

EXAMPLE 13

4-Carbomethoxy-deoxycamptothecin (17).

A solution of 16 (601 mg, 0.197 mmol) and 12 (497 mg, 2.36 mmol) in toluene (20 mL) was refluxed for 40 min. Then toluenesulfonic acid monohydrate (20 mg) was added, and the reaction flask was equipped with a Dean-Stark trap. Reflux was continued for 4 h before the reaction was cooled to room temperature. It was concentrated to about 10 mL via vacuum, and filtered. The solid thus obtained was recrystallized from chloroform to give 17 (578 mg 75%), m.p. 300°–302° C.(dec). $^1$H NMR (400 MHz, CDCl$_3$) δ8.38 (s, 1H), 8.11 (d, J=8.4 Hz, 1H), 7.91 (d, J=8.2 Hz, 1H), 7.81 (dt, J=1.2, 7.7 Hz, 1H), 7.66 (t, J=7.5 Hz, 1H), 5.62 (d, J=16.2 Hz, 1H), 5.30 (d, J=16.2 Hz, 1H), 5.28 (s, 2H), 4.12 (s, 3H), 3.78 (dd, J=5.2, 8.7 Hz, 1H), 2.12 (m, 1H), 1.93 (m, 1H), 1.11 (t, J=7.4 Hz, 3H). $^{13}$C NMR (100 MHz, CDCl$_3$) δ170.2, 165.6, 157.2, 151.4, 148.8, 145.1, 144.4, 130.9, 130.6, 130.3, 128.53, 128.48, 128.04, 127.99, 120.5, 108.3, 65.7, 52.9, 50.2, 44.1, 26.0, 11.6 ppm. HRMS calculated for $C_{22}H_{18}N_2O_5$ (M$^+$) 390.1216, observed 390.1231.

EXAMPLE 14

Deoxycamptothecin (18).

A solution of 17 (207.5 mg, 0.531 mmol) in 48% aqueous hydrobromic acid (8 mL) in a sealed tube was heated for 15 h at 140° C. After it was cooled, the reaction mixture was concentrated to near dryness via vacuum. The mixture was then carefully neutralized with sodium hydroxide; 2N) and saturated sodium bicarbonate to pH 6–8. The aqueous mixture was extracted with chloroform (15 mL×10). The combined extracts were dried over anhydrous magnesium sulfate, filtered, and concentrated. The residue was flash chromatographed with 2% methanol in chloroform to give 18 (124.3 mg, 71%). HRMS calculated for $C_{20}H_{16}N_2O_3$ (M+) 332.1161, observed 332.1151.

EXAMPLE 15 dl-Camptothecin (1).

To a solution of 18 (47.8 mg, 0.144 mmol), copper(II) chloride (80 mg) and dimethylamine (100 μl) in DMF (16 mL) was bubbled in oxygen for 7 h. The reaction mixture was concentrated in vacuum to about 5 mL, and was then diluted with water. A solution of saturated ammonium chloride was used to adjusted the pH of the above mixture to about 6, and the resulting mixture was extracted with chloroform (10 mL×10). The combined extracts were dried over anhydrous magnesium sulfate, filtered, and concentrated. The residue was flash chromatographed with 2% methanol in chloroform to give dl-camptothecin (45.5 mg, 91%).

EXAMPLE 16

4-Carbomethoxymethyl-5-carbomethoxy-1,6-cyclopentano-2-pyridone (6).

To the solution of enamine 4 (27.6 g, 195 mmol) in absolute ethanol (200 mL) was added dimethyl-3-chloroglutaconate 7 (*Org. Syn. Coll. Vol. VI*, 505); 41.3 g, 215 mmol) and triethylamine (32 mL, 230 mmol). The reaction was stirred at room temperature for 65 h. The reaction mixture was concentrated to near dryness. Trituration of the residue with dry ether (50 mL) afforded 6 as a white solid (47.8 g, 92%). $^1$H NMR (CDCl$_3$) δ6.21 (s, 1H), 4.11 (t, J=7.4 Hz, 2H), 3.74 (s, 3H), 3.73 (s, 2H), 3.66 (s, 3H), 3.44 (t, J=7.9 Hz, 2H), 2.16 (quintet, J=7.6 Hz, 2H). $^{13}$C NMR (CDClD3) δ170.9, 165.8, 161.0, 157.4, 147.1, 120.1, 106.5, 52.1, 51.6, 49.1, 41.1, 34.7, 20.6. IR (neat) 2953, 1734, 1716, 1656, 1652, 1520, 1436, 1294, 1203 cm$^{-1}$.

EXAMPLE 17

4-(1-Carbomethoxypropyl)-5-carbomethoxy-1,6-cyclopentano-2-pyridone (7).

To a solution of pyridone 6 (47.0 g, 177 mmol) in any DME (700 mL) at –70° C. was added potassium tertbutoxide (20.8 g, 186 mmol). After 20 min, EtI (50.3 g, 354 mmol) was added and the solution was allowed to warm to room temperature and stirred for 30 h. The reaction mixture was then poured to brine (300 mL) and the aqueous layer extracted with CH$_2$Cl$_2$ (4×200 mL). The combined organic phase and the extracts were dried (MgSO$_4$), filtered and concentrated. The semi-solid residue was then recrystallized (EtOAc) to give 7 as pale yellow-green sold (36.54 g, 2 crops). The mother liquor was subjected to flash chromatography with ethyl acetate to afford an additional 11.2 g (total yield of 91%), m.p. 92.5°–94.0° C. $^1$H NMR (CDCl$_3$) δ6.35 (s, 1H), 4.13 (dt, J=1.2, 7.5 Hz, 2H), 3.99 (t, J=7.2 Hz, 1H), 3.80 (s 3H), 3.64 (s, 3H), 3.39 (dt, J=2.6, 8.0 Hz, 2H), 2.17 (quintet, J=7.6 Hz, 2H), 2.05 (m, 1H), 1.73 (m, 1H), 0.91 (t, J=7.4 Hz, 3 h). $^{13}$C NMR (CDCl$_3$) δ173.0, 166.1, 161.1, 156.3, 151.6, 117.2, 107.0, 53.1, 51.7, 49.8, 49.2, 34.5, 25.4, 20.7, 12.4. IR (neat) 1741, 1710, 1668 cm$^{-1}$.

EXAMPLE 18

4-Carbomethoxy-de-AB-deoxycamptothecin (8).

A mixture of ester 7 (5.01 g, 17.1 mmol), paraformaldehyde (3.08 g), concentrated H$_2$SO$_4$ (1 mL) and water (1 mL) in dioxane (25 mL) in a sealed thick wall tube was heated at 107° C. for 24 h. The resulting solution was then poured to brine (60 mL) and extracted with CH$_2$Cl$_2$ (4×50 mL). The combined extracts were dried (MgSO$_4$), filtered, and concentrated to a pale yellow oil which eventually solidified upon standing. $^1$H NMR (CDC$_3$) δ5.48 (d, J=5.8 Hz, 1H), 5.13 (d, J=5.8 Hz, 1H), 4.34 (dd, J=5.1, 9.1 Hz, 1H), 4.19, (dt, J=2.9, 7.6 Hz, 2H), 3.85 (s, 3H), 3.48 (dt, J=3.6, 7.9 Hz, 2H), 2.22 (quintet, J=7.6 Hz, 2H), 1.65–2.01 (m, 2H), 1.08 (t, J=7.6 Hz, 3H). $^{13}$C NMR (CDCl$_3$) δ171.3, 165.2, 157.9, 167.0, 147.3, 118.5, 104.9, 65.0, 52.0, 49.5, 44.3, 34.8, 25.3, 20.7, 11.95. IR (neat) 1734, 1713, 1650 cm$^{-1}$.

EXAMPLE 19

De-AB-deoxycampothecin (9).

A mixture of tricycle 8 in aqueous HBr (48%, 50 mL) was heated in a sealed tube at 105° C. for 18 h. The resulting solution was then poured into brine (60 mL) and extracted with CH$_2$Cl$_2$ (4×50 mL). The combined extracts were dried (MgSO$_4$), filtered, and concentrated. The residue was then subjected to flash chromatograPhY (50/50/1 CHCl$_3$/EtOAc/MeOH) to afford 9 as an off-white solid (2.11 g, 53%), m.p. 146.0°–147.5° C. $^1$H NMR (CDCl$_3$) δ5.98 (s, 1H), 5.38 (d, J=5.7 Hz, 1H), 5.20 (d, 3=5.$^7$ Hz, 1H), 4.12 (t, J=7.3 Hz, 2H), 3.35 (t, J=6.6 Hz, 1H), 3.08 (t, J=7.7 Hz, 2H), 2.21 (quintet, J=7.4 Hz, 2H), 1.80–19.8 (m, 2H), 0.99 (t, J=7.4 Hz, 3H). $^{13}$C NMR (CDCl$_3$) δ171.4, 158.5, 150.5, 146.6, 117.2, 100.2, 66.1, 48.6, 45.8, 31.8, 25.1, 21.5, 11.3. IR (neat) 1739, 1651, 1574 cm$^{-1}$.

EXAMPLE 20

2-Hydroxy-de-AB-camptothecin (10).

A mixture of 9 (778 mg, 3.33 mmol) and SeO$_2$ (1.85 g, 16.7 mmol) in 20 mL of 95% dioxane were heated together in a sealed tube at 160° C. for 4 h. The solution was then poured into water and extracted with CH$_2$Cl$_2$ (4×30 mL). The combined extracts was dried (MgSO$_4$), filtered, and concentrated. The dark solid residue was then chromatographed (3:1 CHCl$_3$/acetone, 300 mL) then (30:20:1 CHCl$_3$/acetone/MeOH, 500 mL) to afford 10 as a yellow solid (377.4mg, 43%).

The diasteromeric ratio is about 1/1. $^1$H NMR (DMSO-d$_6$ with 1 small drop of D$_2$O) δ6.51 (DMSO-d$_6$ with 1 small drop of D2O) δ6.51 (s, 1H), 5.25, (dd, J=15.4, 19.0 Hz, 2H), 5.13 (t, J=7.0 Hz, 1H), 4.08 (m, 1H), 3.83 (m, 1H), 2.42 (m, 1H), 1.93 (m, 1H), 1.76 (m, 2H), 0.82 (t, J=7.1 Hz, 3H). $^{13}$C NMR (DMSO-d$_6$) δ172.59, 172.54, 156.87, 152.94, 152.90, 149.83, 149.78, 116.33, 97.37, 72.71, 72.09, 72.04, 71.94, 65.16, 59.68, 45.62, 31.25, 31.19, 30.30, 30.26, 7.66 ppm (21 peaks observed). IR (KBr) 3392, 1741, 1652, 1570 cm$^{-1}$. HRMS calc'd for C$_{13}$H$_{15}$NO$_5$ (M$^+$): 265.0950. Found: 265.0952.

EXAMPLE 21

2-Oxo-de-AB-camptothecin (17).

To the suspension of 10 (356.1 mg, 1.34 mmol) and 4 Å molecular sieves (activated powder, 1.50 g) in CH$_2$Cl$_2$ (15 mL) at 0° C. was added pyridinium dichromate (1.01 g, 2.68 mmol). After 3.5 h, 30 mL of EtOAc was added to the mixture, and the slurry was filtered through a plug of silica gel and celite. Evaporation of the filtrate and chromatography (1:1 CHCl$_3$/EtOAc) gave 11 (159.6 mg, 45%). $^1$H NMR (CDCl$_3$) δ7.23 (s, 1H), 5.68 (d, J=7.1 Hz, 1H), 5.25 (d, J=7.1 Hz, 1H), 4.35 (t, J=6.8 Hz, 2H), 3.65 (s, 1H), 2.97 (t, J=6.8 Hz, 2H), 1.82 (m, 2H), 0.99 (t, J=7.4 Hz, 3H). $^{13}$C NMR (CDCl$_3$) δ196.0, 173.3, 157.7, 149.3, 139.9, 124.5, 100.8, 72.3, 66.3, 42.2, 33.7, 31.8, 7.7. IR (neat) 3404, 1736, 1656, 1598 cm$^{-1}$. HRMS calc'd for C$_{13}$H$_{13}$NO$_5$ (M$^+$): 263.0794. Found: 263.0809.

EXAMPLE 21 dl-Camptothecin (1).

A suspension of 11 (185.2 mg, 0.704 mmol) and amino toluidine 14 (*Chem. Ber.*, 76, 1099 (1943); 178 mg, 0.844 mmol) in toluene (20 mL) was refluxed for 0.5 h. Then, p-TsOH (10 mg) was added, and the reaction was refluxed with a Dean-Stark trap for 3.5 h. The solution was cooled to room temperature and solvent was removed. Column chromatography (100:10:1 CHCl$_3$/MeCH/MeOH) gave 196.5 mg (80%) of 1 as a tan solid. Recrystallization (10% MeOH/CHCl$_3$) gave 173.1 mg of 1 as an off-white solid, mp 264°–265° C. (dec.) $^1$H NMR (DMSO-d$_6$) δ8.70 (s, 1H) 8.16 (m, 2H), 7.88 (t, J=7.5 Hz, 1H), 7.72 (t, J=7.3 Hz, 1H), 7.36 (s, 1H), 6.54 (s, 1H), 5.43 (s, 2H), 5.30 (s, 1H), 1.87 (m, 2H), 0.88 (t, J=7.0 Hz). $^{13}$C NMR (CDCl$_3$) δ172.4, 156.8, 149.9, 147.9, 145.4, 131.6, 130.3, 129.8, 129.0, 128.4, 127.9, 127.6, 119.0, 96.6, 72.3, 65.2, 50.2, 30.2, 7.7 ppm (19 peaks observed). IR (KBr) 3271, 1755, 1651 1583 cm$^{-1}$. HRMS calc'd for C$_{20}$H$_{16}$N$_2$O$_4$ (M$^+$1): 349.1188. Found: 349.1184.

EXAMPLE 22

14-Carbomethoxy-2-hydroxy-de-AB-deoxycamptothecin (15).

To an oxygenated solution of 10 (291 mg, 1.00 mmol) and 0.38 mL (2.20 mmol) of P(OEt)$_3$ in 20 mL of THF at −70° C. was added NaHMDS (1.1 mL, 1.1 mmol) over 2 min The solution was warmed to room temperature over 7 h and was quenched with saturated NH$_4$Cl (10 mL). The reaction mixture was extracted with CHCl$_3$ (30 mL×3) and the extracts were dried (MgSO$_4$), filtered, and concentrated. The residue was then loaded to a flash column, eluted with 9:1 CHCl$_3$/MeOH to give alcohol 15 (230 mg, 75%) as a mixture of diastereomers (1.3:1 ratio from integration of $^1$H NMR). $^1$H NMR (CDCl$_3$) δ5.40–5.52 (m, 3H), 5 10 (m, 2H), 4.42 & 4.05 (1H), 4.24 (m, 2H), 3.90 (s, 3H), 2.31 (m, 2H), 1.70–1.91 (m, 2H), 1.09 & 0.98 (2 t's, J=7.3 Hz, 3H). IR (neat) 3390, 2958, 1732, 1651 cm$^{-1}$. HRMS calc'd for C$_{15}$H$_{17}$NO$_6$ (M$^+$): 307.1056. Found: 307.1062.

EXAMPLE 23

4-Carbomethoxy-2-oxo-de-AB-deoxycamptothecin (16).

A mixture of alcohol 15 (595 mg, 1.94 mmol), PDC (2.18 g, 5.80 mmol) and activated 4 Å molecule sieve powder (2.20 g) in CH$_2$Cl$_2$ (20 mL) was stirred at 0°–5° C. for 4 h. It was then diluted with EtOAc (30 mL) and filtered through celite. The flask and the residue was rinsed and washed with 1:1 EtOAc/CHCl$_3$ (20 mL×5) and the filtrate was concentrated to give pure 16 (490.2 mg, 83%). $^1$H NMR (CDCl$_3$) δ5.55 (d, J=17.2 Hz, 1H), 5.24 (d, J=17.2 Hz, 1H), 4.32 (t, J=6.8 Hz, 2H), 3.93 (s, 3H), 3.68 (dd, J=5.2, 8.6 Hz, 1H), 2.97 (t, J=6.8 Hz, 2H), 2.01 (m, 1H), 1.80 (m, 1H), 1 04 (t, J=7.4 Hz, 3H) $^{13}$C NMR (CDCl$_3$) δ194 3, 169.5, 157.2, 144.6, 137.7, 126.4, 110.2, 65.7, 53.4, 43.6, 42.2, 33.7, 26.1, 11.5. IR (neat) 1742, 1658 cm$^{-1}$. HRMS calc'd for C$_{15}$H$_{15}$NO$_6$ (M$^+$): 305.0899. Found: 305.0911.

EXAMPLE 24

Benzylidene (17).

To a solution of 587 mg (2.0 mmol) of ester 10 and 0.19 mL (1.9 mmol) of benzaldehyde in 15 mL of THF at −70° C. was added 2.2 mL (2.2 mmol) of NaHMDS (1M in THF). The orange solution was allowed to warm to room temperature over 16 h before it was quenched with 15 mL of 5% HCl. After an additional 2 h, the mixture was extracted with 4:1 CHCl$_3$/MeOH (5×20 mL), dried (MgSO$_4$) and concentrated. The resulting yellow solid was triturated with THF to afford 624 mg (90%) of 17 as a white solid. $^1$H NMR (CDCl$_3$) δ7.21 (m, 6H), 5.32, (d, J=16.1 Hz, 1H), 5.01 (d, J=16.1 Hz, 1H), 3.98 (t, J=7.4 Hz, 2H), 3.63 (m, 1H), 3.04 (dt, J=2.3, 6.2 Hz, 2H), 1.88 (m, 1H), 1.68 (m, 1H), 0.89 (t, J=7.4 Hz, 3H). $^{13}$C NMR (CDCl$_3$/CD$_3$OD) δ171.4, 167.1, 157.6, 146.9, 145.4, 135.4, 132.5, 132.5, 128.8, 117.9, 107.9, 65.4, 46.6, 44.3, 27.7, 25.4, 11.4. IR (CHCl$_3$) 3500–2400, 1739, 1717, 1622, 1574, 1531, 1214 cm$^{-1}$. HRMS calc'd for C$_{21}$H$_{19}$NO$_5$ (M$^+$): 365.1302. Found: 365.1311.

EXAMPLE 25

Keto acid (18).

A −70° C. solution of 7.0 mg (0.020 mmol) of 17 in 10 mL of MeOH and 10 mL of CH$_2$Cl$_2$ was subjected to O$_3$ for 10 min before the addition of Me$_2$S. The mixture was allowed to warm to room temperature over 12 h then evaporated to leave 5.6 mg (96%) of ketone 18 which was used without further purification. $^1$H NMR (DMSO-d$_6$/CDCl$_3$) δ5.58 (d, J=17.2 Hz, 1H), 5.21 (d, J=17.2 Hz, 1H), 4.29 (t, J=7.2 Hz, 2H), 3.80 (m, 1H), 2.97 (t, J=7.2 Hz, 2H), 2.11, (m, 1H), 1.84 (m, 1H), 0.91 (t, J=7.2 Hz, 3H). IR (neat) 3426, 1738, 1712. 1659 cm$^{-1}$.

EXAMPLE 26

4-Carbomethoxy-2-oxo-de-AB-deoxycamptothecin (16).

A solution of 291 mg (1.0 mmol) of keto acid 17 in 3 mL of benzene and 1 mL of MeOH was treated with 0.65 mL of TMSCHN$_2$ (2M in hexane). After stirring for 3 h the solvents were evaporated and the residue was chromatographed (95:5 CHCl$_3$/MeOH) to afford 287 mg (94%) of ester 16. $^1$H NMR (CDCl$_3$) δ5.55 (d, J=17.2 Hz, 1H), 5.24 (d, J=17.2 Hz, 1H), 4.32 (t, J=6.8 Hz, 2H), 3.93 (s, 3H), 3.68 (dd, J=5.2, 8.6 Hz, 1H), 2.97 (t, J=6.8 Hz, 2H), 2.01 (m, 1H), 1.80 (m, 1H), 1.04 (t, J=7.4 Hz, 3H). $^{13}$C NMR (CDCl$_3$) δ194.3m, 169.5, 164.0, 157.2, 144.6, 137.7, 126.4, 110.2, 65.7, 53.4, 43.6, 42.2, 33.7, 26.1, 11.5. IR (neat) 1742, 1658 cm$^{-1}$.

EXAMPLE 27

14-Carbomethoxy-20-deoxycamptothecin (19).

A solution of keto ester 16 (601 mg, 1.97 mmol) and amine 14 (*Chem. Ber.*, 76, 1099 (1943); 497 mg, 2.36 mmol) in toluene (20 mL) was refluxed for 40 min. TsOH (20 mg) was added, the reaction flask was equipped with a Dean-Stark trap, and the whole was refluxed for 4 h before the reaction was cooled to room temperature. The mixture was concentrated (10 mL) and the resulting solid was filtered and recrystallized (CHCl$_3$) to give 19 (578 mg, 75%), mp 300°–302° C. (dec.) $^1$H NMR (CDCl$_3$) δ8.38 (s, 1H), 8.11 (d, J=8.4 Hz, 1H), 7.91 (d, J=8.2 Hz, 1H), 7.81 (dt, J=1.2, 7.7 Hz, 1H), 7.66 (t, J=7.5 Hz, 1H), 5.62 (d, J=16.2 Hz 1H), 5.30 (d, J=16.2 hz, 1H), 5.28 (s 2H, 4.12 (s, 3H), 3.78 (dd, J=5.2, 8.7 Hz, 1H), 2.12 (m, 1H), 1.93 (m, 1H), 1.11 (t, J=7.4 Hz, 3H). $^{13}$C NMR (CDCl$_3$) δ170.2, 165.6, 157.2, 151.4, 148.8, 145.1, 144.4, 130.9, 130.6, 130.3, 128.53, 128.48, 128.04, 127.99, 120.5, 108.3, 65.7, 52.9, 50.2, 44.1, 26.0, 11.6. IR (KBr) 2930, 1732, 1652, 1616, 1452 cm$^{-1}$. HRMS calc'd for C$_{22}$H$_{18}$N$_2$O$_5$ (M$^+$): 390.1216. Found: 390.1231.

EXAMPLE 28

20-Desoxycampothecin (20).

A solution of ester 19 (207.5 mg, 0.531 mmol) in 48% aqueous HBr (8 mL) in sealed tube was heated for 15 h at 140° C. After it was cooled, the reaction mixture was concentrated to near dryness via vacuum. The mixture was then carefully neutralized with 2N NaOH and saturated NaHCO$_3$ to pH 7.5. The aqueous mixture was extracted with CHCl$_3$ (15 mL×10) and the combined extracts were dried (MgSO$_4$), filtered, and concentrated. The residue was flash chromatographed (49:1 CHCl$_3$/MeOH) to give 20 (124.3 mg, 71%). $^1$H NMR (400 MHz, CDCl$_3$) δ8.39 (s 1H), 8.21 (d, J=8.4 Hz, 1H), 7.93 (d, J=7.0 Hz, 1H), 7.83 (dt, J=1.4, 16.9 Hz, 1H), 7.66 (dr, J=1.0, 7.5 Hz, 1H), 7.19 (s, 1H), 5,57 (d, J=16.3 Hz, 1H), 5.39 (d, J=16.3 Hz, 1H), 5.29 (s, 2H), 3.62 (t, J=6.6 Hz, 1H), 2.09 (m, 2H), 1.09 (t, J=7.4 Hz, 3H). $^{13}$C NMR (100 MHz, CDCl$_3$) δ170.9, 157.9, 152.4, 148.9, 147.2, 146.0, 131.2, 130.7, 129.7, 128.6, 128.2, 128.1, 120.7, 99.8, 66.1, 50.0, 45.9, 25.4, 11.4. HMRS calc'd for C$_{20}$H$_{16}$N$_2$O$_3$ (M$^+$): 332.1161. Found: 332. 1151.

EXAMPLE 29 dl-Camptothecin (1).

To a solution of 20(47.8 mg, 0.144 mmol), CuCl$_2$ (80 mg) and diethylamine (100 82 l) in DMF (16 mL) was bubbled in oxygen for 7 h. The reaction mixture was concentrated in vacuo to about 5 mL, and was then diluted with water. A solution of saturated NH$_4$Cl was used to adjusted the pH to 6, and the resulting mixture was extracted with chloroform (10×10 mL). The combined extracts were dried (MgSO$_4$) filtered, and concentrated. The residue was flash chromatographed (98:2 CHCl$_3$/MeOH) to give 1 (45.5 mg, 91%).

EXAMPLE 30

14-Carbomethoxy-10-methoxy-20-deoxycamptothecin (22).

A solution of amino acetal 21 (*J. Med. Chem.*, 23, 554 (1980); 329 mg., 1.69 mmol) and ketone 16 (429 mg, 1.41 mmol) in 15 mL of toluene were heated together for 30 min before the addition of 10 mg of p-TsOH. The resulting red solution was heated at reflux with removal of water for 3.5 h. The solvent was removed and the residue was chromatographed (99:1 CHCl$_3$/MeOH) then triturated with a 2:1 ether/THF solution to afford 444 mg (75%) of ester 22 as an off-white solid. $^1$H NMR (CDCl$_3$) δ8.24 (s, 1H), 7.99 (d, J=9.3 Hz, 1H), 7.44 (dd, J=2.8, 9.3 Hz, 1H), 7.13 (d, J=2.7, 1H), 5.61 (d, J=16.3 Hz, 1H), 5.29 (d, J=16.2 Hz, 1H), 5.24 (s, 2H), 4.15 (s, 3H), 3.97 (s, 3H), 3.85 (m, 1H), 2.13 (m, 1H), 1.88 (m, 1H), 1.10 (t, J=7.5 Hz, 3H). $^{13}$C NMR (CDCl$_3$) δ170.3, 165.7, 159.3, 157.1, 145.0, 144.9, 131.6, 129.4, 129.1, 123.7, 119.6, 105.0, 65.6, 55.7, 52.8, 50.1, 43.9, 25.9, 11.5. IR (KBr) 1731, 1651 cm$^{-1}$. HRMS calc'd for C$_{23}$H$_{21}$N$_2$O$_6$ (M+H): 421.1477. Found: 421.1421.

EXAMPLE 31

10-Hydroxycamptothecin (24).

A solution containing 24.1 mg (0.057 mmol) of ester 22 in 2 mL of 48% HBr was heated at 140° C. in a sealed tube for 15 h. The solvent was evaporated and the residue was made neutral by the addition of sat'd NaHCO$_3$ solution. The aqueous solution was extracted with 4:1 CHCl$_3$/MeOH (5×10 mL) and dried (MgSO$_4$). Evaporation of the solvent gave crude 10-hydroxy-20-deoxycamptothecin (23) which was immediately dissolved in 2 mL of DMF. After the addition of CuCl$_2$ (40 mg) and Me$_2$NH (50 μL), O$_2$ was passed through the solution for 8 h. The mixture was then diluted with water (3 mL) and sat'd NH$_4$Cl was added to adjust the pH to 6. Extraction with CHCl$_3$ (5×10 mL), drying (MgSO$_4$), chromatography (9:1 CHCl$_3$/MeOH), and recyrstallization (13% MeOH/CHCl$_3$ and EtOAc) afforded 17.3 mg (83%) of 24, mp 266°–268° C. (lit. [*J. Med. Chem.*, 23,554 (1980)]265°–268° C.).

EXAMPLE 32

Benzylic alcohol (26).

To a 70° C. solution of 860 mg (4.75 mmol) of 5-methoxy-2-nitrobenzaldehyde (25) in 20 mL of THF was added 6.65 mL (6.65 mmol) of vinylmagnesium bromide. After stirring for 3.5 h, the mixture was quenched with 20 mL of 0.010N HCl and diluted with 100 mL of ether (3×25 mL). The yellow extracts were dried (MgSO$_4$) and concentrated to afford 993 mg (100% ) of alcohol 26. $^1$H NMR (CDCl$_3$) δ7.95 (d, J=9.1 Hz, 1H), 7.19 (d, J=2.8 Hz, 1H), 6.70 (dd, J=2.8, 9.1 Hz, 1H), 5.96 (m, 1H), 5.84 (d, J=5.2 Hz, 1H), 5.30 (dt, J=1.3, 17.5, Hz, 1H), 3.84 (s, 3H), 3.40 (bs, 1H). $^{13}$C NMR (CDCl$_3$) δ163.8, 141.4, 140.6, 138.0, 127.5, 115.8, 113.1 (2 lines), 69.7, 55.8. IR (neat) 3437, 1613 cm$^{-1}$. HRMS calc'd for C$_{10}$H$_{11}$NO$_4$ (M+): 209.727. Found: 209.0699.

EXAMPLE 33

Enone (27).

Freshly prepared Jones reagent (1.1 mL, 2.67M) was added dropwise to 418 mg (2.0 mmol) of alcohol 26 in 4 mL of acetone at room temperature. After 10 min, ice water (5 mL) was added followed by 1 ml of sat'd NaHSO$_3$. The resulting mixture was extracted with ether (4×10 mL) then filtered through Florisil. Evaporation of the solvent left 363 mg (88%) of ketone 27 as an off-colored oil. $^1$H NMR (CDCl$_3$) δ8.08 (d, J=9.1 Hz, 1H), 6.99 (dd, J=2.8, 9.0 Hz, 1H), 6.75 (d, J=2.8 Hz, 1H), 6.59 (m, 1H), 5.97 (d, J=10.6

Hz, 1H), 5.78 (d, J=11.6 Hz, 1H), 3.85 (s, 3H). $^{13}$C NMR (CDCl$_3$) δ193.3, 164.1, 139.2, 138.1, 136.5, 130.9, 126.9, 115.3, 113.4, 56.2. IR (neat) 1681 cm$^{-1}$. HRMS calcd for C$_{10}$H$_9$NO$_4$ (M+): 207.0571. Found: 207.0535.

EXAMPLE 34

5-Methoxy-2-aminopropiophenone (28). A solution of 207 mg (1.0 mmol) of nitro enone 27 in 3 mL of abs EtOH containing 10 mg of 10% Pd(c) was stirred under an atmosphere of H$_2$ for 4 h. After this time, the mixture was filtered through Celite and the solvent was evaporated to afford pure amino ketone 28 as a white solid, mp 57°–58° C. (lit. [*Helv. Chem. Acta*, 37, 1805 (1954) mp 58° C.). $^1$H NMR (CDCl$_3$) δ7.25 (d, J=1.2 Hz, 1H), 6.96 (dd, J=1.2, 8.9 Hz, 1H), 6.63 (d, J=9.6 Hz, 1H), 3.77 (s, 3H), 2.96 (q, J=7.2 Hz, 2H), 1.60 (bs, 2H), 1.22 (t, J=7.2 Hz, 3H). $^{13}$C NMR (CDCl$_3$) δ203.5, 150.2, 144.7, 122.7, 118.7, 117.9, 113.9, 56.0, 32.4, 8.6. IR (neat) 3469, 3352, 1659 cm$^{-1}$.

EXAMPLE 35

14-Carbomethoxy-7-ethyl-10-methoxy-20-deoxycamptothecin (29).

A solution of amino ketone 28 (179 mg., 1.00 mmol) and tricyclic ketone 17 (244 mg, 0.800 mmol) in 10 mL of toluene were heated together for 30 min before the addition of 10 mg of p-TsOH. The resulting red solution was heated at reflux with removal of water of 7.25 h. The solvent was removed and the residue was chromatographed (9:1 CHCl$_3$/MeOH) then triturated with 2:1 ether/THF solution to afford 283 mg (79%) of ester 29 as an off-white solid. $^1$H NMR (CDCl$_3$) δ8.02 (d, J=9.2 Hz, 1H), 7.45 (dd, J=2.7, 9.2 Hz, 1H), 7.29 (d, J=2.7 Hz, 1H), 5.64 (dd, J=16.3 Hz, 1H), 5.31 (d, J=16.3 Hz, 1H), 5.22 (s, 2H), 4.11 (s, 3H), 4.02 (s, 3H), 3.79 (m, 1H), 3.15 (q, J=7.7 Hz, 2H), 2.10 (m, 1H), 1.94 (m, 1H), 1.38 (t, J=7.7 Hz, 3H), 1.11 (t, J=7.5 Hz, 3H). $^{13}$C NMR (CDCl$_3$) δ170.3, 165.7, 159.2, 157.3, 148.4, 145.8, 145.4, 145.1, 143.4, 132.6, 128.1, 127.2, 122.6, 119.4, 101.2, 65.6, 55.7, 52.8, 49.5, 44.0, 25.9, 23.1, 13.5, 11.6. HRMS calc'd for C$_{25}$H$_{25}$N$_2$O$_6$ (M+H): 448.9835. Found: 448.9818.

EXAMPLE 36

7-Ethyl-10-hydroxycamptothecin (31).

A solution containing 44.8 mg (0.10 mmol) of ester 29 in 5 mL of 48% HBr was heated at 140° C. in a sealed tube for 15 h. The solvent was evaporated and the residue was made neutral by the addition of sat'd NaHCO$_3$ solution. The aqueous solution was extracted with 4:1 CHCl$_3$/MeOH (5×10 mL) and dried (MgSO$_4$). Evaporation of the solvent gave crude 7-ethyl-10-hydroxy-20-deoxycamptothecin (30) which was immediately dissolved in 4 mL of DMF. After the addition of CuCl$_2$ (80 mg) and Me$_2$NH (100 μL), O$_2$ was passed through the solution for 8 h. The mixture was then diluted with water (10 mL) and sat'd NH$_4$Cl was added to adjust the pH to 6. Extraction with CHCl$_3$ (5×15 mL), drying (MgSO$_4$) and chromatography (9:1 CHCl$_3$/MeOH) afforded 17.3 mg (83%) of 31. This material had spectroscopic properties ($^1$H NMR and IR) identical to the previously reported (+)-isomer, mp 214°–217° C. (lit. [*Chem. Pharm. Bull.*, 39, 1446 (1991)] mp 214° C.).

EXAMPLE 37

Acetate (40).

To 32.00 g (0.20 mol) acetate 39 in 125 ml benzene was added 29.40 g (0.20 mol) Meldrum's acid and 5.40 ml (0.04 mol) triethylamine. The resultant solution was heated to reflux under nitrogen for 9 h, cooled to ambient temperature and triturated with ether providing 25.80 g 40 as a brown solid (47%). The mother liquors were concentrated in vacuo and subjected to column chromatography (2:1 hexane/ethyl acetate to ethyl acetate) providing a black tar which was triturated with ether providing an additional 1.80 g 40 (total yield: 50%). $^1$H NMR (CDCl$_3$) δ, 10.20 (br s, 1H), 6.52 (dd, J=1.4; 6.9 Hz, 1H), 3.90 (m 1H), 3.82 (m, 1H), 2.53 (m, 1H), 2.17 (m, 1H), 2.07 (s, 3H), 1.71 (s, 3H), 1.69 (s, 3H); $^{13}$C NMR (CDCl$_3$) δ, 171.22, 169.33, 166.48, 161.47, 103.35, 81.81, 74.59, 47.10, 28.64, 26.74, 26.20, 20.32; IR (film), 3303, 1737, 1676, 1586 cm$^{-1}$; HRMS calc'd for C$_{12}$H$_{15}$NO$_6$ 269.0899, found 269.0894.

EXAMPLE 38

Enamine (41).

To a slurry of 27.50 g (0.10 mol) of acetate 40 in 150 ml methanol was added 30.4 ml (0.13 mol) of sodium methoxide (25 wt % in methanol). The resultant black solution was heated to reflux for 17 h, concentrated in vacuo and acidified to pH 4 via careful addition of 1M HCl. The aqueous solution was extracted with dichloromethane (5×75 ml), dried over Na$_2$SO$_4$ and concentrated in vacuo providing 13.0 g (81%) enamine 41 as a light brown solid. $^1$H NMR (CDCl$_3$) δ7.60 (br s, 1H), 4.72 (s, 1H), 4.67 (m, 1H), 3.65 (s, 3H), 3.61 (m, 1H), 2.77 (d, J=4.6 Hz, 1H), 2.28 (m, 1H), 1.93 (m, 1H); $^{13}$C NMR (CDCl$_3$) δ,171.29, 166.48, 76.68, 73.77, 50.30, 44.43, 32.01; IR (film), 3370, 3000, 1654, 1627, 1615 cm$^{-1}$; HRMS calc'd for C$_7$H$_{12}$NO$_3$ (M+1) 158.0817, found 158.0821.

EXAMPLE 39

Bicyclic Pyridone (42).

To 12.9 g (82.2 mmol) 41 in 100 ml abs. ethanol under nitrogen was added 17.4 g (90.4 mmol) dimethyl-3-chloroglutaconate and 13.7 ml (98.6 mmol) triethylamine. The reaction mixture was stirred at ambient temperature for 72 h, and concentrated in vacuo. The residue was dissolved in 300 ml chloroform and washed with 1M HCl (2×100 ml), 100 ml NaHCO$_{3(sat)}$, 100 ml brine, dried over MgSO$_4$, and concentrated in vacuo to a black oil. Column chromatography (20 to 30% acetone/chloroform) provided 16.9 g (73%) 42 as a red viscous oil which solidified to a tan solid on standing. $^1$H NMR (CDCl$_3$) δ,6.32 (s, 1H), 5.49 (m, 1H), 4.30–4.16 (m, 2H), 4.35 (d, J=2.3 Hz, 1H), 3.84 (s, 3H), 3.88–3.79 (m, 1H), 3.70 (s, 3H), 3.74–3.65 (m, 1H), 2.46–2.28 (m, 2H); $^{13}$C NMR (CDCl$_3$) δ, 170.32, 166.34, 160.26, 157.30, 146.35, 121.38, 106.60, 73.90, 51.97, 51.90, 47.41, 40.74, 28.87; IR (film), 3245, 2959, 1732, 1640, 1577 cm$^{-1}$; mp 121°–123° C.; HRMS calc'd for C$_{13}$H$_{15}$N$_1$O$_6$ 281.0899, found 281.0892.

EXAMPLE 40

Mono-methylated Pyridone (43). To 204 mg (0.73 mmol) 42 in 7 ml THF/7 ml toluene under nitrogen at −78° C. was added 1.52 ml (1.52 mmol) LiHMDS (1.0 M/hexane). The solution was immediately warmed to 0° C. for 1.5 h, cooled to −78° C. and 50 μl (0.80 mmol) iodomethane (passed through a plug of basic alumina prior to use) was added. The reaction was allowed to warm to ambient temperature over 18 h, quenched with 20 ml 1M HCl and extracted with chloroform (4×25 ml). The combined organic layers were dried over MgSO$_4$, and concentrated in vacuo to a red oil which was subjected to column chromatography (25% acetone/chloroform) providing 178 mg (81%) 43 as an inseparable mixture of diastereomers. $^1$H NMR (CDCl$_3$) δ, 6.40 (s, 1H), 5.30–5.29 (m, 1H), 4.23–4.11 (m, 3H), 4.01 (br s, 1H), 3.82 (s, 3H), 3.62 (s, 3H), 2.33–2.26 (m, 2H), 1.43 (d, J=7.2 Hz, 3H); $^{13}$C NMR (CDCl$_3$) δ, 173.20, 167.07, 160.68, 156.89, 152.04, 118.89, 106.83, 74.22, 52.29, 47.65, 43.17, 28.95, 16.65; IR (film), 3308, 2951, 1733, 1717, 1652 cm$^{-1}$.

EXAMPLE 41

Tricyclic Pyridone (44).

To 46 mg (0.16 mmol) 43 in 3 ml dioxane in a pressure tube was added 24 mg (0.79 mmol) paraformaldehyde and 4 pipette drops H$_2$SO$_4$. The reaction vessel was sealed and heated to 110° C. for 24 h, cooled to ambient temperature and diluted with 1M HCl. The aqueous mixture was extracted chloroform (5×10 ml), dried over MgSO$_4$ and concentrated in vacuo to a rust colored oil. Column chromatography (20% acetone/chloroform) provided 25 mg (54%) 43 as an amber oil. $^1$H NMR (CDCl$_3$) δ, 5.55 (d, J=15.9 Hz, 1H), 5.43–5.38 (m, 1H), 5.12 (d, J=15.9 Hz, 1H), 4.30–4.11 (m, 3H) 3.93 (s, 3H), 2.42–2.27 (m, 2H), 1.53 (d, J=7.4 Hz, 3H); $^{13}$C NMR (CDCl$_3$) δ, 172.29, 166.04, 157.50, 157.34, 147.58, 120.21, 104.75, 74.30, 64.39, 52.87, 48.13, 38.69, 28.83, 16.77; IR (film), 3432, 2954, 1738, 1715, 1651 cm$^{-1}$.

EXAMPLE 42

Bromide (45). To 2.00 g (7.12 mmol) 42 in 50 ml DMF under nitrogen was added 1.27 g (7.12 mmol) N-bromosuccinimide. The solution was allowed to stir at ambient temperature for 20 h and concentrated in vacuo. The residue was dissolved in 75 ml dichloromethane and washed with 50 ml water, and 50 ml brine. The organic layer was dried over MgSO$_4$ and concentrated in vacuo to a red oil which solidified on standing. Column chromatography (50 to 75% ethyl acetate/hexane) provided 2.26 g (88%) 45 as a pale yellow solid. $^1$H NMR (CDCl$_3$) δ, 5.35 (d, J=6.0 Hz, 1H), 4.20 (m, 2H), 4.10 (d, J=17.1 Hz, 1H), 4.04 (d, J=17.1 Hz, 1H), 3.79 (s, 3H), 3.64 (s, 3H), 2.38–2.33 (m, 1H), 2.28–2.21 (m, 1H); $^{13}$C NMR (CDCl$_3$) δ, 169.20, 165.80, 156.64, 154.72, 144.62, 119.65, 107.43, 73.89, 52.41, 52.05, 48.84, 40.79, 29.03; IR (film), 3380, 2957, 1728, 1624 cm$^{-1}$; mp 129°–131° C.; HRMS calc'd for C$_{13}$H$_{14}$BrNO$_6$ 359.0005, found 359.0009.

EXAMPLE 43

Vinyl Pyridone (46). To 1.19 g (3.29 mmol) 45 in 30 ml acetonitrile in a pressure tube was added 160 mg (0.53 mmol) tri-o-tolylphoshine, 2.5 ml triethylamine and 59 mg (0.26 mmol) palladium (II) acetate. The reaction vessel was sealed, pressurized with 75 psi ethylene and heated to 125° C. for 3 h. The black solution was allowed to cool to ambient temperature and concentrated in vacuo to a black tar. Radial chromatography (2.5% methanol/dichloromethane; 4 mm silica gel) provided 648 mg (64%) 45 as a tan solid. $^1$H NMR (CDCl$_3$) δ, 6.61 (dd, J=11.7; 17.6 Hz, 1H), 5.85 (d, J=17.6 Hz, 1H), 5.64 (d, J=11.6 Hz, 1H), 5.39–5.37 (m, 1H), 4.31–4.18 (m, 2H), 4.02 (d, J=17.0 Hz, 1H), 3.89 (br s, 1H), 3.85 (d, J=16.9 Hz, 1H), 3.85 (s, 3H), 3.71 (s, 3H), 2.35–2.15 (m, 2H); $^{13}$C NMR (CDCl$_3$) δ, 170.85, 167.13, 159.64, 154.34, 141.08, 129.79, 128.97, 122.69, 107.46, 74.31, 52.30, 52.08, 48.08, 37.38, 28.80; IR (film), 3464, 2951, 1738, 1643 cm$^{-1}$; mp 12520 –127° C.; HRMS calc'd for C$_{15}$H$_{17}$NO$_6$ 307.1056, found 307.1068.

EXAMPLE 44

Methylated Pyridone (47). To 1.50 g (4.89 mmol) 46 in 75 ml THF under nitrogen at –78° C. was added 10.26 ml (10.26 mmol) LiHMDS over 10 min. After 1.25 h, 0.33 ml (5.37 mmol) iodomethane (passed through basic alumina plug prior to use) was added and the reaction mixture was allowed to warm to ambient temperature over 15 h. The reaction was quenched with 25 ml 1M HCl and extracted with ethyl acetate (4×50 ml). The combined organic layer was dried over MgSO$_4$ and concentrated in vacuo to a viscous red liquid. Column chromatography (20% acetone/chloroform) provided 1.40 g (90%) of an inseparable diastereomeric mixture of 47 as an orange foam. $^1$H NMR (CDCl$_3$) δ, 6.53 (dd, J=11.7; 17.6 Hz, 1H), 5.92 (dd, J=1.9; 17.7 Hz, 1H), 5.65 (dd, J=1.9; 11.7 Hz, 1H), 5.30 (m, 1H), 4.31–4.04 (m, 3H), 3.77 (s, 3H), 3.63 (s, 3H), 2.35–2.28 (m, 3H), 1.52 (d, J=7.1 Hz, 3H); $^{13}$C NMR (CDCl$_3$)δ, 173.01, 167.55, 159.68, 154.00, 147.55, 129.33, 127.63, 123.06, 106.84, 74.31, 51.91, 51.84, 48.08, 41.92, 28.87, 16.89; IR (film), 3400, 2990, 2951, 1731, 1634 cm$^{-1}$.

EXAMPLe 45

Tricyclic Pyridone (48).

Through a solution of 1.02 g (3.18 mmol) 47 in 90 ml dichloromethane at –78° C. was passed a stream of ozone until a blue color persisted. The solution was purged with oxygen followed by nitrogen for 15 min, 2.31 ml (31.8 mmol) dimethyl sulfide was added and the reaction mixture was allowed to warm to ambient temperature over 15 h. The yellow solution was concentrated in vacuo and the residue dissolved in 70 ml THF. The yellow solution was cooled to –78° C. and lithium tri-t-butoxyaluminum hydride was added dropwise. After 7 h, 50 ml 1M HCl was added, the cooling bath was removed and the aqueous solution was extracted with dichloromethane (3×50 ml). The combined organic layer was dried over MgSO$_4$ and concentrated in vacuo to a yellow viscous oil which was subjected to radial chromatography (20 to 25% acetone/chloroform; 4 mm silical gel) providing 605 mg (65%) of an inseparable diastereomeric mixture of 48 as a white foam. Analytical data is the same as that described above.

EXAMPLE 46

Ketone (49).

To 1.08 g (3.69 mmol) 48 in 30 ml dichloromethane under nitrogen was added 3.12 g (7.37 mmol) Dess-Martin periodinane. After 1 h the reaction was quenched by the addition of 50 ml NaHCO$_{3(sat)}$ and 50 ml 10% Na$_2$S$_2$O$_3$. The aqueous mixture was extracted with chloroform (4×50 ml) and the combined organic layer was dried over MgSO$_4$ and concentrated in vacuo to a viscous red oil. Column chromatography (20% acetone/chloroform) provided 953 mg (89%) 49 as a pale yellow foam. $^1$H NMR (CDCl$_3$) δ, 5.59 (d, J=17.0 Hz, 1H), 5.24 (d, J=17.0 Hz, 1H), 4.31 (app t, J=6.8 Hz, 2H), 3.94 (s, 3H), 3.75 (q, J=7.5 Hz, 1H), 2.98–2.95 (m, 2H), 1.50 (d, J=7.5 Hz, 3H); $^{13}$C NMR (CDCl$_3$) δ, 194.34, 170.59, 163.91, 157.16, 145.36, 137.73, 125.64, 109.88, 65.14, 53.31, 42.16, 37.15, 33.61, 17.56; IR (film), 2954, 1746, 1659, 1614 cm$^{-1}$; mp 188°–190° C.; HRMS calc'd for C$_{14}$H$_{13}$NO$_6$ 291.0743, found 291.0750.

EXAMPLE 47

14-Carbomethoxy-18-nor-20-des-oxycamptothecin (52).

To 64.3 mg (0.22 mmol) 49 in 10 ml toluene under nitrogen was added 69.6 mg (0.33 mmol) imine 50 and approximately 2 mg p-toluenesufonic acid. The solution was heated to reflux with azeotropic removal of water for 5 h, cooled to ambient temperature and concentrated in vacuo. Column chromatography (15% acetone/chloroform) provided 57.6 mg (69%) of 52 as a red solid. $^1$H NMR (CDCl$_3$) δ, 8.36 (s, 1H), 8.09 (d, J=8.4 Hz, 1H), 7.88 (d, J=7.9 Hz, 1H), 7.81–7.77 (m, 1H), 7.66–7.62 (m, 1H), 5.62 (d, J=16.3 Hz, 1H), 5.28 (d, J=16.3 Hz, 1H), 5.24 (app s, 2H), 4.11 (s, 3H), 3.85 (q, J=7.6 Hz, 1H), 1.60 (d, J=7.6 Hz, 3H); $^{13}$C NMR (CDCl$_3$) δ, 171.36, 165.50, 157.12, 151.19, 148.67, 145.90, 144.27, 130.86, 130.51, 130.19, 128.41, 128.39, 127.93, 127.88, 119.81, 107.98, 65.22, 52.86, 50.08, 37.59, 17.56; IR (film), 3001, 2919, 1731, 1660, 1619 cm$^{-1}$; mp 277°–279° C.; HRMS calc'd for C$_{21}$H$_{16}$N$_2$O$_5$ 376.1059, found 376.1071.

EXAMPLE 48

14-Carbomethoxy-7-Ethyl-10-methoxy-18-nor-20-des-oxy-camptothecin (53).

To 950 mg (3.26 mmol) 49 in 75 ml toluene under nitrogen was added 876 mg (4.89 mmol) amino-ketone 51 and approximately 10 mg p-toluenesufonic acid. The solution was heated to reflux with azeotropic removal of water for 15 h, cooled to ambient temperature and concentrated in vacuo. Column chromatography (10 to 15% acetone/chloroform) provided 992 mg (70%) of 53 as a red solid. $^1$H NMR (CDCl$_3$) δ, 7.99 (d, J=9.2 Hz, 1H), 7.42 (dd, J=2.6; 9.2 Hz, 1H), 7.26 (d, J=2.6 Hz, 1H), 5.64 (d, J=16.2 Hz, 1H), 5.28 (d, J=16.1 Hz, 1H), 5.19 (app s, 2H), 4.09 (s, 3H), 3.98 (s, 3H), 3.85 (q, J=7.5 Hz, 1H), 3.11 (q, J=7.7 Hz, 2H), 1.60 (d, J=7.6 Hz, 3H), 1.36 (t, J=7.6 Hz, 3H); $^{13}$C NMR (CDCl$_3$) δ, 171.52, 165.67, 159.18, 157.28, 148.34, 146.07, 145.43, 145.37, 143.33, 132.59, 128.06, 127.22, 122.57, 118.89, 107.28, 101.27, 65.24, 55.62, 52.75, 49.49, 37.67, 23.04, 17.54, 13.48; IR (film), 2928, 1726, 1660, 1620, 1226 cm$^{-1}$; mp 284°–285° C.; HRMS calc'd for C$_{24}$H$_{22}$N$_2$O$_6$ 434.1478, found 434.1465.

EXAMPLE 49

18-nor-20-desoxycamptothecin (54).

A solution of 57 mg (0.15 mmol) 52 in 3 ml 48% hydrobromic acid was heated in a sealed tube to 130° C. for 24 h, cooled to ambient temperature and concentrated in vacuo. The crude product was used directly in the next step without any further purification. An analytical sample was prepared via column chromatography (25% acetone/chloroform). $^1$H NMR (CDCl$_3$) δ, 8.34 (s, 1H), 8.04 (d, J=8.5 Hz, 1H), 7.83 (d, J=8.3 Hz, 1H), 7.72–7.68 (m, 1H), 7.56–7.52 (m, 1H), 7.28 (s, 1H), 5.42 (d, J=15.5 Hz, 1H), 5.21 (dd, J=1.7; 15.4 Hz, 1H), 5.16 (app s, 2H), 3.60 (q, J=7.1 Hz, 1H), 1.57 (d, J=7.2 Hz, 3H); $^{13}$C NMR (CDCl$_3$) δ, 172.42, 157.88, 151.96, 149.02, 148.52, 146.29, 131.65, 130.84, 129.04, 128.61, 128.21, 128.12, 120.63, 99.06, 64.83, 50.09, 38.91, 14.03; IR (film), 2919, 1724, 1652, 1599; mp 269°–271 ° C.; HRMS calc'd for C$_{19}$H$_{14}$N$_2$O$_3$ 318.1004, found 318,1004.

EXAMPLE 50

7-Ethyl-10-hydroxy-18-nor-20-desoxycamptothecin (56).

A solution of 243 mg (0.56 mmol) of 53 in 18 ml 48% hydrobromic acid was heated in a sealed tube to 130° C. for 14 h, cooled to ambient temperature and concentrated in vacuo. The residue was dissolved in 4:1 chloroform/methanol and washed with NaHCO$_{3(sat)}$. The aqueous was extracted with three additional portions of 4:1 chloroform/methanol, dried over MgSO$_4$, and concentrated in vacuo to 109 mg (54%) 56 which was used without any further purification. $^1$H NMR (CDCl$_3$) δ, 7.90 (d, J=9.0 Hz, 1H), 7.29 (dd, J=1.8; 9.2 Hz, 1H), 7.26 (d, J=2.3 Hz, 1H), 7.19 (s, 1H), 5.43 (d, J=15.4 Hz, 1H), 5.20 (d, J=15.4 Hz, 1H), 5.08 (app s, 2H), 3.58 (q, J=6.8 Hz, 1H), 2.98 (1, J=7.7 Hz, 2H), 1.56 (d, J=7.2 Hz, 3H), 1.24 (t, J=7.7 Hz, 3H); IR (film), 3213, 2919, 1733, 1652 cm$^{-1}$.

EXAMPLE 51

18-nor-20-phenyselenylcamptothecin (55).

To crude 54 (prepared above) in 5 ml degassed pyridine under nitrogen was added 72 mg (0.31 mmol) phenylselenyl bromide. After 24 h the reaction mixture was concentrated in vacuo and the residue was subjected to column chromatography (5% acetone/chloroform) providing 26 mg (36% over two steps) of 55 as a pale yellow solid. $^1$H NMR (CDCl$_3$) δ, 8.39 (s, 1H), 8.22 (d, J=8.5 Hz, 1H), 7.93 (d, J=8.1 Hz, 1H), 7.83 (dt, J=1.3; 8.4 Hz, 1H), 7.67 (appt, J=7.1 Hz, 1H), 7.58–7.56 (m, 2H), 7.44–7.41 (m, 2H), 7.31 (app t, J=7.6 Hz, 2H) 5.48, d, J=16.5 Hz, 1H), 5.32 (d, J=19.0 Hz, 1H), 5.25 (d, J=19.1 Hz, 1H), 5.00 (d, J=16.5 Hz, 1H), 2.08 (s, 3H); $^{13}$C NMR (CDCl$_3$) δ169.23, 157.44, 152.45, 148.94, 147.22, 146.01, 137.98, 131.16, 130.70, 130.55, 129.68, 129.27, 128.52, 128.19, 128.04, 126.40, 121.88, 97.66, 65.59, 49.93, 44.09, 22.42; IR (film), 2918, 1728, 1656, 1603, 1232; mp 271°–273° C.

EXAMPLE 52

7-Ethyl-10-hydroxy-18-nor-20-phenylselenylcamptothecin (57).

To 107 mg (0.30 mmol) crude 56 (prepared above) in 10 ml degassed pyridine under nitrogen was added 140 mg (0.59 mmol) of phenylselenyl bromide. After 24 h the reaction mixture was concentrated in vacuo and subjected to column chromatography (20% acetone/chloroform) providing 93 mg (61%) 57 as a yellow solid. $^1$H NMR (CDCl$_3$) δ, 7.91 (d, J=9.1 Hz, 1H), 7.43–7.41 (m, 2H), 7.35 (s, 1H), 7.32–7.26 (m, 3H), 7.20–7.16 (m, 2H), 5.31 (d, J=16.2 Hz, 1H), 5.11 (d, J=18.8 Hz, 1H), 5.05 (d, J=18.7 Hz 1H), 4.85 (d, J=16.3 Hz 1H), 2.98 (q, J=7.6 Hz, 2H), 1.93 (s, 3H), 1.25 (t, J=7.6 Hz, 3H); $^{13}$C NMR (CDCl$_3$) δ, 169.56, 157.26, 156.62, 148.77, 147.54, 146.94, 144.46, 143.72, 137.96, 131.56, 131.49, 130.53, 129.25, 129.14, 128.69, 126.89, 126.33, 122.63, 120.66, 105.17, 97.26, 65.51, 44.12, 23.07, 22.22, 13.50; IR (film), 3167, 2972, 1731, 1650, 1590, 1235 cm$^{-1}$; mp 176°–179° C.; HRMS calc'd for C$_{27}$H$_{23}$N$_2$O$_4$Se (M+1) 519.0823, found 519.0815.

EXAMPLE 53

7-Ethyl-10-hydroxy-18-nor-anhydrocamptothecin (33).

To 94 mg (0.18 mmol) 57 in 19 ml dichloromethane at 0° C. was added 0.54 ml (0.54 mmol) hydrogen peroxide (1.0M in methanol). After 3 h the cooling bath was removed, the reaction mixture was allowed to warm to ambient temperature over 30 min and concentrated in vacuo. The residue was dissolved in 150 ml 4:1 chloroform/methanol and 500 mg of silica gel was added. The mixture was concentrated in vacuo and applied to a silica gel column as a slurry in chloroform. Elution with 2 to 6% methanol/chloroform provided 26 mg (40%) of 33 as a yellow solid. $^1$H NMR (CDCl$_3$) δ, 7.90 (d, J=9.0 Hz, 1H), 7.42 (s, 1H), 7.29 (dd, J=2.6; 9.0 Hz, 1H), 7.26 (d, J=2.5 Hz, 1H), 6.73 (s, 1H), 6.45 (s, 1H), 5.36 (s, 5.09 (s, 2H), 2.98 (q, J=7.6 Hz, 2H), 1.24 (t, J=7.6 Hz, 3H); IR (film), 3583, 2924, 1731, 1716, 1654, 1583 cm$^{-1}$; mp 176° C. (dec.).

EXAMPLE 54

18-nor-anhydrocamptothecin (32).

To 33 mg (0.08 mmol) 55 in 2 ml dichloromethane at 0° C. was added 0.10 ml (0.10 mmol) hydrogen peroxide (1.0M in methanol). After 4 h at 0° C. the reaction mixture was concentrated in vacuo. The residue was subjected to column chromatography (2% methanol/chloroform) providing 15 mg (57%) 32 as a pale yellow solid. $^1$H NMR (CDCl$_3$) δ, 8.39 (s, 1H), 8.16 (d, J=8.6 Hz, 1H), 7.91 (d, J=8.2 Hz, 1H), 7.82–7.78 (m, 1H), 7.65–7.63 (m, 1H), 7.57 (s, 1H), 6.84 (s, 1H), 6.54 (s, 1H), 5.46 (s, 2H), 5.26 (s, 2H); IR (film), 2924, 1732, 1698; mp 261°–263° C.; HRMS calc'd for C$_{19}$H$_{12}$N$_2$O$_3$ 316.0848, found 316.0845.

Biological Results

Anti-tumor Activity of
18-Nor-20-dehydro-7-ethyl-10-hydroxycamptothecin
Against solid Tumors in BD$_2$F$_1$ Mice The control lane (Table A) indicates separate inoculation of nine mice with B-16 melanoma and sarcoma 180. When no drug was administered, the mice gained 0.1 gm of body weight. Upon treatment with camptothecin at a dosage level of 4 mg/kg, the two mice inoculated with B-16 melanoma experienced an average weight loss of 1.8 gm and the tumor shrunk in volume by 40%. The two mice inoculated with sarcoma 180 experienced an average weight loss of 0.9 gm while the tumor shrunk in volume by 36%. Administration of 10 mg/kg (2.5 time the dosage of authentic camptothecin) of 18-nor-20-dehydro-7-ethyl-10-hydroxycamptothecin to the mice inoculated with B-16 melanoma resulted in decreased body weight of 1.4 gm and decreased tumor volume by 14% while a dosage of 30 mg/kg (7.5 times the dosage of authentic camptothecin) resulted in decreased body weight by 1.9 gm and decreased tumor volume by 81%. In the sarcoma 180 tumor cell line, administration of 10 mg/kg resulted in a decrease in body weight of 0.6 gm and a reduction in tumor volume by 32% while injection of 30 mg/kg resulted in a decrease in body weight of 3.0 gm and decreased tumor volume by 91%. The latter results are skewed, however, since one of the two subjects died after day 4 of treatment. Therefore, the optimal dosage level apparently is between 10 and 30 mg/kg. The activity of the synthetic 18-nor-20-dehydro-7-ethyl-10-hydroxycamptothecin compares favorably with that of authentic camptothecin.

TABLE A

Anti-tumor activity of Camptothecin and
20-CH$_2$-7-ethyl-10-OH-Camptothecin
Against Solid Tumors in BD$_2$F$_1$ Mice[a]

| Compound | Dose (mg/kg) | B-16 Melanoma | | Sarcoma 180 | |
| --- | --- | --- | --- | --- | --- |
| | | AWC (gm) | Ave Tumor Volume (T/C) | AWC (gm) | Ave Tumor Volume (T/C) |
| Control | 0 | +0.1 | 1.00 | +0.1 | 1.00 |
| CPT | 4 | −1.8 | 0.595 | −0.9 | 0.634 |
| 20-CH$_2$-7-Et-10-OH-CPT | 10 | −1.4 | 0.858 | −0.6 | 0.683 |
| | 30 | −1.9 | 0.189 | −3.0[c] | 0.098 |

[a]Tumor (2.5 × 10$^6$ cells) was inoculated s.c.; treatment started day 4. QD × 5, i.p.; Control had nine mice, and each dose had two mice; Tumor size was evaluated on day 7 after the beginning of treatment.
[b]AWC: Average weight change.
[c]One of two mice died on day 4 after treatment.

Evaluation of Anti-tumor Activity in Vivo

Anti-tumor activity of the newly synthesized compounds and the established drugs (as positive controls) against solid tumors (B-16 melanoma and sarcoma 180) was tested in BD$_2$F$_1$ mice. Tumor (about 2.5×10$^6$ cells) was inoculated subcutaneously (s.c.). Treatment with the drug started on day 4 after inoculation. The drug was injected intraperitoneously (i.p) daily (QD) for five days. Control mice received the same volume (50 μl) of the solvent vehicle (Dinso) as the drug-treated animals. Tumor size was evaluated every few days using a caliper for both the control and the treated group. Average body weight changes were recorded daily. Any lethality due to high dose drug toxicity or due to tumor progression was also recorded.

TABLE B

SOLID TUMOR EVALUATION

Tumor: B16 Melanoma
Inoculation: 2 × 10$^6$ cells. S.C.

Drug A = Camptothecin
Drug B = 20-CH$_2$-7-ethyl-10-OH Camptothecin
Schedule: QD × 5. I.P. started day 4
Diluent = DMSO

| EXP. GROUP | COMPOUND | DOSAGE (MG/KG) | DAY OF EVALUATION | AWC[A] (GM) | DEATHS (D/L) | AVERAGE TUMOR VOLUME (CM$^3$) | PERCENT OF CONTROL |
| --- | --- | --- | --- | --- | --- | --- | --- |
| 1 | CONTROL | | 7 | +0.1 | 0/4 | 0.190 | — |
| 2 | A | 4 | 7 | −1.8 | 0/2 | 0.113 | 59.5 |
| 3 | B | 10 | 7 | −1.4 | 0/2 | 0.163 | 85.8 |
| 4 | B | 30 | 7 | −1.9 | 0/2 | 0.036 | 18.9 |
| 1 | CONTROL | | 14 | +2.9 | 0/4 | 3.190 | — |
| 2 | A | 4 | 14 | +2.4 | 0/2 | 3.500 | 109.8 |

TABLE B-continued

SOLID TUMOR EVALUATION

| 3 | B | 10 | 14 | +2.7 | 0/2 | 2.320 | 72.7 |
| 4 | B | 30 | 14 | +2.7 | 0/2 | 2.925 | 91.7 |

[a]AWC = Average Weight Change

TABLE C

SOLID TUMOR EVALUATION

Tumor: Sarcoma 180  
Inoculation: $3 \times 10^6$ cells. S.C.  
Drug A = Camptothecin  
Drug B = 20-$CH_2$-7-ethyl-10-OH Camptothecin  
Schedule: QD × 5. I.P. started day 4  
Diluent = DMSO

| EXP. GROUP | COMPOUND | DOSAGE (MG/KG) | DAY OF EVALUATION | AWC[A] (GM) | DEATHS (D/L) | AVERAGE TUMOR VOLUME ($CM^3$) | PERCENT OF CONTROL |
|---|---|---|---|---|---|---|---|
| 1 | CONTROL |   | 7  | 0    | 0/5     | 0.164 | —    |
| 2 | A       | 4 | 7  | −0.9 | 0/2     | 0.104 | 63.4 |
| 3 | B       | 10| 7  | −0.6 | 0/2     | 0.112 | 68.3 |
| 4 | B       | 30| 7  | −3.0 | 1/2[b]  | 0.016 | 9.8  |
| 1 | CONTROL |   | 14 | +1.2 | 0/5     | 0.203 | —    |
| 2 | A       | 4 | 14 | +0.8 | 0/2     | 0.080 | 39.4 |
| 3 | B       | 10| 14 | +1.5 | 0/2     | 0.090 | 44.3 |
| 4 | B       | 30| 14 | −0.7 | 0/1     | 0.024 | 11.8 |

[a]AWC = Average Weight Change  
[b]Death Occurred on Day 4 After Treatment

Discussion

The camptothecin family of cytotoxic drugs has been evaluated for use in cancer chemotherapy (Wall, M. E. and Wani, M. C. In *Economic and Medicinal Plant Research*, Wagner, H. and Farnsworth, N. R., Eds., Academic Press: New York, Vol. 5, pp 111–127 (1991); Wall, M. E., et al. *J. Med. Chem.*, 36, 2689 (1993); Wall, M. E. and Wall, M. C. In *Human Medicinal Agents from Plants*, American Chemical Society, Vol. 534, pp149–169 (1993)). Chemical investigations have provided new synthetic routes to the series (Cai, J.-C. and Hutchinson, C. R. In *Chem. Heterocycl. Cmpd.*, 25, 753 (1983); Cai, J.-C and Hutchinson, C. R. In *The Alkaloids: Chemistry and Pharmacology*, A. Brossi, Ed., Academic Press: New York, vol. 21, pp101 (1983); Hutchinson, C. R. *Tetrahedron*, 37, 1097 (1981); Schultz, A. G. *Chem. Rev.*, 385 (1973)).

While several concise syntheses of the natural product are known (Shen, W.; et al., *J. Org. Chem.*, 58, 611 (1993); Comins, D. L., et al., *J. Am. Chem. Soc.*, 114, 10971 (1992); Curran, D. P. and Liu, H. *J. Am. Chem. Soc.*, 114, 5863 (1992); Curran, D. P. *J. Chin. Chem. Soc.*, 40, 1 (1993)), it remains uncertain whether total synthesis can compete with isolation from *Camptotheca accuminata* (Wall, M. E., et al., *J. Am. Chem. Soc.*, 88, 3888 (1966)) as a route to camptothecin itself. However, the focus has shifted from the natural product to less toxic and more soluble analogs (Wall, M. E. and Wani, M. C. In Economic and Medicinal Plant Research Wagner, H. and Farnsworth, N. R., Eds., Academic Press: New York, Vol. 5, pp 111–127 (1991); Wall, M. E., et al., *J. Med. Chem.*, 36, 2689 (1993); Wall, M. E. and Wall, M. C. In Human Medicinal Agents from Plants American Chemical Society, Vol. 534, pp149–169 (1993); Kingsbury, W. D., et al., *J. Med. Chem.*, 34, 98 (1991); Mattern, M. R., et al., *Cancer Res.*, 51, 5813 (1991); Sawada, S., et al., *Chem. Pharm. Bull.*, 39, 1446 (1991); Kharbanda, S., et al., *Cancer Res.*, 51, 6636 (1991)).

At the biological level, interest in this series has been heightened by the identification of a likely mode of action for camptothecin-like drugs. Thus, the parent camptothecin inhibits the action of topoisomerase I on DNA unwinding (Fang, S.-D. et al *J. Org. Chem.*, 58, 5025 (1993); Berry, D. E., et al., *J. Org. Chem.*, 57, 420 (1992)). Camptothecin binds neither to the enzyme nor to its DNA target in isolation. Its involvement is directed toward the enzyme-DNA complex (Hsiang, Y. H., et al., *J. Biol. Chem*, 260, 14873 (1985); Hertzberg, R. P., et al., *Biochemistry*, 28, 4629 (1989); Liu, L. F. *Annu. Rev. Biochem.*, 58, 351 (1989); Thomsen, B., et al., *EMBO J.*, 6, 1817 (1987)). Since the effect is reversible with heat, high salt concentrations and high dilution (Hsiang, Y. H., et al., *J. Biol. Chem.*, 260, 14873 (1985)), the inhibitory effect is not a consequence of a stable covalent bond to either of the individual macromolecular targets or to the complex.

While some substitutions in the quinoline sector of the camptothecin structure have been tolerated with significant maintenance of inhibitory function (Burke, T. G. and Mi, Z. *J. Med. Chem.*, 36, 2580 (1993); Wani, M. C., et al., *J. Med. Chem.*, 30, 1774 (1987)), the requirements in the α-hydroxyl-δ-lactone sector have been stricter (Nicholas, A. W., et al., *J. Med. Chem.*, 33, 972 (1990); Ejima, A., et al., *Chem. Pharm. Bull.*, 40, 683 (1992); Ejima, A., et al., *Chem. Pharm. Bull.*, 37, 2253 (1989); Yaegashi, T., et al., *Chem. Pharm. Bull.*, 41, 971 (1993)). Herein described are the consequences of modifications of the E-ring area intended to promote the possibility of covalent bonding between the drug and either element of its two-component target (Shu, A. Y. L., et al., *J. Labelled Compd. Radiopharm.*, 28, 1265 (1990); Hertzberg, R. P., et al., *J. Biol. Chem.*, 265, 19287 (1990 )).

In particular, compounds 32 and 33 (FIG. 7) were identified as possibilities in the expectation that the vinylogous α-methylene-β-dicarbonyl system found in each would serve as a powerful alkylating site. The formation of a stable drug-target adduct could provide useful structural leads as to the mode of inhibitory action. No homogenous exo-ethylidene analog (cf. 34 or 35) of the parent camptothecin or its analogs is known. The conversion of 20-des-oxycamptothecin to a mixture of cis and trans 20-ethylidenecamptothecin analogs was effected by treatment of 20-desoxycamptothecin with phenylselenyl bromide in pyridine followed by oxidative elimination (80° C.). However, these compounds could not be separated.

The exo-methylidene targets 32 and 33 are preferred candidates for use. The exocyclic methylene group would provide a more electrophilic alkylation target. Furthermore, problems due to E/Z isomerism are thereby avoided. The possibility of reaching 32 and 33 via degradation of camptothecin seemed to be remote, thus prompting an attempt at total synthesis.

Figure 7:
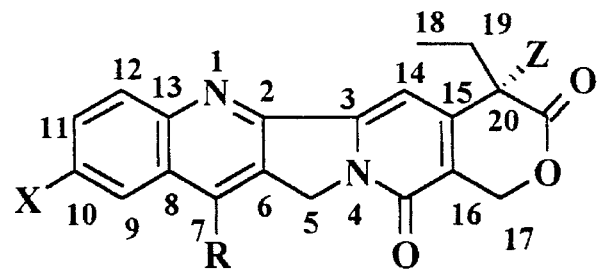
FIG. 7 illustrates camptothecin, 10-hydroxycamptothecin, 20-desoxycamptothecin 36, 10-hydroxy-20-desoxycamptothecin 37, exo-methylene analogues 32–35, and key intermediate 38.
Figure 7:
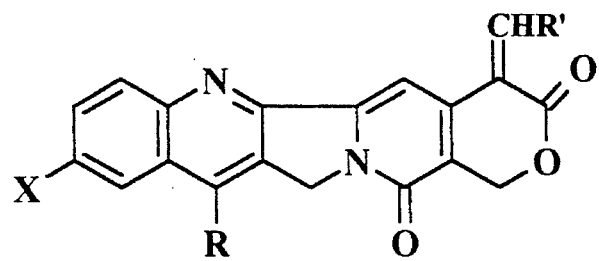
Figure 7:
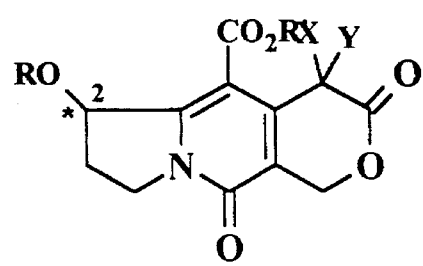

These "nor" compounds could be obtained from the phenylseleno derivatives 55 and 57 which might be available via the 18-nor-20-des-oxy systems 54 and 56 (vide infra). Initially, the synthesis of these late intermediates would be accomplished by modification of a previously described total synthesis (Shen, W., et al., *J. Org. Chem.*, 58, 611 (1993)) which reached 20-des-oxycamptothecin 36 or CPT-11 precursor 37 (FIG. 7). However, the markedly decreased solubility of the 20-methyl compounds relative to the 20-ethyl systems undermined extension of the original route to the 18-nor series. In particular, it became necessary to incorporate the C-2 benzylic oxygen function in advance of reaching a tricyclic intermediate (cf. 38). This is in contrast to the later stage introduction practiced in the disclosed total synthesis of Shen, W., et al., *J. J. Org. Chem.*, 58, 611 (1993). A synthesis of 32 and 33 is disclosed herein.

Figure 8:
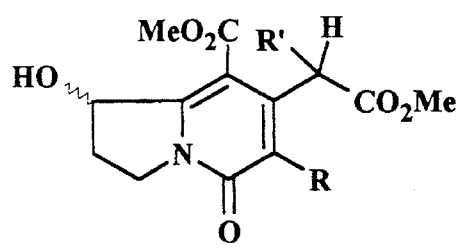
FIG. 8 illustrates intermediates 42–49 useful in preparing exo-methylene camptothecins according to the process of the subject invention.
Figure 8:
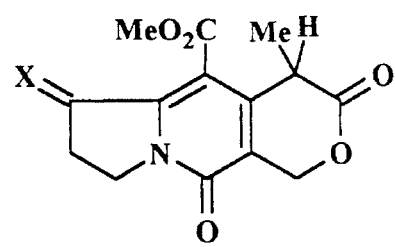

The route starts with the known imino ether 39 (Yamada, Y. and Okada, H. *Agr. Biol. Chem.*, 40, 1437 (1976)) which already bears the required oxygen functionality which will eventually become C-2. Compound 39 was condensed with Meldrum's acid under conditions known to one of ordinary skill in the art (Fasseur, D., et al., *J. Heterocyclic Chem.*, 29, 1285 (1992)) to afford 40 which was converted to 41 upon treatment with sodium methoxide. The vinylogous urethane reacted with 1,3-dicarbomethoxyallene (generated in situ from dimethyl-3-chloroglutaconate (Bryson, T. A. and Dolak, T. M., *Organic Synthesis*, Wiley: New York, Vol. Coll. Vol. VI, pp 505 (1988)), to afford 42 (FIG. 8). Mono C-methylation of the vinylogous malonate moiety afforded 43. This reaction also provided a dimethylated compound which was difficult to remove from the desired 43. (Further complications due to the presence of the C-2 hydroxyl group were observed leading to decreased yields and purification problems in the subsequent "lactomethylation" step.) Lactomethylation of 43 (Danishefsky, S., et al., *J. Am. Chem. Soc.*, 93, 5575 (1971); Volkmann, R., et al., *J. Am. Chem. Soc.*, 93, 5576 (1971)) via condensation with formaldehyde did give 44.

Another desirable capability is to synthesize structures where the formaldehyde lactomethylation reaction fails. Although formation of the camptothecin E ring via lactomethylation with paraformaldehyde in acidic dioxane works quite well when the future 20-position of the seco precursor is mono-alkylated, substrates bearing a free methylene group substitution at the 20-position fail to undergo the desired reaction. This is apparently due to attack of the formaldehyde at C-20 which bears vinylogous malonate character. An alternative route was developed which solved these problems.

Accordingly, compound 42 was treated with N-bromosuccinimide thereby providing an 88% yield of 45 (FIG. 8). The latter underwent vinylation under Heck conditions (Plevyak, J. E. and Heck, R. F. *J. Org. Chem.*, 43, 2454 (1978)) to afford 46. With the additional steric hindrance and solubility apparently imposed by the presence of the ortho-vinyl group, clean mono methylation was achieved via reaction of the lithium enolate of 46 with methyl iodide. Ozonolysis of the resultant 47 was followed by reduction with lithium tri-tert-butoxyaluminum hydride affording 48 which, after oxidation with the Dess-Martin periodinane (Dess, D. B. and Martin, J. C. *J. Am. Chem. Soc.*, 113, 7277 (1991); Ireland, R. E. and Liu, L. *J. Org. Chem.*, 58, 2899 (1993)); for the use of a non-traditional Dess-Martin reagent, see: VanderRoest, J. M. and Grieco, P. A. *J. Am. Chem. Soc.*, 115, 5841 (1993)) provided an 89% yield of 49.

Figure 9:
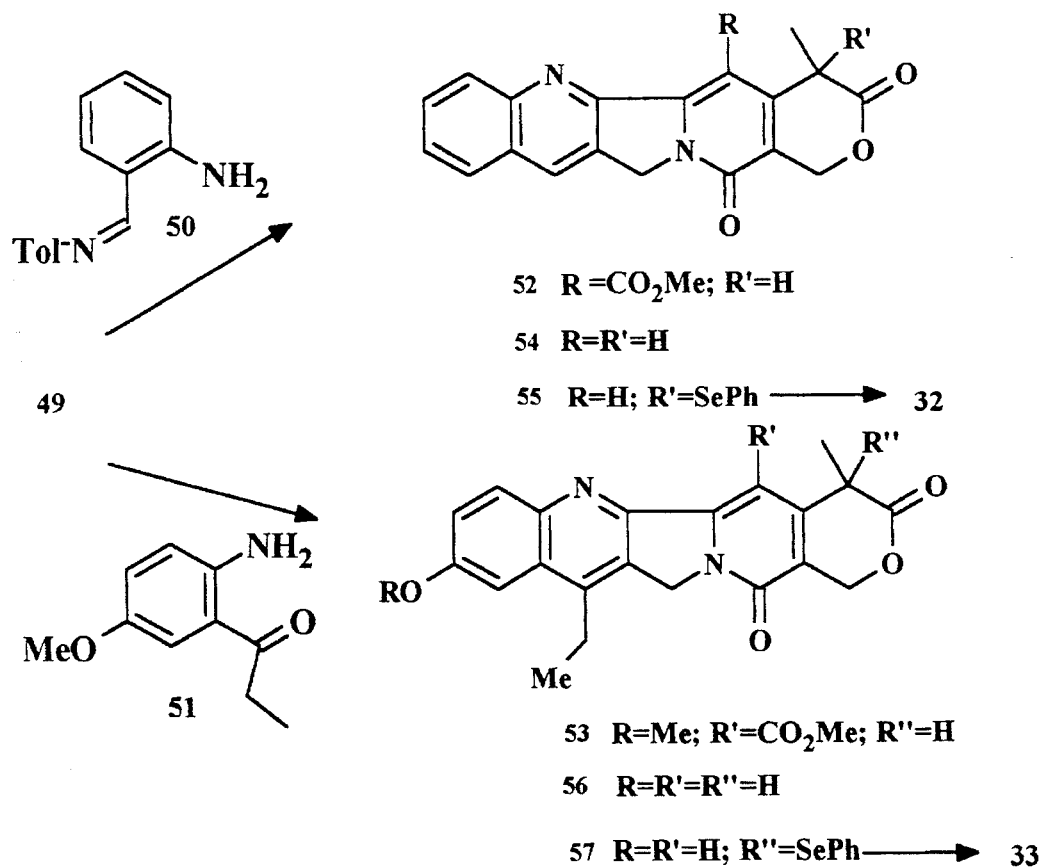
FIG. 9 illustrates condensation steps leading to exomethylene camptothecins according to the process of the subject invention.

Friedlander-like coupling (FIG. 9; Cheng. C.-C. and Yan, S.-J. *Org. React.*, 28, 37 (1982)) of 49 with 50 and with 51 (Shen, W., et al., *J. Org. Chem.*, 58, 611 (1993)) afforded 52 and 53, respectively. The replacement of the usual 20-ethyl group by a 20-methyl function significantly aggravated an already serious solubility problem for the subsequent steps. Thus, HBr-induced decarbalkoxylation (Danishefsky, S. and Etheredge, S. J. *J. Org. Chem.*, 39, 3430 (1974)) of 52 produced an incompletely characterized product assigned as 54. Treatment of this material with phenylselenyl bromide afforded 55, though in only 36% overall yield from 52. Finally, oxidative elimination of the phenylseleno group, through the action of hydrogen peroxide, led to the formation of 32 in 53% yield. In a similar way, decarbalkoxylation of 53 with HBr produced 56 which was isolated in homogenous form (54%). Selenylation as above afforded 57 in 61% yield and subsequent oxidative deselenylation of 57 gave rise to 33 in 40% yield. The yields encountered in the concluding steps reflect the difficulties associated with processing and purifying insoluble materials rather than interfering side reactions.

Figure 10:
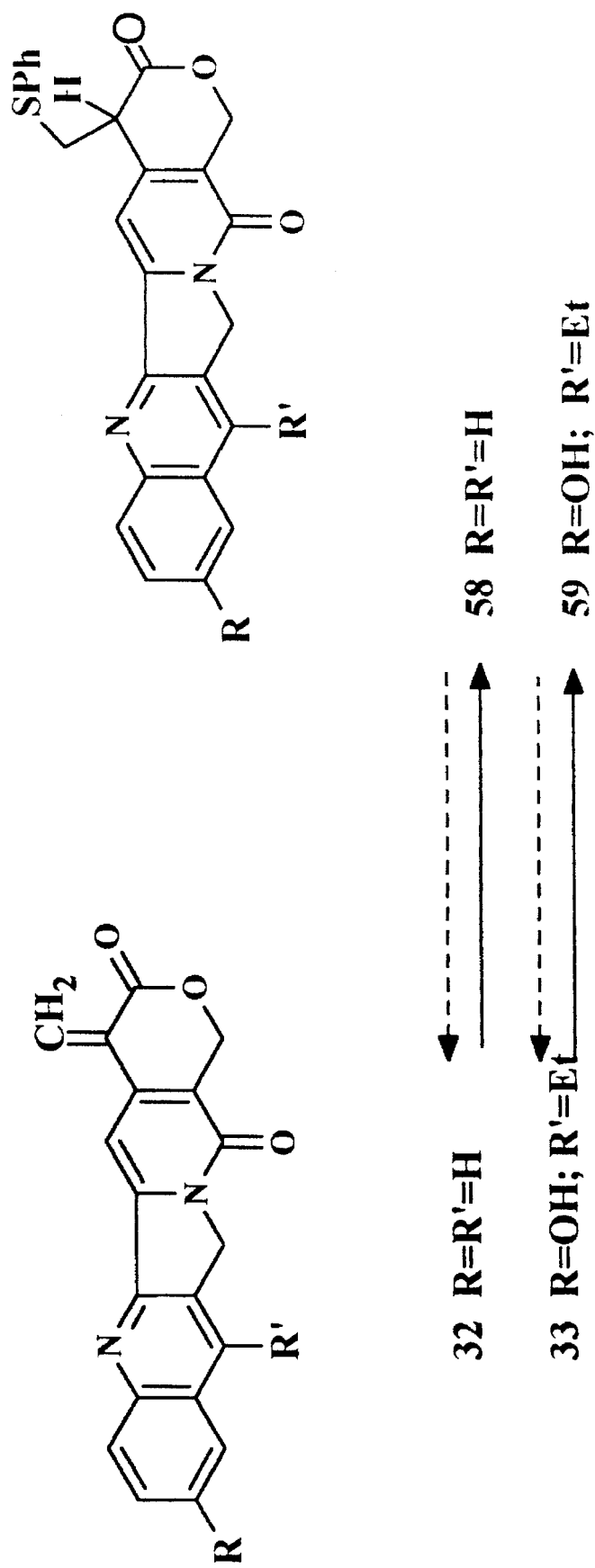
FIG. 10 illustrates the reversible formation of an adduct between thiophenol and exo-methylene camptothecins.
Figure 11:
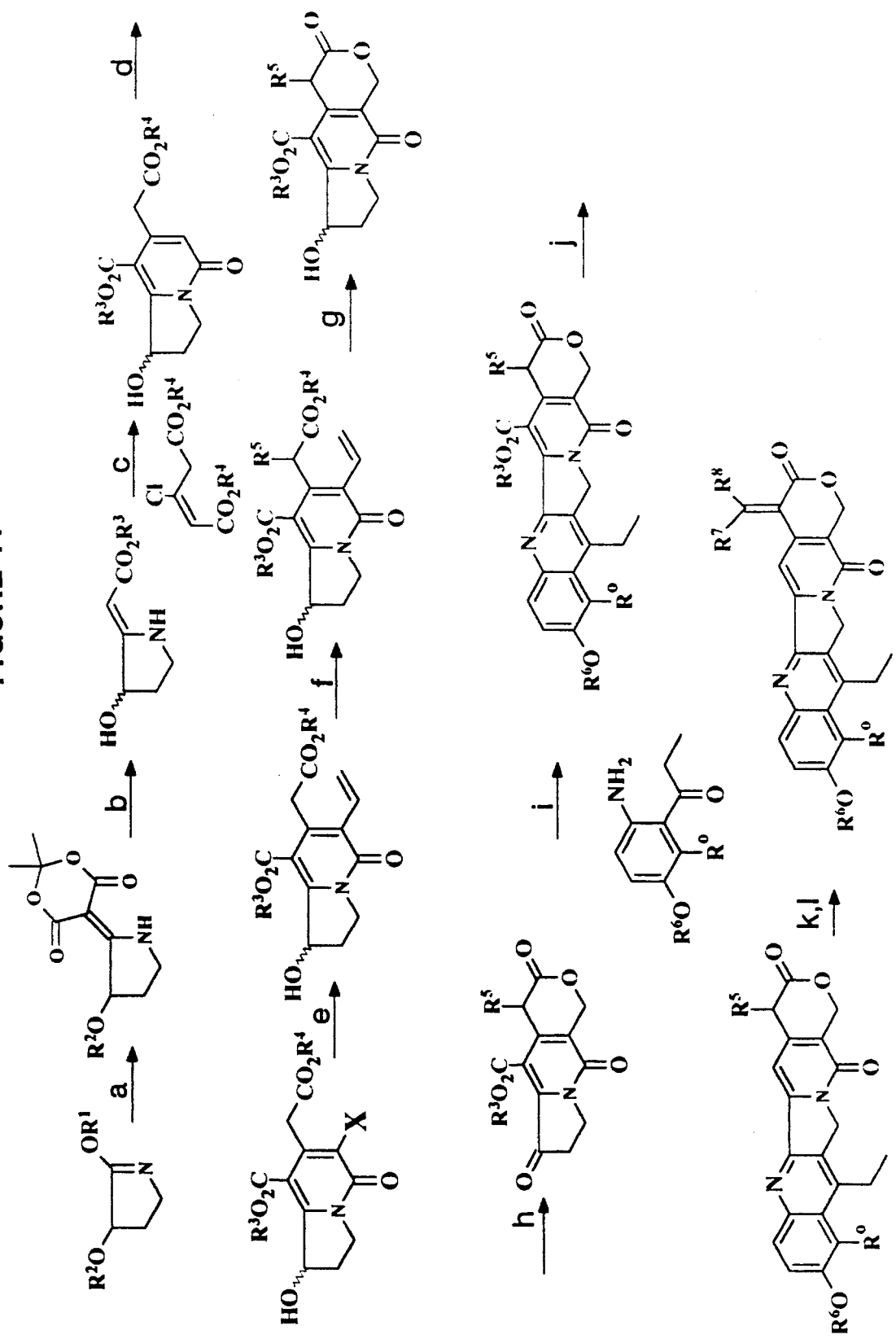
FIG. 11 illustrates the synthesis of exo-methylene camptothecins. $R^1$, $R^2$, $R^3$, $R^4$, $R^5$, $R^6$, $R^7$, $R^8$ and $R^0$ are defined as in the Detailed Description hereinbelow. (a) Meldrum's acid; (b) sodium methoxide; (c) dimethyl 3-chloroglutaconate; (d) (if X=Br) N-bromosuccinimide; (e) Heck vinylation; (f) LiH, $R^5$I; (g) $O_3$, then Li tri-tertbutoxyaluminum hydride; (h) Dess-Martin periodinane; (i) Friedlander conditions; (j) HBr; (k) phenylselenyl bromide; (l) hydrogen peroxide.

Experiments were performed (FIG. 10) to demonstrate that 32 and 33 would indeed function as strong electrophiles. Treatment of each compound with thiophenol in dichloromethane led to consumption of starting material. (For a related example of thiophenol addition to α-methylene-γ-lactones, see: Marshall, J. A., et al., *J. Org. Chem.*, 47, 699 (1982).) NMR analysis of the crude reaction mixture indicated formation of the expected adducts 58 and 59. However, in each case attempted chromatographic purification of these compounds on silica gel and/or aqueous work-up resulted in decomposition of the apparent adduct with re-isolation of small amounts of 32 and 33. These compounds exhibit potent camptothecin-like inhibition of topoisomerase-I activity.

While cytotoxicity was manifested in compound 33, the significantly reduced levels relative to camptothecin are perhaps due to reduced bioavailability. Compound 33 is the camptothecin analog with the most extensively modified E ring still retaining enzyme inhibitory function.

What is claimed is:

1. A compound having the structure:

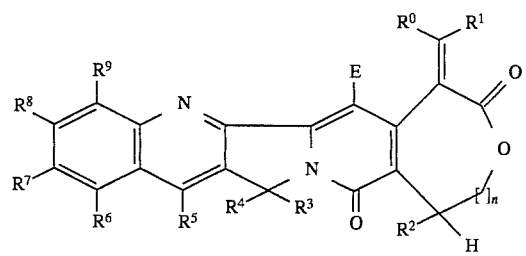

wherein E is H, $CO_2R$, $CONH_2$, CONHR, $CONR_2$, or CN; $R^0$ and $R^1$ are independently the same or different and are H, or a linear or branched alkyl, linear or branched alkylaryl, hydroxyalkyl or aryl group; $R^2$, $R^3$, and $R^4$ are independently the same or different and are H, or a linear or branched alkyl, linear or branched alkylaryl, hydroxyalkyl or aryl group: $R^5$, $R^6$, $R^7$, $R^8$ and $R^9$ are independently the same or different and are H, or a linear or branched alkyl, linear or branched alkylaryl or aryl group, or an alkoxy, aryloxy, hydroxyalkyl, C-glycal, nitro, cyano or aminoalkoxy group, or $CO_2R$, Cl, F, Br, I, $SR^{10}$, $NR^{11}R^{12}$ or $OR^{13}$; R is H, an alkyl, aryl, alkylaryl or hydroxyalkyl group; $R^{10}$, $R^{11}$ and $R^{12}$ are independently the same or different and are H, an alkyl, aryl, alkylaryl or acyl group; $R^{13}$ is glycosyl; and n is 0 or 1.

2. The compound of claim 1, wherein n is 0.
3. The compound of claim 2, wherein $R^7$ is OH.
4. The compound of claim 3, wherein $R^6$ is C-glycal and the compound has the structure:

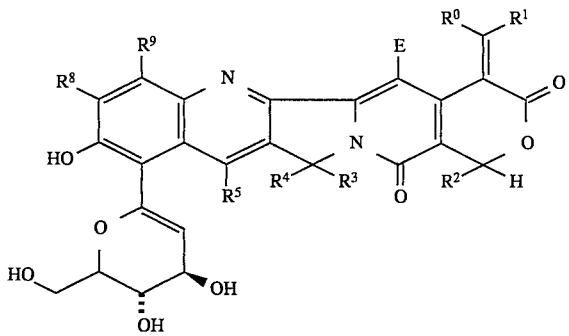

wherein E is H, $CO_2R$, $CONH_2$, CONHR, $CONR_2$, or CN; $R^0$ and $R^1$ are independently the same or different and are H, or a linear or branched alkyl, linear or branched alkylaryl, hydroxyalkyl or aryl group; $R^2$, $R^3$, and $R^4$ are independently the same or different and are H, or a linear or branched alkyl, linear or branched alkylaryl, hydroxyalkyl or aryl group; $R^5$, $R^8$, and $R^9$ are independently the same or different and are H, or a linear or branched alkyl, linear or branched alkylaryl, aryl, alkoxy, aryloxy, hydroxyalkyl, C-glycal, nitro, cyano or aminoalkoxy group, or $CO_2R$, Cl, F, Br, I, $SR^{10}$, $NR^{11}R^{12}$ or $OR^{13}$; R is H, an alkyl aryl alkylaryl or hydroxyalkyl group; $R^{10}$, $R^{11}$ and $R^{12}$ are independently the same or different and are H, an alkyl, aryl, alkylaryl or acyl group; and $R^{13}$ is glycosyl.

5. The compound of claim 4, wherein $R^3$ is ethyl.
6. The compound of claim 5, wherein $R^1$, $R^2$, $R^3$, $R^4$ and E are H.
7. The compound of claim 6, wherein $R^8$ and $R^9$ are H.
8. The compound of claim 1, wherein $R^{13}$ is glycosyl and the compound has the structure:

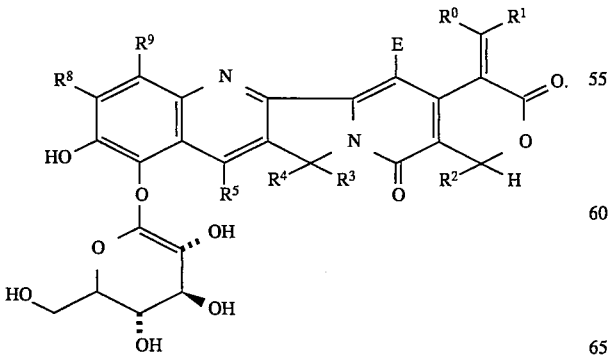

9. The compound of claim 8, wherein $R^5$ is ethyl.

10. The compound of claim 9, wherein $R^1$, $R^2$, $R^3$, $R^4$ and E are H.
11. The compound of claim 10, wherein $R^8$ and $R^9$ are H.
12. A process of synthesizing a compound having the structure:

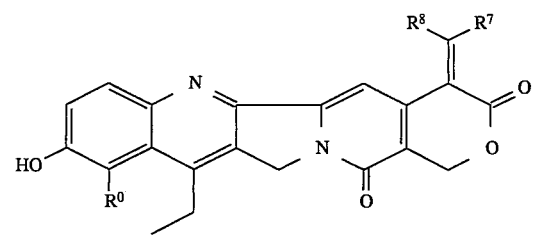

wherein $R^0$ is H, or a linear or branched alkyl, linear or branched arylalkyl, linear or branched alkylaryl or aryl group, or a C-glycal or O-glycosyl group; wherein $R^7$ and $R^8$ are independently the same or different and are H, or a linear or branched alkyl, linear or branched arylalkyl, linear or branched alkylaryl or aryl group, which comprises:

(a) preparing a compound having the structure:

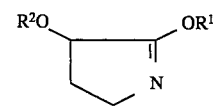

wherein $R^1$ and $R^2$ are independently the same or different and are a linear or branched alkyl, linear or branched arylalkyl, linear or branched alkylaryl, or aryl group;

(b) treating the compound formed in step (a) with Meldrum's acid under suitable conditions to form a compound having the structure:

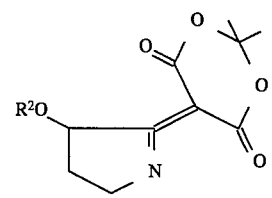

wherein $R^2$ is a linear or branched alkyl, linear or branched arylalkyl, linear or branched alkylaryl or aryl group;

(c) treating the compound formed in step (b) with base under suitable conditions to form a compound having the structure:

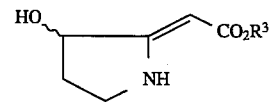

wherein $R^3$ is a linear or branched alkyl, linear or branched arylalkyl, linear or branched alkylaryl or aryl group;

(d) reacting the compound formed in step (c) with a suitable unsaturated carboxylic ester under suitable conditions to form a compound having the structure:

101

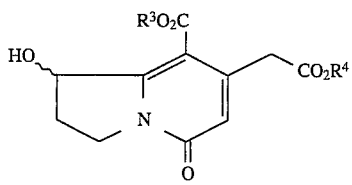

wherein $R^3$, and $R^4$ are independently the same or different and are a linear or branched alkyl, linear or branched arylalkyl, linear or branched alkylaryl or aryl group;

(e) halogenating the compound formed in step (d) under suitable conditions to form a compound having the structure:

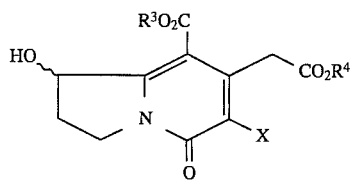

wherein $R^3$, and $R^4$ are independently the same or different and are a linear or branched alkyl, linear or branched arylalkyl, linear or branched alkylaryl or aryl group; and X is F, Cl, Br or I;

(f) treating the compound formed in step (e) under suitable conditions to form a compound having the structure:

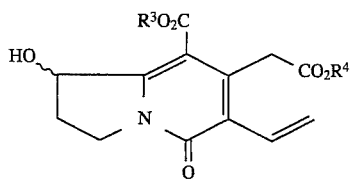

wherein $R^3$, and $R^4$ are independently the same or different and are a linear or branched alkyl, linear or branched arylalkyl, linear or branched alkylaryl or aryl group;

(g) alkylating the compound formed in step (f) with alkylating agent under suitable conditions to form a compound having the structure:

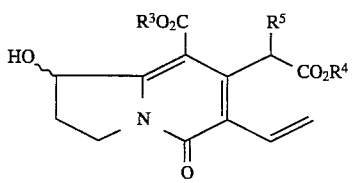

wherein $R^3$ and $R^4$ are independently the same or different and are a linear or branched alkyl, linear or branched arylalkyl, linear or branched alkylaryl or aryl group; and wherein $R^5$ is a linear or branched alkyl or linear or branched arylalkyl;

(h) cleaving oxidatively the compound formed in step (g) under suitable conditions and subsequently reducing under suitable conditions to form a compound having the structure:

102

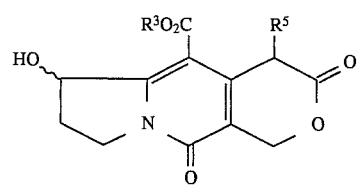

(i) oxidizing the compound formed in step (h) under suitable conditions to form a compound having the structure:

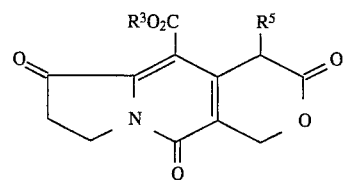

(j) condensing the compound formed in step (i) with a compound having the structure:

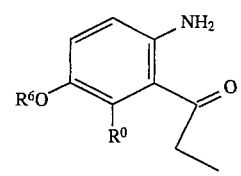

wherein $R^0$ is H, or a linear or branched alkyl, linear or branched aralkyl, linear or branched alkylaryl or aryl, or a C-glycal or O-glycosyl group; wherein $R^6$ is H, or a linear or branched alkyl, linear or branched alkylaryl or aryl, or glycosyl group, under suitable conditions to form a compound having the structure:

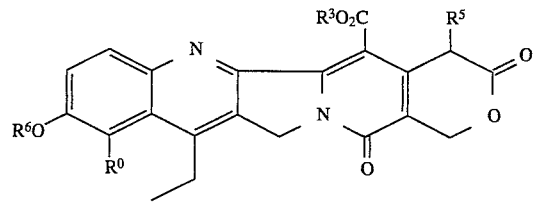

(k) hydrolyzing and decarboxylating the compound formed in step (j) under suitable conditions to form a compound having the structure:

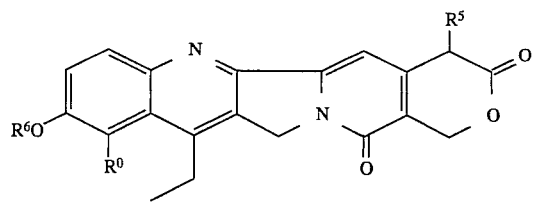

(l) selenylating the compound formed in step (k) under suitable conditions to form a compound having the structure:

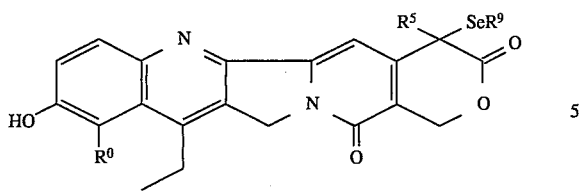

wherein $R^9$ is a linear or branched alkyl, linear or branched arylalkyl, linear or branched alkylaryl, or aryl group; and (m) dehydroselenylating the compound formed in step (l) sunder suitable conditions to form a compound having the structure:

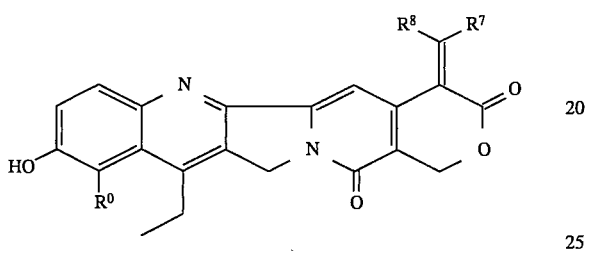

wherein $R^7$ and $R^8$ are independently the same or different and are H, or a linear or branched alkyl, linear or branched arylalkyl, linear or branched alkylaryl or aryl group.

13. The process of claim 12, wherein $R^1$ is $CH_3$ and $R_2$ is Ac.

14. The process of claim 13, wherein $R^3$ is $CH_3$.
15. The process of claim 14, wherein $R^4$ is $CH_3$.
16. The process of claim 15, wherein X is Br.
17. The process of claim 16, wherein $R^5$ is $CH_3$.
18. The process of claim 17, wherein $R^6$ is $CH_3$.
19. The process of claim 18, wherein $R^7$ and $R^8$ are both H.

20. A process for preparing a compound having the structure:

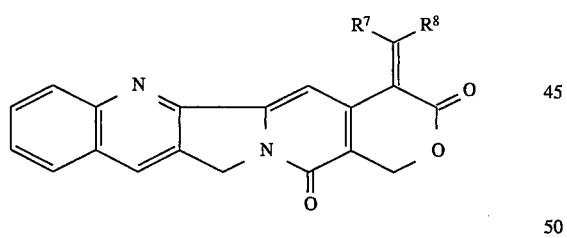

wherein $R^7$ and $R^8$ are independently the same or different and are H, or a linear or branched alkyl, linear or branched arylalkyl, linear or branched alkylaryl or aryl group, which comprises:

(a) preparing in accordance with claim 12 the compound having the structure:

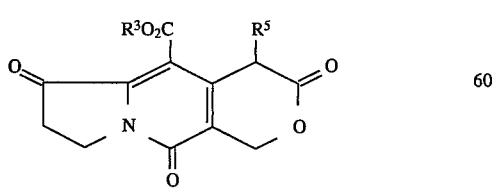

wherein $R^3$ is a linear or branched alkyl, linear or branched arylalkyl, linear or branched alkylaryl, or aryl group; and wherein $R^5$ is a linear or branched alkyl or linear or branched arylalkyl;

(b) condensing the compound formed in step (a) with a compound having the structure:

wherein R is a linear or branched alkyl, linear or branched arylalkyl, linear or branched alkylaryl or aryl group, under suitable conditions to form a compound having the structure:

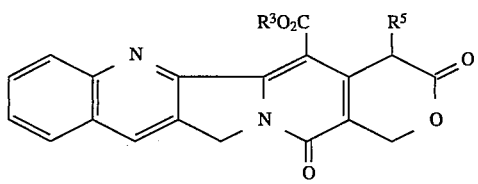

(c) hydrolyzing and decarboxylating the compound formed in step (b) under suitable conditions to form a compound having the structure:

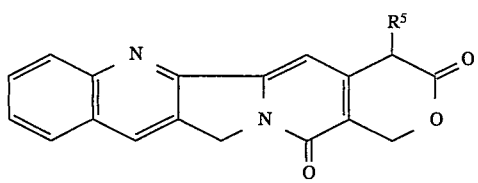

(d) selenylating the compound formed in step (c) under suitable conditions to form a compound having the structure:

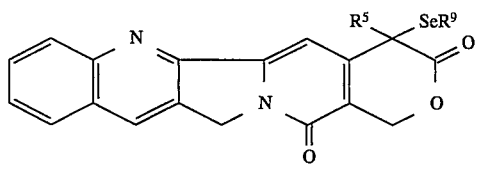

wherein $R^9$ is H, or a linear or branched alkyl, linear or branched arylalkyl, linear or branched alkylaryl or aryl group; and (e) dehydroselenylating the compound formed in step (d) under suitable conditions to form a compound having the structure:

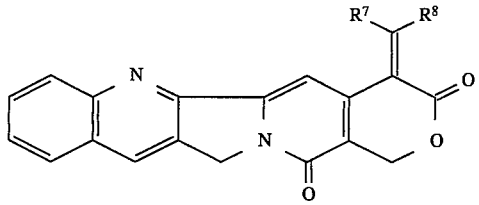

wherein $R^7$ and $R^8$ are independently the same or different and are H, or a linear or branched alkyl, linear or branched arylalkyl, linear or branched alkylaryl or aryl group.

21. The process of claim 20, wherein $R^1$ is $CH_3$ and $R_2$ is Ac.

22. The process of claim 21, wherein $R^3$ is $CH_3$.

23. The process of claim 22, wherein $R^4$ is $CH_3$.

24. The process of claim 23, wherein X is Br.

25. The process of claim 24, wherein $R^5$ is $CH_3$.

26. The process of claim 25, wherein $R^6$ is $CH_3$.

27. The process of claim 28, wherein $R^7$ and $R^8$ are both H.

28. A pharmaceutical composition which comprises the compound of claim 1 in a therapeutically effective amount and a pharmaceutically acceptable carrier.

29. The pharmaceutical composition of claim 28 wherein the carrier is a solid and the composition is a tablet.

30. The pharmaceutical composition of claim 29 wherein the therapeutically effective amount is an amount from about 1 to about 500 mg.

31. The pharmaceutical composition of claim 28 wherein the carrier is a liquid and the composition is a solution.

32. The pharmaceutical composition of claim 31 wherein the therapeutically effective amount is an amount from about 0.1 to about 500 mg per mL of solution.

33. A method of treating solid tumors in a subject which comprises administering to the subject a therapeutically effective amount of any one of the compounds of claim 1.

34. The method of claim 33 wherein the therapeutically effective amount is an amount from about 0.1 to about 10 mg/kg of body weight.

35. A method of inhibiting growth of tumor cells in a host in need of treatment therefor which comprises administering to the host a therapeutically effective amount of any one of the compounds of claim 1.

36. The method of claim 35 wherein the therapeutically effective amount is an amount from about 0.1 to about 10 mg/kg of body weight.

* * * * *